United States Patent
Hirsch et al.

(10) Patent No.: US 12,281,145 B2
(45) Date of Patent: Apr. 22, 2025

(54) TRUNCATED DYSFERLIN FOR TREATMENT OF DYSFERLINOPATHY

(71) Applicants: The University of North Carolina at Chapel Hill, Chapel Hill, NC (US); Texas Tech University System, Lubbock, TX (US)

(72) Inventors: Matthew Louis Hirsch, Chapel Hill, NC (US); R. Bryan Sutton, Lubbock, TX (US)

(73) Assignees: The University of North Carolina at Chapel Hill, Chapel Hill, NC (US); Texas Tech University System, Lubbock, TX (US)

( * ) Notice: Subject to any disclaimer, the term of this patent is extended or adjusted under 35 U.S.C. 154(b) by 377 days.

(21) Appl. No.: 16/310,207

(22) PCT Filed: Jun. 16, 2017

(86) PCT No.: PCT/US2017/037822
§ 371 (c)(1),
(2) Date: Dec. 14, 2018

(87) PCT Pub. No.: WO2017/218866
PCT Pub. Date: Dec. 21, 2017

(65) Prior Publication Data
US 2020/0010521 A1 Jan. 9, 2020

Related U.S. Application Data

(60) Provisional application No. 62/351,701, filed on Jun. 17, 2016.

(51) Int. Cl.
| | | |
|---|---|---|
| C07K 14/47 | (2006.01) | |
| A61K 38/00 | (2006.01) | |
| A61K 48/00 | (2006.01) | |
| A61P 21/00 | (2006.01) | |
| C12N 15/86 | (2006.01) | |

(52) U.S. Cl.
CPC .......... *C07K 14/4707* (2013.01); *A61P 21/00* (2018.01); *C12N 15/86* (2013.01); *A61K 38/00* (2013.01); *A61K 48/00* (2013.01); *C12N 2750/14143* (2013.01)

(58) Field of Classification Search
CPC . C07K 14/4707; C07K 14/4716; A61P 21/00; C12N 15/86; C12N 2750/14143; C12N 2750/14052; A61K 38/00; A61K 48/00; A61K 48/005; A01K 67/0275
See application file for complete search history.

(56) References Cited

U.S. PATENT DOCUMENTS

2010/0266551 A1    10/2010    Richard et al.

FOREIGN PATENT DOCUMENTS

| RU | 2527073 C2 | 8/2014 |
|---|---|---|
| WO | 2007/089632 | 8/2007 |
| WO | 2007/124148 | 11/2007 |
| WO | 2009/016326 | 2/2009 |

OTHER PUBLICATIONS

Pramono et al. "Identification and characterization of human dysferlin transcript variants: implications for dysferlin mutational screening and isoforms." Human genetics 125.4 (2009): 413-420 (Year: 2009).*
Evesson et al. "Reduced plasma membrane expression of dysferlin mutants is attributed to accelerated endocytosis via a syntaxin-4-associated pathway." Journal of Biological Chemistry 285.37 (2010): 28529-28539 (Year: 2010).*
Aartsma-Rus et al. "Therapeutic exon skipping for dysferlinopathies?" European journal of human genetics 18.8 (2010): 889-894 (Year: 2010).*
"Examination Report corresponding to European Application No. 17814149.5 dated Oct. 29, 2020".
"Office Action corresponding to Russian Application No. 2019100990 dated Nov. 18, 2020".
Cao, Shanbo , et al., "Isolation and Culture of Primary Bovine Embryonic Stem Cell Colonies by a Novel Method", J. Exp. Zoology 311A:368-376 (2009).
Keskin, Ozlem , et al., "A new, structurally nonredundant, diverse data set of protein-protein Interfaces and its implications", Protein Science 13:1043-1055 (2004).
Pakula, Andrewa., "Genetic Analysis of Protein Stability and Function", Annu. Rev. Genet. 23:289-310 (1989).
International Preliminary Report on Patentability corresponding to International Application No. PCT/US2017/037822 mailed Dec. 27, 2018.
Azakir et al. "Modular Dispensability of Dysferlin C2 Domains Reveals Rational Design for Mini-dysferlin Molecules", Journal of Biological Chemistry 287(13):27629-27636 (2012).
Notification of Transmittal of the International Search Report and the Written Opinion of the International Searching Authority, or the Declaration corresponding to International Application No. PCT/US2017/037822 mailed Sep. 21. 2017.
Hirsch, Presentation of Jain Foundation's Seventh Dysferlin Conference, Toronto, Canada, Nov. 4-7, 2015 (10 pages).
Llanga et al., Poster presentation, American Society of Gene and Cell Therapy Annual Meeting, Washington, DC, May 4-7, 2016 (1 page).
Nagy et al. "Hip region muscular dystrophy and emergence of motor deficits in dysferlin-deficient Bla/J mice", Physiological Reporis 5(6):e13173 pp. 1-16 (2017).
Sondergaard et al. "AAV. Dysferlin Overlap Vectors Restore Function in Dysferlinopathy Animal Models", Ann. Clin. Transl. Neurol. 2(3):256-270 (2015).

(Continued)

*Primary Examiner* — Jeremy C Flinders
*Assistant Examiner* — Alexander W Nicol
(74) *Attorney, Agent, or Firm* — Myers Bigel, P.A.

(57) ABSTRACT

This invention relates to a truncated dysferlin nucleic acid and protein, vectors (e.g., adeno-associated virus vectors) comprising the nucleic acid and methods of using the same for delivery of dysferlin to a cell or a subject and treating dysferlinopathy.

15 Claims, 12 Drawing Sheets

Specification includes a Sequence Listing.

(56) References Cited

OTHER PUBLICATIONS

Ghosh et al. "Efficient Transgene Reconstitution with Hybrid Dual AAV Vectors Carrying the Minimized Bridging Sequences", Human Gene Therapy 22:77-83 (2011).
Grose et al. "Homologous Recombination Mediates Functional Recovery of Dysferlin Deficiency following AAV5 Gene Transfer", PLoS One 7(6):e39233 (2012) pp. 1-10.
Lostal et al. "Efficient recovery of dysferlin deficiency by dual adeno-associated vector-mediated gene transfer", Hum. Mol. Genet. 19(10):1897-1907 (2010).
European Search Report corresponding to European Application No. 17814149.5 dated Mar. 9, 2020.
Krahn et al. "G.O.5 Partial functionality of a Mini-dysferlin molecule identified in a patient affected with moderately severe primary dysferlinopathy", Neuromuscular Disorders: 18(9-10):781 (2008).
Krahn et al. "G.P.4.10 Functional evaluation of a putative mini-dysferlin identified in a patient with moderate Miyoshi myopathy phenotype", Neuromuscular Disorders 17(9-10):790 (2007).
Aartsma-Rus et al. "Therapeutic exon skipping for dysferlinopathies?", European Journal of Human Genetics 18:889-894 (2010).
Sondergaard et al. "AAV.Dysferlin Overlap Vectors Restore Function in Dysferlinopathy Animal Models", Annals of Clinical and Translational Neurology 2(3):256-270 (2015).
Abdullah et al. "Quantitation of the Calcium and Membrane Binding Properties of the C2 Domains of Dysferlin", Biophysical Journal 106(2):382-389 (2014).
Hirsch et al. "Little Vector, Big Gene Transduction; Fragmented Genome Reassembly of Adeno-associated Virus", Molecular Therapy 18(1):6-8 (2010).
Hirsch et al. "Oversized AAV Transduction is Mediated via a DNA-PKcs-Independent, Rad51C-dependent Repair Pathway", Molecular Therapy 21(12):2205-2216 (2013).
Llanga et al. "Structure-Based Designed Nano-Dysferlin Significantly Improves Dysferlinopathy in BLA/J Mice", Molecular Therapy 25(9):2150-2162 (2017).
"Office Action corresponding to Japanese Application No. 2018-566292 issued Jun. 4, 2021".
Llanga, Telmo , et al., "AAV Transduction of a Truncated Dysferlin Improves Dysferlinopathy", Mol. Ther. 24(1):S249-S250 (May 2016).
"Office Action corresponding to Chinese Application No. 201780050284.7 issued Aug. 25, 2021".
"Office Action corresponding to Japanese Application No. 2018-566292 issued Mar. 3, 2022".
"Office Action corresponding to Russian Application No. 2019100990 dated Feb. 16, 2022".
"Office Action corresponding to Israeli Application No. 263577 issued Jan. 17, 2022".
"Office Action corresponding to Korean Application No. 10-2018-7037990 issued Feb. 15, 2022".
"Office Action corresponding to Brazilian Application No. 112018076127-3 issued Oct. 11, 2022".
"Office Action corresponding to Japanese Application No. 2018-566292 mailed Aug. 1, 2022".
"Office Action corresponding to Korean Application No. 10-2018-7037990 issued Aug. 26, 2022".
"Office Action corresponding to Chinese Application No. 201780050284.7 issued Aug. 29, 2022".
"Office Action corresponding to Chinese Application No. 201780050284.7 issued Apr. 24, 2022".
"Office Action corresponding to Australian Application No. 2017285423 issued Oct. 25, 2022".

* cited by examiner

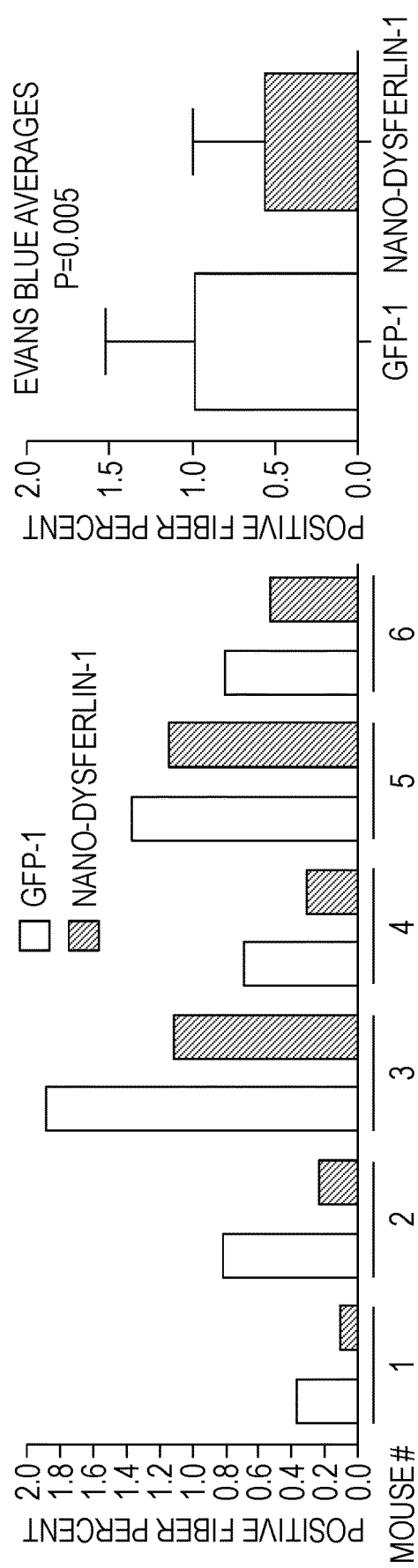
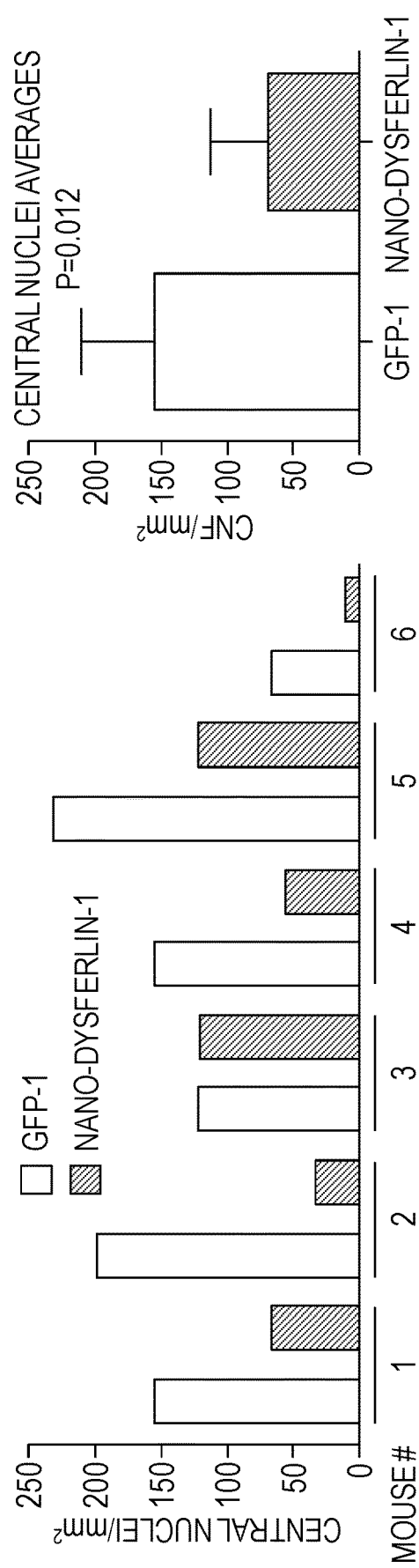
FIG. 3A
FIG. 3B

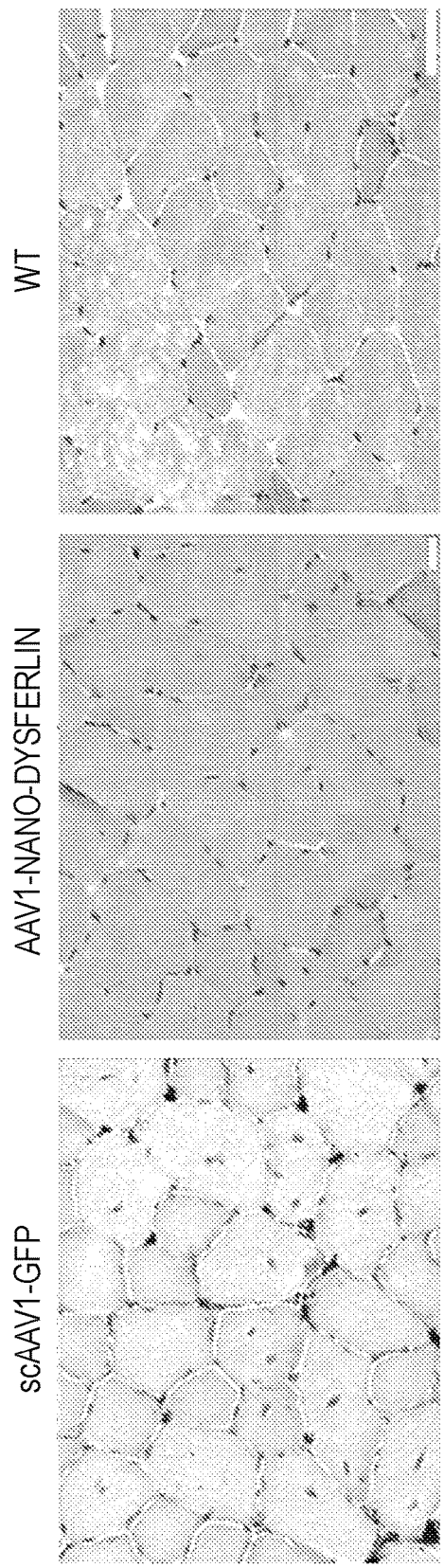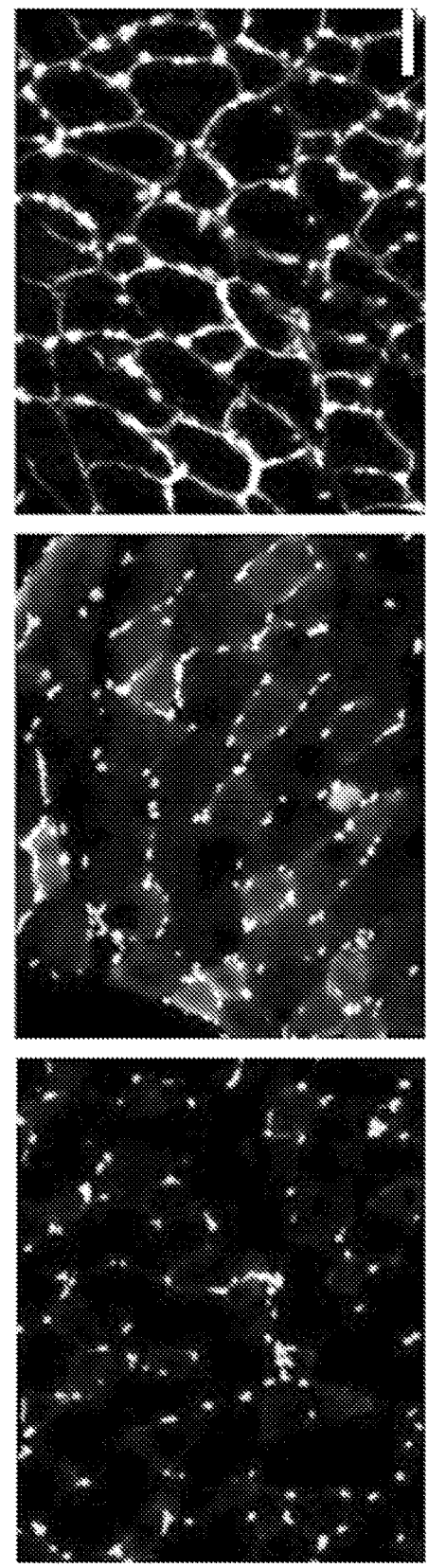
FIG. 3C
FIG. 3D

TRUNCATED DYSFERLIN FOR TREATMENT OF DYSFERLINOPATHY

STATEMENT OF PRIORITY

This application is a 35 U.S.C. § 371 national phase application of PCT Application PCT/US2017/037822 filed Jun. 16, 2017, which claims the benefit of U.S. Provisional Application Ser. No. 62/351,701, filed Jun. 17, 2016, the entire contents of each of which are incorporated by reference herein in its entirety.

STATEMENT OF FEDERAL SUPPORT

This invention was made with government support under Grant Number AI072176, AR064369 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-780_ST25.txt, 118,763 bytes in size, generated on Dec. 7, 2018 and filed via EFS-Web, is provided in lieu of a paper copy. This Sequence Listing is hereby incorporated by reference into the specification for its disclosures.

FIELD OF THE INVENTION

This invention relates to a truncated dysferlin nucleic acid and protein, vectors (e.g., adeno-associated virus (AAV) vectors) comprising the nucleic acid and methods of using the same for delivery of dysferlin to a cell or a subject and treating dysferlinopathy.

BACKGROUND OF THE INVENTION

Dysferlinopathy is a muscular dystrophy that is caused by mutations in the dysferlin gene regardless of the clinical presentation. The symptoms of dysferlinopathy vary significantly between individuals. Clinical presentations most commonly associated with dysferlinopathy include limb girdle muscular dystrophy (LGMD2B), Miyoshi myopathy, distal myopathy with anterior tibial onset (DMAT), proximodistal weakness, pseudometabolic myopathy, and hyper-CKemia. Most commonly, patients report distal muscle weakness in the second decade of life with loss of distal motor function within the ensuing decade. Patients generally require a wheelchair for motility with varying degrees of overall body control. As dysferlinopathy is often misdiagnosed, its incidence has not been determined. To date, there is no effective treatment to slow the loss of muscle function or reverse/improve the dystrophic phenotype.

Dysferlin is a vesicle and membrane associated protein that is involved in maintenance of membrane integrity. Dysferlin displays a calcium sensing domain which likely triggers intracellular signaling repair networks upon membrane damage. It is thought that dysferlin-containing intracellular vesicles traffic to the site of membrane damage and normally vesicle fusion results in membrane integrity. Although the function of dysferlin function is not well characterized, in its absence, muscle membranes are more susceptible to mild forms of stress.

The coding sequence of the dysferlin protein is >6.5 kb which exceeds the packaging capacity of a single adeno-associated viral (AAV) vector capsid, making the treatment of dysferlinopathy not possible by a simple AAV-mediated gene addition strategy. Therefore, creative intracellular gene construction approaches have been investigated for AAV mediated dysferlin delivery that rely on multiple capsids carrying transgenic DNA pieces that must be assembled by host enzymes. This "oversized AAV gene therapy" approach has not yet been validated in the clinic and is inherently less efficient at several levels. Previous attempts at "oversized" AAV transduction of dysferlin encountered difficulty getting detectable levels of dysferlin restored in vivo.

The present invention overcomes shortcomings in the art by providing a truncated hybrid dysferlin gene that can be packaged in a single AAV and has been demonstrated to be effective in vivo.

SUMMARY OF THE INVENTION

The present invention provides truncated dysferlin polypeptides and polynucleotides encoding the same. The truncated polypeptides retain at least a portion of the biological activity of wild-type dysferlin and the polynucleotides are capable of being packaged into viral genomes and viral vectors due to their decreased length relative to the wild-type polynucleotide.

One aspect of the invention relates to a polynucleotide encoding a truncated mammalian dysferlin polypeptide, wherein at least a substantial portion of each of the C2D and C2F domains of the polypeptide is deleted. The invention further relates to an expression cassette, a vector (e.g., a viral vector) and a recombinant viral particle (e.g., AAV particle) comprising the polynucleotide of the invention and a transformed cell and transgenic animal comprising the polynucleotide, expression cassette, or vector of the invention. Further provided are pharmaceutical formulations comprising a virus particle of the invention in a pharmaceutically acceptable carrier.

An additional aspect of the invention relates to a truncated mammalian dysferlin polypeptide, wherein at least a substantial portion of each of the C2D and C2F domains of the polypeptide is deleted.

A further aspect of the invention relates to a method of producing a recombinant AAV particle, comprising providing to a cell permissive for AAV replication: (a) a recombinant AAV template comprising (i) the polynucleotide or the expression cassette of the invention, and (ii) an inverted terminal repeat (ITR); (b) a polynucleotide comprising Rep coding sequences and Cap coding sequences; under conditions sufficient for the replication and packaging of the recombinant AAV template; whereby recombinant AAV particles are produced in the cell.

A further aspect of the invention relates to a method of delivering dysferlin to a cell, comprising contacting the cell with the recombinant viral particle (e.g., AAV particle) of the invention, thereby delivering dysferlin to the cell.

Another aspect of the invention relates to a method of administering dysferlin to a mammalian subject, comprising administering to the mammalian subject a cell that has been contacted with the recombinant viral particle (e.g., AAV particle) of the invention, thereby administering dysferlin to the mammalian subject.

A further aspect of the invention relates to a method of treating dysferlinopathy in a mammalian subject in need thereof, comprising administering to the mammalian subject a cell that has been contacted with the recombinant viral particle (e.g., AAV particle) of the invention, thereby treating the dysferlinopathy.

Another aspect of the invention relates to a method of administering dysferlin to a mammalian subject comprising administering to the mammalian subject the recombinant viral particle (e.g., AAV particle) of the invention, thereby administering dysferlin to the mammalian subject.

An additional aspect of the invention relates to a method of treating dysferlinopathy in a mammalian subject in need thereof, comprising administering to the mammalian subject the recombinant viral particle (e.g., AAV particle) of the invention, thereby treating the dysferlinopathy.

Another aspect of the invention relates to use of the recombinant viral particle (e.g., AAV particle) of the invention for delivering dysferlin to a cell.

An additional aspect of the invention relates to use of a cell that has been contacted with the recombinant viral particle (e.g., AAV particle) of the invention for delivering dysferlin to a mammalian subject.

A further aspect of the invention relates to use of the recombinant viral particle (e.g., AAV particle) of the invention for delivering dysferlin to a mammalian subject.

A further aspect of the invention relates to use of the recombinant viral particle (e.g., AAV particle) of the invention for treating dysferlinopathy in a mammalian subject.

Another aspect of the invention relates to use of the recombinant viral particle (e.g., AAV particle) of the invention for the manufacture of a medicament for delivering dysferlin to a cell.

An additional aspect of the invention relates to use of a cell that has been contacted with the recombinant viral particle (e.g., AAV particle) of the invention for the manufacture of a medicament for delivering dysferlin to a mammalian subject.

A further aspect of the invention relates to use of the recombinant viral particle (e.g., AAV particle) of the invention for the manufacture of a medicament for delivering dysferlin to a mammalian subject.

A further aspect of the invention relates to use of the recombinant viral particle (e.g., AAV particle) of the invention for the manufacture of a medicament for treating dysferlinopathy in a mammalian subject.

These and other aspects of the invention are set forth in more detail in the description of the invention below.

BRIEF DESCRIPTION OF THE DRAWINGS

(FIG. 1A) Human dysferlin isoform 8, the parent cDNA from which Nano-Dysferlin was derived, contains C2A, C2B, C2C, FerA, Dysf, C2D, C2E, C2F, C2G, and a transmembrane domain at a size of 6,240 nt. Nano-Dysferlin lacks C2D, C2E, and C2F domains, bringing the cDNA size down to 4,356 nt. (FIG. 1B) Western blot analysis of transfected c2c12 mouse myoblasts revealed that soluble protein lysate did not contain either Nano-Dysferlin or full-length dysferlin. Contrastingly, membrane-associated protein lysate contains both dysferlin and Nano-Dysferlin. (FIG. 1C) Immunofluorescence imaging in HeLa cells revealed a similar intracellular distribution of dysferlin and Nano-Dysferlin. Scale bar, 20 μm. (FIG. 1D) Nano-Dysferlin did not display significant toxicity in dysferlin-deficient patient cells, as measured by alamar Blue absorbance at low (0.5 mg), medium (1 mg), or high (1.5 mg) plasmid doses. 0.5% sodium hypochlorite was used as the positive killing positive control. Mean+SD is shown.

(FIG. 2A) Two Nano-Dysferlin AAV-ITR cassettes were designed that differ in size based on promoter and poly adenylation (polyA) sequences. JeT-Nano-Dysferlin is 4,849 nt in size, whereas CMV-Nano-Dysferlin is 5,597 nt. (FIG. 2B) Western blot following transfection of constructs depicted in (FIG. 2A) (along with dysferlin and GFP controls) in 293 cells and stained with the indicated antibodies. (FIG. 2C) AAV viral packaging was analyzed by alkaline gel electrophoresis and SYBR gold staining. Intact packaging was observed for the JeT-Nano-Dysferlin cassette, whereas fragmented packaging was seen for the CMV-Nano-Dysferlin cassette (the numbers indicated the packaged genomes found in each CsCl gradient fraction). (FIG. 2D) Western blot analysis of 293 cells treated with the indicated AAV vectors at the indicated amounts per cell.

FIGS. 3A-3D show AAV-Nano-Dysferlin significantly improves muscle histology following intramuscular injection. (FIG. 3A) The TA muscles of BLA/J dysferlin-deficient mice were contralaterally injected with either AAV1-CMV-GFP or AAV1-JeT-Nano-Dysferlin. Evans blue dye was intraperitoneally administered 40 hr prior to sacrifice. Evans blue dye-positive fibers were normalized to total fibers. Matched pairs statistical analysis revealed a significant reduction of Evans blue dye-positive fibers in AAV1-JeT-Nano-Dysferlin-treated TA compared to contralateral controls. (FIG. 3B) Central nucleated fibers, a marker for muscle turnover, were reduced in all but one muscle treated with AAV1-JeT-Nano-Dysferlin, and statistical analysis showed a significant decrease in central nucleation of Nano-Dysferlin-treated muscles (p=0.0125). (FIG. 3C) Representative images show improved muscle histology in AAV1-JeT-Nano-Dysferlin-injected muscle, which resembles WT muscle more closely than BLA/J dysferlin-deficient muscle. Scale bar, 40 m. (FIG. 3D) Romeo dysferlin antibody IF staining revealed a different distribution pattern between endogenous dysferlin and Nano-Dysferlin. Approximately 30% of fibers stained positive for Nano-Dysferlin (total fiber n=455). Scale bar, 40 μm. Mean+SD is shown.

(FIG. 4A) Creatine kinase activity was found to be higher in AAV9-CMV-GFP-treated mice compared to AAV9-JeT-Nano-Dysferlin-treated mice. (FIG. 4B) Rearing performance was significantly improved over an hour evaluation in BLA/J mice injected with AAV9JeT-Nano-Dysferlin compared to AAV9-CMV-GFP-treated mice. (FIG. 4C) Analysis of rearing over time demonstrated AAV9-JeT-Nano-Dysferlin-treated mice had increased stamina, indicated by consistent rearing over an hour compared to AAV9CMV-GFP control mice. Mean+SD is shown.

(FIG. 5A) Central nucleated fibers, whose presence indicates regeneration and turnover were reduced non-significantly, yet trending (p=0.0835) in Nano-Dysferlin-treated muscles compared to GFP-treated muscles. (FIG. 5B) Evans blue dye whole muscle absorbance assay, a measure of muscle damage, was significantly decreased in the gluteal muscles of AAV9-JeT-Nano-Dysferlin-injected mice (p=0.037). (FIG. 5C) Representative image of Evans blue dye-positive fiber histology shows a marked decrease in muscle damage of AAV9-JeT-Nano-Dysferlin-treated muscles compared to the AAV9-CMV-GFP-treated controls. Statistical analysis showed an almost significant reduction (p=0.056) of Evans blue dye-positive fibers in the gluteal muscles of AAV9-JeT-Nano-Dysferlin-treated mice. Scale bar, 100 m. (FIG. 5D) Minimal Feret diameter, a measure of fiber size, was obtained from gluteal muscle WGA lectin-stained muscle sections, with a significant difference between treatments by unpaired t test (p<0.0001). (FIG. 5E) Oil-Red-O staining for hydrophobic and negatively charged lipids (arrows); this representative image showed a marked difference between treatments. Scale bar, 300 μm. Mean+SD is shown.

(FIG. 6A) Horizontal activity was measured in IV treated mice, with no difference between treatments in the first 30 minutes (p=0.58), while there was a non-significant (p=0.13), yet trending higher horizontal activity in Nano-Dysferlin treated mice over the last 30 minutes of observation. (FIG. 6B) H&E staining was performed in gluteal muscles and psoas muscle and analyzed for total central nuclei normalized to total fibers, no difference by this method of measuring central nucleation was found between treatments. Mean+SD shown.

(FIG. 9A) The expected amplicon for RT-QPCR was observed for Nano-Dysferlin in intramuscularly treated Tibialis muscles, while a fainter signal was also observed in their contralateral control, but not in negative controls, suggesting vector leakage from the site of injection. Due to amplicon size, PCR samples were treated with Exo-Sap It to remove primer dimers, this was also done for (FIG. 9B) RT-QPCR for Nano-Dysferlin in the gluteal muscles, which showed a signal confirming the presence of transcribed mRNA nearly 8 months after a single systemic injection.

DETAILED DESCRIPTION OF THE INVENTION

Figure 1A:
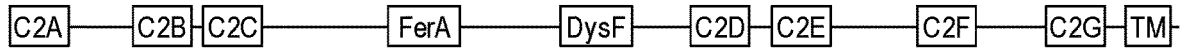
FIGS. 1A-1D show Nano-Dysferlin design and expression in mammalian cells.
Figure 1A:

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., Patent In User Manual, 99-102 (November 1990) (U.S. Patent and Trademark Office).

Except as otherwise indicated, standard methods known to those skilled in the art may be used for the construction of recombinant AAV (rAAV) constructs, packaging vectors expressing the AAV Rep and/or Cap sequences, and transiently and stably transfected packaging cells. Such techniques are known to those skilled in the art. See, e.g., SAMBROOK et al. MOLECULAR CLONING: A LABORATORY MANUAL 2nd Ed. (Cold Spring Harbor, NY, 1989); AUSUBEL et al. CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

Definitions

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps and those that do not materially affect the basic and novel characteristic(s) of the claimed invention (e.g., production of dysferlin). Thus, the term "consisting essentially of" as used herein should not be interpreted as equivalent to "comprising."

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al. VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al. VIROLOGY, volume 2, chapter 69 (4th ed., Lippincott-Raven Publishers); and Table 1.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al. VIROLOGY, volume 2, chapter 69 (4th ed., Lippincott-Raven Publishers). A number of relatively new AAV serotypes and clades have been identified (See, e.g., Gao et al. (2004) *J. Virol.* 78:6381; Moris et al. (2004) *Virol.* 33-:375; and Table 1).

TABLE 1

| Complete Genomes | GenBank Accession Number |
|---|---|
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |

TABLE 1-continued

| Complete Genomes | GenBank Accession Number |
|---|---|
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |

TABLE 1-continued

| Complete Genomes | GenBank Accession Number |
|---|---|
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The AAV particles and genomes of the present invention can be from any AAV. The genomic sequences of various serotypes of AAV, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC 001829, NC 001862, NC 000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching AAV nucleic acid and amino acid sequences. See also, e.g., Bantel-Schaal et al. (1999) *J. Virol.* 73: 939; Chiorini et al. (1997) *J. Virol.* 71:6823; Chiorini et al. (1999) *J. Virol.* 73:1309; Gao et al. (2002) *Proc. Nat. Acad. Sci. USA* 99:11854; Moris et al. (2004) *Virol.* 33-:375-383; Mori et al. (2004) *Virol.* 330:375; Muramatsu et al. (1996) *Virol.* 221:208; Ruffing et al. (1994) *J. Gen. Virol.* 75:3385; Rutledge et al. (1998) *J. Virol.* 72:309; Schmidt et al. (2008) *J. Virol.* 82:8911; Shade et al., (1986) *J. Virol.* 58:921; Srivastava et al. (1983) *J. Virol.* 45:555; Xiao et al. (1999) *J. Virol.* 73:3994; international patent publications WO 00/28061, WO 99/61601, WO 98/11244; and U.S. Pat. No. 6,156,303; the disclosures of which are incorporated by reference herein for teaching AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" of a cell by AAV refers to AAV-mediated transfer of genetic material into the cell. See, e.g., FIELDS et al. VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

As used herein, the term "truncated polypeptide" refers to a polypeptide in which one or more of the amino acid residues present in the wild-type polypeptide have been deleted. The deleted residues may be at the N-terminus, the C-terminus, internal, or any combination thereof.

A "polynucleotide" is a sequence of nucleotide bases, and may be RNA, DNA or DNA-RNA hybrid sequences (including both naturally occurring and non-naturally occurring nucleotide), and can be either single or double stranded DNA sequences.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, CABIOS 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. In some embodiments, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone or a plasmid.

The virus vectors of the invention can further be duplexed AAV particles as described in international patent publication WO 01/92551 (the disclosure of which is incorporated herein by reference in its entirety). Thus, in some embodiments, double stranded (duplex) genomes can be packaged.

A "rAAV vector genome" or "rAAV genome" is an AAV genome (i.e., vDNA) that comprises one or more heterologous nucleic acid sequences. rAAV vectors generally require only the 145 base ITR in cis to generate virus. Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like.

The virus vectors of the invention can further be "targeted" virus vectors (e.g., having a directed tropism) and/or a "hybrid" AAV (i.e., in which the viral ITRs and viral capsid are from different AAV) as described in international patent publication WO 00/28004 and Chao et al., (2000) *Mol. Therapy* 2:619.

Further, the viral capsid or genomic elements can contain other modifications, including insertions, deletions and/or substitutions.

The term "template" or "substrate" is used herein to refer to a polynucleotide sequence that may be replicated to produce the AAV viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, AAV "Rep coding sequences" indicate the nucleic acid sequences that encode the AAV non-structural proteins that mediate viral replication and the production of new virus particles. The AAV replication genes and proteins have been described in, e.g., FIELDS et al. VIROLOGY, volume 2, chapters 69 & 70 (4th ed., Lippincott-Raven Publishers).

The "Rep coding sequences" need not encode all of the AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the AAV "cap coding sequences" encode the structural proteins that form a functional AAV capsid (i.e., can package DNA and infect target cells). Typically, the cap coding sequences will encode all of the AAV capsid subunits, but less than all of the capsid subunits may be encoded as long as a functional capsid is produced. Typically, but not necessarily, the cap coding sequences will be present on a single nucleic acid molecule.

The capsid structure of AAV are described in more detail in BERNARD N. FIELDS et al., VIROLOGY, volume 2, chapters 69 & 70 (4th ed., Lippincott-Raven Publishers).

The term "substantial portion," as used herein with respect to a polypeptide domain, refers to the majority of the amino acid residues in the domain (i.e., at least 50%), e.g., at least about 80% or more of the residues, e.g., at least 85%, 90%, or 95% of the residues. With respect to a substantial portion of the domain being deleted, the remaining residues of the domain retain less than about 20% of the biological activity of the wild-type domain, e.g., less than about 15%, 10%, or 5% of the biological activity. With respect to a substantial portion of the domain being present, the residues of the domain retain at least about 70% of the biological activity of the wild-type domain, e.g., at least about 80%, 90%, or 95% of the biological activity.

Truncated Dysferlin Polynucleotides and Polypeptides

The present invention provides truncated dysferlin polypeptides and polynucleotides encoding the same. The truncated polypeptides retain at least a portion of the biological activity of wild-type dysferlin and the polynucleotides are capable of being packing into viral genomes and viral vectors due to their decreased length relative to the wild-type polynucleotide. In certain embodiments, the truncated polypeptides retain at least about 20% of the biological activity of wild-type dysferlin, e.g., at least about 20%, 30%, 40%, 50%, 60%, 70%, 80%, or 90% or more. The biological activity retained may be maintenance of muscle membrane integrity, which can be measured using techniques well known in the art and disclosed herein.

One aspect of the invention relates to a polynucleotide encoding a truncated mammalian dysferlin polypeptide, wherein at least a substantial portion of each of the C2D and C2F domains of the polypeptide is deleted. In some embodiments, at least a substantial portion of the C2E domain of the polypeptide also is deleted. In some embodiments, at least a substantial portion of one or more of the C2B, C2C, and C2D domains of the polypeptide also is deleted. The deletions may be a deletion of some or all of the domain, e.g., 80%, 85%, 90%, 95%, or more of the domain. The deletions may be at the N-terminal boundary of the domain, the C-terminal boundary of the domain, internal to the domain, or any combination thereof.

In certain embodiments, the polynucleotide encodes a truncated dysferlin polypeptide comprising, consisting essentially of, or consisting of at least a substantial portion of the C2A, C2C, FerA, DysF, C2G, and TM domains. In certain embodiments, the polynucleotide encodes a truncated dysferlin polypeptide comprising, consisting essentially of, or consisting of at least a substantial portion of the C2A, C2B, C2C, FerA, DysF, C2G, and TM domains, e.g., a majority of each domain, e.g., 80%, 85%, 90%, 95%, or more of the domain. In certain embodiments, the polynucleotide encodes a truncated dysferlin polypeptide comprising, consisting essentially of, or consisting of at least a substantial portion of the C2A, FerA, DysF, C2G, and TM domains.

In certain embodiments, the polynucleotide encoding truncated dysferlin has a length of about 5 kb or less, e.g., about 4.5 kb, 4 kb, or less. In some embodiments, the polynucleotide is a non-naturally occurring polynucleotide.

In some embodiments, the polynucleotide encodes a truncated dysferlin polypeptide that is a mammalian dysferlin polypeptide, e.g., a human dysferlin polypeptide.

The nucleotide and amino acid sequences of dysferlin are well known in the art and can be found in databases such as GenBank. For example, human dysferlin nucleotide sequences are found at accession number AF075575.1 and human dysferlin amino acid sequences are found at accession number NP_003485.1. Other mammalian dysferlin amino acid sequences include rat (NP_001101339.1), mouse (AAG17046.2), cow (NP_001095960.1), goat (XP_013822998.1), horse (XP_008534159.1), sheep (XP_014949936.1), and dog (XP_003432282.1).

The domain structure of the dysferlin polypeptide is well known in the art. As shown in FIG. 1A, dysferlin comprises the following domains: C2A, C2B, C2C, FerA, DysF, C2D, C2E, C2F, C2G, and TM. The exact boundaries of each domain may vary among orthologs and variants. The approximate amino acid range for each domain in human dysferlin is shown in Table 2 (amino acid numbering based on SEQ ID NO: 11. The listed domain boundaries may vary by up to about 20 residues, e.g., about 5, 10, 15, or 20 residues.

TABLE 2

| Domain | Amino Acid Range |
|--------|------------------|
| C2A    | 1-124            |
| C2B    | 219-352          |
| C2C    | 366-515          |
| FerA   | 670-782          |
| DysF   | 864-1097         |
| C2D    | 1137-1281        |
| C2E    | 1314-1465        |
| C2F    | 1579-1696        |
| C2G    | 1789-1994        |
| TM     | 2045-2067        |

In some embodiments, the polynucleotide is:
(a) a polynucleotide comprising a sequence at least 80% identical to any one of SEQ ID NOS: 1-5 (e.g., at least about 80%, 85%, 90%, 91%, 92%, 93%, 94%, 95%, 96%, 97%, 98%, or 99% identical);

(b) a polynucleotide comprising a sequence encoding a polypeptide at least 80% identical to any one of SEQ ID NOS:6-10 (e.g., at least about 80%, 85%, 90%, 91%, 92%, 93%, 94%, 95%, 96%, 97%, 98%, or 99% identical); or (c) a polynucleotide that differs from the polynucleotide of (a) or (b) due to codon degeneracy.

In some embodiments, the polynucleotide is:
(a) a polynucleotide comprising a sequence identical to any one of SEQ ID NOS: 1-5;
(b) a polynucleotide comprising a sequence encoding a polypeptide identical to any one of SEQ ID NOS:6-10; or
(c) a polynucleotide that differs from the polynucleotide of (a) or (b) due to codon degeneracy.

Another aspect of the invention is an expression cassette comprising the polynucleotide of the invention. The expression cassette may further comprise elements to enhance expression of the truncated dysferlin polypeptide. In some embodiments, the polynucleotide is operably linked to a promoter, e.g., a universal promoter or a muscle-specific or muscle-preferred promoter.

The invention also provides a vector, e.g., a viral vector, comprising the polynucleotide or expression cassette of the invention. The viral vector can be a parvovirus vector, e.g., an AAV vector. The invention further provides a recombinant parvovirus particle (e.g., a recombinant AAV particle) comprising the polynucleotide or expression cassette of the invention. Viral vectors and viral particles are discussed further below. The viral particle can have an altered tropism as compared to wild-type particles, e.g., due to the presence of modified capsid proteins. The altered tropism can be, without limitation, increased muscle targeting and/or decreased liver targeting.

An additional aspect of the invention relates to a transformed cell comprising the polynucleotide, expression cassette, and/or vector of the invention.

A further aspect of the invention relates to a transgenic animal comprising the polynucleotide, expression cassette, vector, and/or transformed cell of the invention. In some embodiments, the transgenic animal is a non-human animal, e.g., a non-human mammal, e.g., laboratory animal, e.g., a mouse rat, dog, or monkey. In some embodiments, the animal is a model of a disease.

Another aspect of the invention relates to a truncated mammalian dysferlin polypeptide, wherein at least a substantial portion of each of the C2D and C2F domains of the polypeptide is deleted. In some embodiments, at least a substantial portion of the C2E domain of the polypeptide also is deleted. In some embodiments, at least a substantial portion of one or more of the C2B, C2C, and C2D domains of the polypeptide also is deleted. The truncated polypeptides of the invention retain at least about 20% of at least one biological activity of wild-type dysferlin, e.g., maintaining muscle integrity, e.g., at least about 20%, 30%, 40%, 50%, 60%, 70%, 80%, 90%, or more of at least one biological activity. In some embodiments, the polypeptide is a non-naturally occurring polypeptide.

In certain embodiments, the polypeptide comprises, consists essentially of, or consists of at least a substantial portion of the C2A, C2C, FerA, DysF, C2G, and TM domains. In certain embodiments, the polypeptide comprises, consists essentially of, or consists of at least a substantial portion of the C2A, C2B, C2C, FerA, DysF, C2G, and TM domains. In certain embodiments, the polypeptide comprises, consists essentially of, or consists of at least a substantial portion of the C2A, FerA, DysF, C2G, and TM domains.

In some embodiments, the dysferlin polypeptide is a mammalian dysferlin polypeptide, e.g., a human dysferlin polypeptide.

In some embodiments, the polypeptide is:
(a) a polypeptide encoded by a polynucleotide comprising a sequence at least 80% identical to any one of SEQ ID NOS: 1-5 (e.g., at least about 80%, 85%, 90%, 91%, 92%, 93%, 94%, 95%, 96%, 97%, 98%, or 99% identical); or
(b) a polypeptide comprising a sequence at least 80% identical to any one of SEQ ID NOS:6-10 (e.g., at least about 80%, 85%, 90%, 91%, 92%, 93%, 94%, 95%, 96%, 97%, 98%, or 99% identical).

In some embodiments, the polypeptide is:
(a) a polypeptide encoded by a polynucleotide comprising a sequence identical to any one of SEQ ID NOS: 1-5; or
(b) a polypeptide comprising a sequence identical to any one of SEQ ID NOS:6-10.

Methods of Producing Virus Vectors

The present invention further provides methods of producing virus vectors. In one particular embodiment, the present invention provides a method of producing a recombinant AAV particle, comprising providing to a cell permissive for AAV replication: (a) a recombinant AAV template comprising (i) the polynucleotide or expression cassette of the invention, and (ii) an ITR; (b) a polynucleotide comprising Rep coding sequences and Cap coding sequences; under conditions sufficient for the replication and packaging of the recombinant AAV template; whereby recombinant AAV particles are produced in the cell. Conditions sufficient for the replication and packaging of the recombinant AAV template can be, e.g., the presence of AAV sequences sufficient for replication of the AAV template and encapsidation into AAV capsids (e.g., AAV rep sequences and AAV cap sequences) and helper sequences from adenovirus and/or herpesvirus. In particular embodiments, the AAV template comprises two AAV ITR sequences, which are located 5' and 3' to the polynucleotide of the invention, although they need not be directly contiguous thereto.

In some embodiments, the recombinant AAV template comprises an ITR that is not resolved by Rep to make duplexed AAV vectors as described in international patent publication WO 01/92551.

The AAV template and AAV rep and cap sequences are provided under conditions such that virus vector comprising the AAV template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so.

The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158: 67).

As a further alternative, the rep/cap sequences may be stably incorporated into a cell.

Typically the AAV rep/cap sequences will not be flanked by the TRs, to prevent rescue and/or packaging of these sequences.

The AAV template can be provided to the cell using any method known in the art. For example, the template can be supplied by a non-viral (e.g., plasmid) or viral vector. In particular embodiments, the AAV template is supplied by a herpesvirus or adenovirus vector (e.g., inserted into the E1a or E3 regions of a deleted adenovirus). As another illustration, Palombo et al., (1998) J. Virology 72:5025, describes a baculovirus vector carrying a reporter gene flanked by the AAV TRs. EBV vectors may also be employed to deliver the template, as described above with respect to the rep/cap genes.

In another representative embodiment, the AAV template is provided by a replicating rAAV virus. In still other embodiments, an AAV provirus comprising the AAV template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) Nature Med. 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the AAV template. The AAV rep/cap sequences and/or the AAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the AAV template can be provided as a plasmid template.

In another illustrative embodiment, the AAV rep/cap sequences and adenovirus helper sequences are provided by a single adenovirus helper vector, and the AAV template is integrated into the cell as a provirus. Alternatively, the AAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The AAV template can be provided as a separate replicating viral vector. For example, the AAV template can be provided by a AAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by ITRs so that these sequences are not packaged into the AAV virions.

Zhang et al., ((2001) *Gene Ther.* 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and AAV template as described, for example, by Urabe et al., (2002) *Human Gene Ther.* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV. Adenovirus mutants defective for late gene expression are known in the art (e.g., ts100K and ts149 adenovirus mutants).

Recombinant Virus Vectors

The virus vectors of the present invention are useful for the delivery of a polynucleotide encoding dysferlin to cells in vitro, ex vivo, and in vivo. In particular, the virus vectors can be advantageously employed to deliver or transfer the polynucleotide to animal, including mammalian, cells.

It will be understood by those skilled in the art that the polynucleotide encoding dysferlin can be operably associated with appropriate control sequences. For example, the polynucleotide encoding dysferlin can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the polynucleotide encoding dysferlin. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible. In some embodiments, the promoter is a muscle specific or preferred (including cardiac, skeletal and/or smooth muscle specific or preferred) promoter.

Inducible expression control elements are typically advantageous in those applications in which it is desirable to provide regulation over expression of the heterologous nucleic acid sequence(s). Inducible promoters/enhancer elements for gene delivery can be tissue specific or preferred promoter/enhancer elements, and include muscle specific or preferred (including cardiac, skeletal and/or smooth muscle specific or preferred) promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the polynucleotide encoding dysferlin is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering the polynucleotide encoding dysferlin into a broad range of cells, including dividing and non-dividing cells. The virus vectors can be employed to deliver a polynucleotide encoding dysferlin to a cell in vitro, e.g., to produce a polypeptide in vitro or for ex vivo gene therapy. The virus vectors are additionally useful in a method of delivering a polynucleotide encoding dysferlin to a subject in need thereof, e.g., to express dysferlin. In this manner, dysferlin can be produced in vivo in the subject. The subject can be in need of dysferlin because the subject has a deficiency of the polypeptide. Further, the method can be practiced because the production of dysferlin in the subject may impart some beneficial effect.

The virus vectors can also be used to produce dysferlin in cultured cells or in a subject (e.g., using the subject as a bioreactor to produce the polypeptide).

In general, the virus vectors of the present invention can be employed to deliver a polynucleotide encoding dysferlin to treat and/or prevent any disease state for which it is beneficial to deliver dysferlin. In some embodiments, the disease state is dysferlinopathy and/or any symptoms associated with dysferlinopathy. As used herein, the term "dysferlinopathy" refers to any disease, disorder, or condition associated with aberrant expression of dysferlin. Clinical presentations most commonly associated with dysferlinopathy include limb girdle muscular dystrophy (LGMD2B), Miyoshi myopathy, distal myopathy with anterior tibial onset (DMAT), proximodistal weakness, pseudometabolic myopathy, and hyperCKemia.

Virus vectors according to the instant invention find use in diagnostic and screening methods, whereby dysferlin is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults. The subject may be in need of the methods of the invention, i.e., has been diagnosed with or is suspected of having dysferlinopathy.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring or delivering a polynucleotide encoding dysferlin to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to muscle cells (e.g., skeletal muscle cells, cardiac muscle cells, smooth muscle cells and/or diaphragm muscle cells). In representative embodiments, the cell can be any progenitor cell. As a further possibility, the cell can be a stem cell (e.g., muscle stem cell). Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

A further aspect of the invention is a method of administering the virus vector to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ $10^{16}$, $10^{17}$, $10^{18}$ transducing units, optionally about $10^8$-$10^{15}$ transducing units.

In particular embodiments, more than one administration (e.g., two, three, four or more administrations) may be employed to achieve the desired level of gene expression over a period of various intervals, e.g., hourly, daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye [including intravitreal and subretinal], skeletal muscle, cardiac muscle, diaphragm muscle or brain).

Administration can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, *articularis* genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with dysferlinopathy) by limb perfusion, optionally isolated limb perfusion (e.g., by intravenous or intra-articular administration). In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

Delivery to a target tissue can also be achieved by delivering a depot comprising the virus vector and/or capsid. In representative embodiments, a depot comprising the virus vector and/or capsid is implanted into skeletal, smooth, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector according to the present invention is administered to skeletal muscle, diaphragm muscle and/or cardiac muscle (e.g., to treat and/or prevent dysferlinopathy).

In representative embodiments, the invention is used to treat and/or prevent disorders of skeletal, cardiac and/or diaphragm muscle.

In a representative embodiment, the invention provides a method of treating and/or preventing dysferlinopathy in a subject in need thereof, the method comprising: administering a treatment or prevention effective amount of a virus vector of the invention to a mammalian subject, wherein the virus vector comprises a polynucleotide encoding dysferlin, a mini-dysferlin, or a micro-dysferlin. In particular embodiments, the virus vector can be administered to skeletal, diaphragm and/or cardiac muscle as described elsewhere herein.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustainedrelease formulation. Further, the virus vector and/or virus capsid can be delivered adhered to a surgically implantable matrix (e.g., as described in U.S. Patent Publication No. 2004-0013645).

Having described the present invention, the same will be explained in greater detail in the following examples, which are included herein for illustration purposes only, and which are not intended to be limiting to the invention.

Example 1

Truncated Dysferlin

Several truncated human dysferlin clones were prepared. The sequences and domains are disclosed below. Residue numbering is based on human dysferlin isoform 8 (NP_003485.1) (SEQ ID NO:11). An alignment of the amino acid sequences of the clones is shown in Table 3 (SEQ ID NOS:6-11). Each of the clones was expressed in cells in vitro and demonstrated to produce dysferlin polypeptide.

Wild-type human dysferlin (isoform 8) (SEQ ID NO:11) [C2A,1:124]; [125:218]; [C2B,219:352]; [353:365]; [C2C, 366:515]; [516:669]; [FerA,670:782]; [783:863]; [DysF, 864:1097]; [1098:1136]; [C2D,1137:1281]; [1282:1313]; [C2E,1314:1465]; [1466:1578]; [C2F,1579:1696]; [1697: 1788]; [C2G,1789:1994]; [1995:2044]; [TM,2045:2067]; [2068:2080]

Wild-type dysferlin Domain Summary: C2A, C2B, C2C, FerA, DysF, C2D, C2E, C2F, C2G, TM Clone_318 No Flag (433) (SEQ ID NO:6) [C2A,1:124]; [147:155]; [157:166]; [172:180]; [187:192]; [199:205]; [C2B,222:352]; [353:365]; [C2C, 366:515]; [566:619]; [FerA,670:782]; [831:863]; [DysF-a,864:891]; [DysF-b, 942:1097][1098:1104][1282:1313]; [C2E,1314:1465]; [1496:1517]; [1523:1532]; [1538:1548]; [C2F,1579:1696]; [1718]; [1724:1741]; [1747:1765]; [C2G,1792:1994]; [2000:2003]; [2018:2030]; [2036:2044]; [TM,2045:2067]; [2068:2080]

Clone_318 Domain Summary: C2A, C2B, C2C, FerA, DysF*, C2E, C2F, C2G, TM

Clone_431 No Flag (431) (SEQ ID NO:7) [C2A,1:124]; [125:218]; [C2B,219:352]; [353:365]; [C2C,366:515]; [516: 669]; [FerA,670:782]; [783:863]; [DysF,864:1097]; [1098: 1136]; [C2G,1789:1823]; [C2G*, 1824:1836=TK-GAFGDMLDTP-]; [C2G,1837:(C1884A):1994]; [1995: 2044]; [TM,2045:2067]; [2068:2080]

Clone_431 Domain Summary: C2A, C2B, C2C, FerA, DysF, C2G*, TM

Clone_430 No Flag (430) (SEQ ID NO:8) [C2A,1:124]; [125:218]; [357:365]; [C2C,366:515]; [516:669]; [FerA, 670:782]; [783:863]; [DysF,864: 1097]; [1098:1136]; [C2G, 1789:(C1884A):1994]; [1995:2044]; [TM,2045:2067]; [2068:2080]

Clone_430 Domain Summary: C2A, C2C, FerA, DysF, C2G, TM

Clone_342 No Flag (426) (SEQ ID NO:9) [C2A,1:124]; [125:218]; [C2C,366:515]; [516:669]; [FerA,670:782]; [783:863]; [DysF,864:1097]; [1098:1136]; [C2F,1579: 1696]; [1697:1788]; [C2G,1789:(C1884A):1994]; [1995: 2044]; [TM,2045:2067]; [2068:2080]

Clone 342 Domain Summary: C2A, C2C, FerA, DysF, C2F, C2G, TM

Clone425 No Flag (425) (previously 341) (SEQ ID NO:10) [C2A,1:124]; [125:218]; [C2B,219:352]; [353:365]; [C2C,366:515]; [516:669]; [FerA,670:782]; [783: 863]; [DysF,864:1097]; [1098:1136]; [C2G, 1789:(C1884A): 1994]; [1995:2044]; [TM,2045:2067]; [2068:2080]

Clone_425 Domain Summary: C2A, C2B, C2C, FerA, DysF, C2G, TM

*—indicates an interruption in the domain range relative to the wild-type domain ranges.

TABLE 3

(SEQ ID NOS: 11, 6, 7, 8, 9, 10, respectively)

```
                                  10        20        30        40        50        60        70        80        90        100
                                   |         |         |         |         |         |         |         |         |         |
full Length dysferlin     MLRVFILYAENVHTPDTDISDAYCSAVFAGVKKRTKVIRNSVNPVWNEGFEWDLKGIPLDQGSELHVVVKDHETMGRNRFLGEAKVPLREVLATPSLSAS
318                       MLRVFILYAENVHTPDTDISDAYCSAVFAGVKKRTKVIRNSVNPVWNEGFEWDLKGIPLDQGSELHVVVKDHETMGRNRFLGEAKVPLREVLATPSLSAS
431_no_flag               MLRVFILYAENVHTPDTDISDAYCSAVFAGVKKRTKVIRNSVNPVWNEGFEWDLKGIPLDQGSELHVVVKDHETMGRNRFLGEAKVPLREVLATPSLSAS
430_no_flag               MLRVFILYAENVHTPDTDISDAYCSAVFAGVKKRTKVIRNSVNPVWNEGFEWDLKGIPLDQGSELHVVVKDHETMGRNRFLGEAKVPLREVLATPSLSAS
342_no_flag               MLRVFILYAENVHTPDTDISDAYCSAVFAGVKKRTKVIRNSVNPVWNEGFEWDLKGIPLDQGSELHVVVKDHETMGRNRFLGEAKVPLREVLATPSLSAS
425_no_flag               MLRVFILYAENVHTPDTDISDAYCSAVFAGVKKRTKVIRNSVNPVWNEGFEWDLKGIPLDQGSELHVVVKDHETMGRNRFLGEAKVPLREVLATPSLSAS 110       120       130       140       150       160       170       180       190       200
                                   |         |         |         |         |         |         |         |         |         |
full Length dysferlin     FNAPLLDTKKQPTGASLVLQVSYTPLPGAVPLFPPPTPLEPSPTLPDLDVVADTGEEDTEDQGLTGDEAEPFLDQSGGPAPTPPRKLPSRPPHYPGI
318                       FNAPLLDTKKQPTGASLVLQVSYT----------------------DLDVVADTG-EEDTEDQGLT-----PFLDQSGGP-----GI
431_no_flag               FNAPLLDTKKQPTGASLVLQVSYTPLPGAVPLFPPPTPLEPSPTLPDLDVVADTGEEDTEDQGLTGDEAEPFLDQSGGPAPTPPRKLPSRPPHYPGI
430_no_flag               FNAPLLDTKKQPTGASLVLQVSYTPLPGAVPLFPPPTPLEPSPTLPDLDVVADTGEEDTEDQGLTGDEAEPFLDQSGGPAPTPPRKLPSR-----GI
342_no_flag               FNAPLLDTKKQPTGASLVLQVSYTPLPGAVPLFPPPTPLEPSPTLPDLDVVADTGEEDTEDQGLTGDEAEPFLDQSGGPAPTPPRKLPSRPPHYPGI
425_no_flag               FNAPLLDTKKQPTGASLVLQVSYTPLPGAVPLFPPPTPLEPSPTLPDLDVVADTGEEDTEDQGLTGDEAEPFLDQSGGPAPTPPRKLPSRPPHYPGI 210       220       230       240       250       260       270       280       290       300
                                   |         |         |         |         |         |         |         |         |         |
full Length dysferlin     KRKRSAPTSRKLLSDKPQDFQIRVQVIEGRQLPGVNIKPVVRVTAAGQTKRTRIHRGNSPLFNETLFFNLFDSPGELFDEPIFITVVDSRLRTDALLGE
318                       KRKRS---------------IRVQVIEGRQLPGVNIKPVVRVTAAGQTKRTRIHRGNSPLFNETLFFNLFDSPGELFDEPIFITVVDSRLRTDALLGE
431_no_flag               KRKRSAPTSRKLLSDKPQDFQIRVQVIEGRQLPGVNIKPVVRVTAAGQTKRTRIHRGNSPLFNETLFFNLFDSPGELFDEPIFITVVDSRLRTDALLGE
430_no_flag               KRKRSAPTSRKLLSDKPQ-----------------------------------------------------------------------------
342_no_flag               KRKRSAPTSRKLLSDKPQ-----------------------------------------------------------------------------
425_no_flag               KRKRSAPTSRKLLSDKPQDFQIRVQVIEGRQLPGVNIKPVVRVTAAGQTKRTRIHRGNSPLFNETLFFNLFDSPGELFDEPIFITVVDSRLRTDALLGE 310       320       330       340       350       360       370       380       390       400
                                   |         |         |         |         |         |         |         |         |         |
full Length dysferlin     FRMDVGTIYREPRHAYLRKWLLLDSPDDFSAGARGYLKTSLCVLGPGDEAPLERKDPSEDKEDIESNLLRPTGVALRGAHFCLRVFRAEDLPQHDDAVMD
318                       FRMDVGTIYREPRHAYLRKWLLLDSPDDFSAGARGYLKTSLCVLGPGDEAPLERKDPSEDKEDIESNLLRPTGVALRGAHFCLRVFRAEDLPQHDDAVMD
431_no_flag               FRMDVGTIYREPRHAYLRKWLLLDSPDDFSAGARGYLKTSLCVLGPGDEAPLERKDPSEDKEDIESNLLRPTGVALRGAHFCLRVFRAEDLPQHDDAVMD
430_no_flag               ------------------------------------------------PSEDKEDIESNLLRPTGVALRGAHFCLRVFRAEDLPQHDDAVMD
342_no_flag               ---------------------------------------------------SNLLRPTGVALRGAHFCLRVFRAEDLPQHDDAVMD
425_no_flag               FRMDVGTIYREPRHAYLRKWLLLDSPDDFSAGARGYLKTSLCVLGPGDEAPLERKDPSEDKEDIESNLLRPTGVALRGAHFCLRVFRAEDLPQHDDAVMD 410       420       430       440       450       460       470       480       490       500
                                   |         |         |         |         |         |         |         |         |         |
full Length dysferlin     NVRQIFGFESNKKNLVDPFVEVSFAGKMLCSKILEKTANPQMNQNITLPAMFPSMCEKMRIRIIDWDRLTHNDIVATTYLSMSKISAPGGEIEEEPAGAV
318                       NVRQIFGFESNKKNLVDPFVEVSFAGKMLCSKILEKTANPQMNQNITLPAMFPSMCEKMRIRIIDWDRLTHNDIVATTYLSMSKISAPGGEIEEEPAGAV
431_no_flag               NVRQIFGFESNKKNLVDPFVEVSFAGKMLCSKILEKTANPQMNQNITLPAMFPSMCEKMRIRIIDWDRLTHNDIVATTYLSMSKISAPGGEIEEEPAGAV
430_no_flag               NVRQIFGFESNKKNLVDPFVEVSFAGKMLCSKILEKTANPQMNQNITLPAMFPSMCEKMRIRIIDWDRLTHNDIVATTYLSMSKISAPGGEIEEEPAGAV
342_no_flag               NVRQIFGFESNKKNLVDPFVEVSFAGKMLCSKILEKTANPQMNQNITLPAMFPSMCEKMRIRIIDWDRLTHNDIVATTYLSMSKISAPGGEIEEEPAGAV
425_no_flag               NVRQIFGFESNKKNLVDPFVEVSFAGKMLCSKILEKTANPQMNQNITLPAMFPSMCEKMRIRIIDWDRLTHNDIVATTYLSMSKISAPGGEIEEEPAGAV 510       520       530       540       550       560       570       580       590       600
                                   |         |         |         |         |         |         |         |         |         |
full Length dysferlin     KPSKASDLDDYLGFLPFTFGPCYINLYGSPREFTGFPDYTELNTGKGEGVAYRGRLLLSLETKLVEHSEQKVEDLPADDILRVERYLRRKYSLFAAFYS
310                       KPSKASDLDDYLGFL--------------------------------------------------EHSEQKVEDLPADDILRVERYLRRKYSLFAAFYS
```

TABLE 3-continued (SEQ ID NOS: 11, 6, 7, 8, 9, 10, respectively)

```
                      610       620       630       640       650       660       670       680       690       700
                        |         |         |         |         |         |         |         |         |         |
431_no_flag           KPSKASDLDDYLGFLPTFGPCYINLYGSPREFTGFPDPYTELNTGKGEGVAYRGRLLLSLETKLVEHSEQKVEDLPADDILRVERYLRRRKYSLFAAFYS
430_no_flag           KPSKASDLDDYLGFLPTFGPCYINLYGSPREFTGFPDPYTELNTGKGEGVAYRGRLLLSLETKLVEHSEQKVEDLPADDILRVERYLRRRKYSLFAAFYS
342_no_flag           KPSKASDLDDYLGFLPTFGPCYINLYGSPREFTGFPDPYTELNTGKGEGVAYRGRLLLSLETKLVEHSEQKVEDLPADDILRVERYLRRRKYSLFAAFYS
425_no_flag           KPSKASDLDDYLGFLPTFGPCYINLYGSPREFTGFPDPYTELNTGKGEGVAYRGRLLLSLETKLVEHSEQKVEDLPADDILRVERYLRRRKYSLFAAFYS 710       720       730       740       750       760       770       780       790       800
                        |         |         |         |         |         |         |         |         |         |
full Length dysferlin ATMLQDVDDAIQFEVSIGNYNYCGHYYYLPWGNVRPVVVLSSYWEDISHRIETQNQLLGIADRLEAGLEQVHLALKAQC
318
431_no_flag           ATMLQDVDDAIQFEVSIGN---------------------------------HRIETQNQLLGIADRLEAGLEQVHLALKAQC
430_no_flag           ATMLQDVDDAIQFEVSIGNYNYCGHYYYLPWGNVRPVVVLSSYWEDISHRIETQNQLLGIADRLEAGLEQVHLALKAQC
342_no_flag           ATMLQDVDDAIQFEVSIGNYNYCGHYYYLPWGNVRPVVVLSSYWEDISHRIETQNQLLGIADRLEAGLEQVHLALKAQC
425_no_flag           ATMLQDVDDAIQFEVSIGNYNYCGHYYYLPWGNVRPVVVLSSYWEDISHRIETQNQLLGIADRLEAGLEQVHLALKAQC 810       820       830       840       850       860       870       880       890       900
                        |         |         |         |         |         |         |         |         |         |
full Length dysferlin STEDVDSLVAQLTDELTAGCSQPLGDIHETPSATHLDQYLYQLRTHHLSQITEAALALKLGHSELPAALEQAEDWLLRLRALAEEPQNSLPDIVWMLQG
318
431_no_flag           STEDVDSLVAQLTDELTAGCSQPLGDIHETPSATHLDQYLYQLRTHHLSQITEAALALKLGHSELPAALEQAEDWLLRLRAL-----------------
430_no_flag           STEDVDSLVAQLTDELTAGCSQPLGDIHETPSATHLDQYLYQLRTHHLSQITEAALALKLGHSELPAALEQAEDWLLRLRALAEEPQNSLPDIVWMLQG
342_no_flag           STEDVDSLVAQLTDELTAGCSQPLGDIHETPSATHLDQYLYQLRTHHLSQITEAALALKLGHSELPAALEQAEDWLLRLRALAEEPQNSLPDIVWMLQG
425_no_flag           STEDVDSLVAQLTDELTAGCSQPLGDIHETPSATHLDQYLYQLRTHHLSQITEAALALKLGHSELPAALEQAEDWLLRLRALAEEPQNSLPDIVWMLQG 910       920       930       940       950       960       970       980       990       1000
                        |         |         |         |         |         |         |         |         |         |
full Length dysferlin DKRVAYQRVPAHQVLFSRRGANYCGKNCGKLQTIFLKYPMERVPGARMPVQIRVKLMFGLSVDEKEFNQFAEGKLSVFAETYENETKLALVGNWGTTGLT
318
431_no_flag           --------------------------------KLQTIFLKYPMERVPGARMPVQIRVKLMFGLSVDEKEFNQFAEGKLSVFAETYENETKLALVGNWGTTGLT
430_no_flag           DKRVAYQRVPAHQVLFSRRGANYCGKNCGKLQTIFLKYPMERVPGARMPVQIRVKLMFGLSVDEKEFNQFAEGKLSVFAETYENETKLALVGNWGTTGLT
342_no_flag           DKRVAYQRVPAHQVLFSRRGANYCGKNCGKLQTIFLKYPMERVPGARMPVQIRVKLMFGLSVDEKEFNQFAEGKLSVFAETYENETKLALVGNWGTTGLT
425_no_flag           DKRVAYQRVPAHQVLFSRRGANYCGKNCGKLQTIFLKYPMERVPGARMPVQIRVKLMFGLSVDEKEFNQFAEGKLSVFAETYENETKLALVGNWGTTGLT 1010      1020      1030      1040      1050      1060      1070      1080      1090      1100
                        |         |         |         |         |         |         |         |         |         |
full Length dysferlin YPKFSDVTGKIKLPKDSFRPSAGWTWAGDWFVCPEKTLLHDNDAGHLSFVEEVFENQTRLPGGQWIYMSDNYTDVRGEKVLPKDDIECPLGWRWEDEEWS
318
431_no_flag           YPKFSDVTGKIKLPKDSFRPSAGWTWAGDWFVCPEKTLLHDNDAGHLSFVEEVFENQTRLPGGQWIYMSDNYTDVRGEKVLPKDDIECPLGWRWEDEEWS
430_no_flag           -------------------------------NDAGHLSFVEEVFENQTRLPGGQWIYMSDNYTDVRGEKVLPKDDIECPLGWRWEDEEWS
342_no_flag           YPKFSDVTGKIKLPKDSFRPSAGWTWAGDWFVCPEKTLLHDNDAGHLSFVEEVFENQTRLPGGQWIYMSDNYTDVRGEKVLPKDDIECPLGWRWEDEEWS
425_no_flag           YPKFSDVTGKIKLPKDSFRPSAGWTWAGDWFVCPEKTLLHDNDAGHLSFVEEVFENQTRLPGGQWIYMSDNYTDVRGEKVLPKDDIECPLGWRWEDEEWS full Length dysferlin TDLNRAVDEQGWEYSITIPPERKPKHWVPAEKMYYTHRRRRWVRLRRRDLSQMEALKRHRQAEAEGEWEYASLFGWKFHLEYRKTDAFRRRRWRRRMEP
318
431_no_flag           TDLNRAVDEQGWEYSITIPPERKPKHWVPAEKMYYTHRRRRWVRLRRRDLSQMEALKRHRQAEAEGEWEYASLFGWKFHLEYRKTDAFRRRRWRRRMEP
430_no_flag           TDLNRAVDEQGWEYSITIPPERKPKHWVPAEKMYYTHRRRRWVRLRRRDLSQMEALKRHRQAEAEGEWEYASLFGWKFHLEYRKTDAFRRRRWRRRMEP
342_no_flag           TDLNRAVDEQGWEYSITIPPERKPKHWVPAEKMYYTHRRRRWVRLRRRDLSQMEALKRHRQAEAEGEWEYASLFGWKFHLEYRKTDAFRRRRWRRRMEP
425_no_flag           TDLNRAVDEQGWEYSITIPPERKPKHWVPAEKMYYTHRRRRWVRLRRRDLSQMEALKRHRQAEAEGEWEYASLFGWKFHLEYRKTDAFRRRRWRRRMEP
```

TABLE 3-continued (SEQ ID NOS: 11, 6, 7, 8, 9, 10, respectively)

```
                        1110       1120       1130       1140       1150       1160       1170       1180       1190       1200
                        ....|....|....|....|....|....|....|....|....|....|....|....|....|....|....|....|....|....|....|....|
full length dysferlin   LEKTGPAAVFALEGALGGVMDDKSEDSMSVSTLSFGVNRPTISCIFDYGNRPYHLRCYMYQARDLAAMDKSFSDPYAIVSFLHQSQKTVVKNTLNPTWD
318                     LEKT------------------------------------------------------------------------------------------------
431_no_flag             LEKTGPAAVFALEGALGGVMDDKSEDSMSVSTLSFG-----------------------------------------------------------------
430_no_flag             LEKTGPAAVFALEGALGGVMDDKSEDSMSVSTLSFG-----------------------------------------------------------------
342_no_flag             LEKTGPAAVFALEGALGGVMDDKSEDSMSVSTLSFG-----------------------------------------------------------------
```

Example 2

In Vivo Effect of Truncated Dysferlin

Previous attempts at constructing smaller dysferlin genes have discounted the fact that partially folded protein domains, as a result of inappropriate truncation, could mask any therapeutic value of the smaller gene. To alleviate this issue, careful attention was given to the structural characteristics of C2 domains in order to rationally define each domain of dysferlin. Each of the seven C2 domains in dysferlin was defined by eight predicted b strands, C2 domain topology, integrity of the $Ca^{2+}$-binding site, if applicable, and continuity of the hydrophobic packing in the core of the domain (Table 2). The overall philosophy to construct Nano-Dysferlin is based on three rules. First, the central features of the ferlin family members, FerA and DysF, were maintained intact in all constructs. Second, the first C2A domain and the C2 domain next to the transmembrane span, C2G, were preserved in all constructs. Third, multiple tandem C2 domains contribute individually to the overall membrane avidity. Given these tenants, C2 domains were subsequently excised with knowledge of the folded domain and the flexible linker that joined it to other potentially folded domains. These three rules led to the construction of a compact, potentially therapeutic dysferlin variant (Nano-Dysferlin (clone 425)), which was predicted to be efficiently packaged within a single AAV capsid (open reading frame [ORF] 4,356 nt).

Expression of Nano-Dysferlin in Mammalian Cells

Figure 1B:
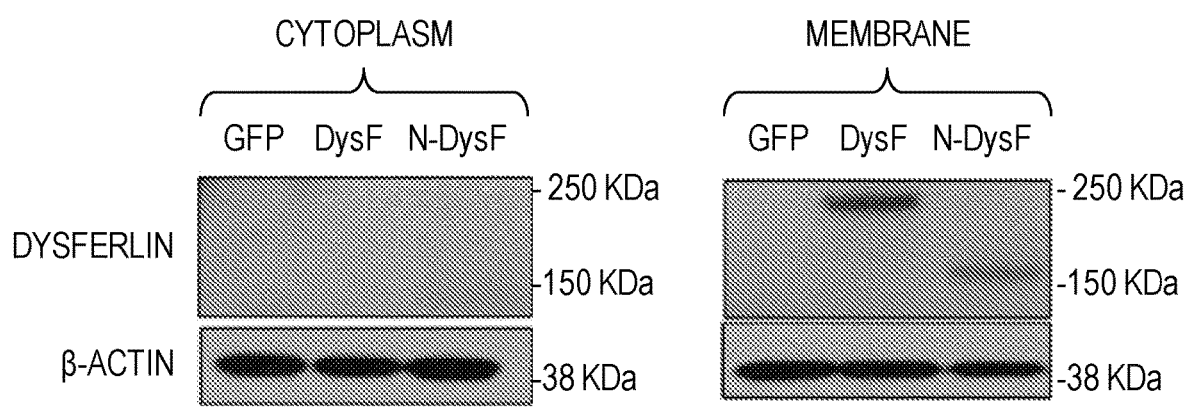
Figure 1C:
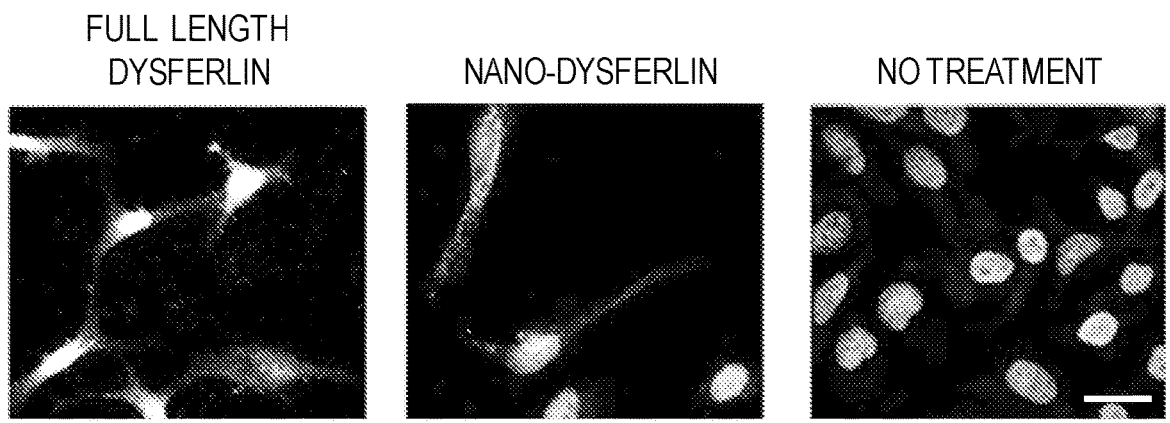
Figure 1D:
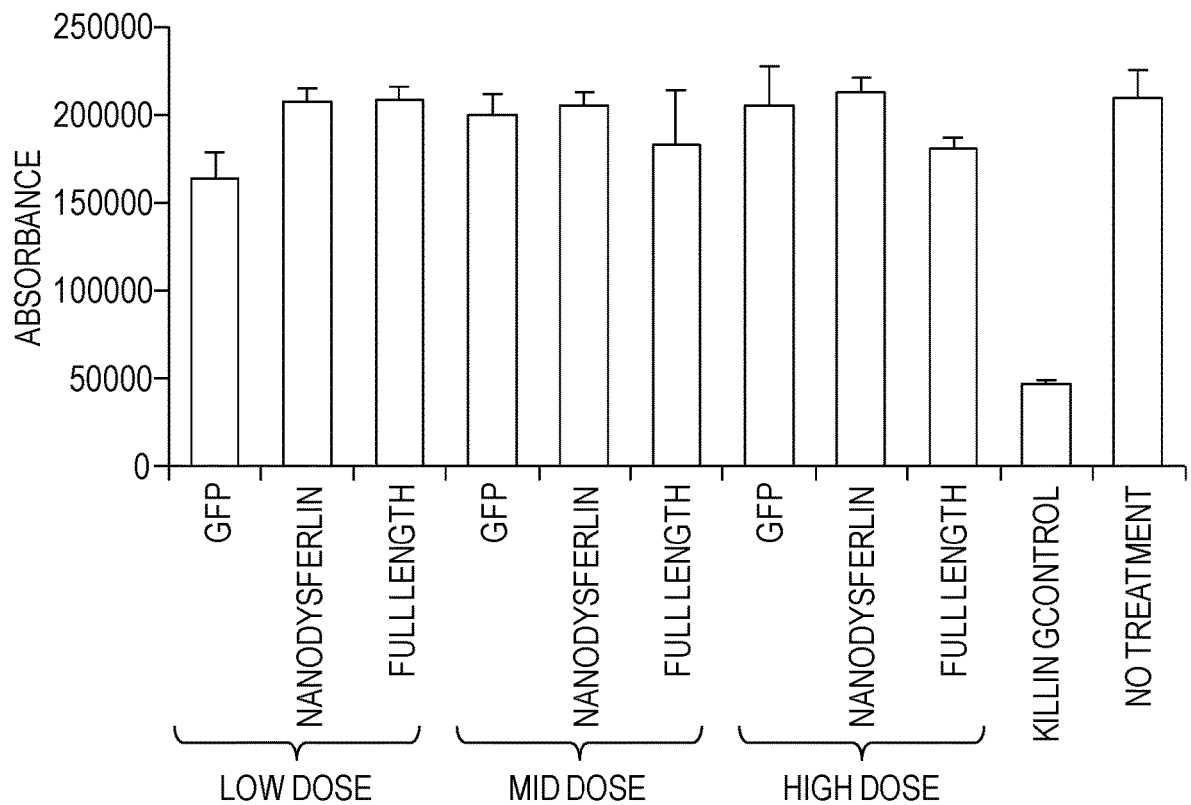

Nano-Dysferlin was based on the wild-type (WT) dysferlin isoform 8 cDNA (6,240 nt), which contains domains C2A-C2B-C2C-FerADysF-C2D-C2E-C2F-C2G-TM (FIG. 1A). Initially, western blotting of membrane-associated, or soluble, protein lysates was performed to determine Nano-Dysferlin localization following transfection in C2C12 myoblasts. For these experiments, full-length dysferlin and GFP expression cassettes served as the positive and negative controls, respectively. The results demonstrate that Nano-Dysferlin is produced as a single band at its expected size (160 kDa), and, like its parent molecule dysferlin, Nano-Dysferlin is a membrane and membrane vesicle-associated protein (FIG. 1B). Immunofluorescence of Nano-Dysferlin in transfected human HeLa cells demonstrated similar protein localization and abundance like wild-type dysferlin, with both distributed throughout the cell, likely in membrane vesicles, as it has been previously reported (Han et al., *J. Clin. Invest.* 117:1805 (2007); Bansa et al. *Nature* 423:168 (2003)) (FIG. 1C). In vitro toxicity experiments in dysferlin patient myoblasts showed no toxicity by alamar Blue following Nano-Dysferlin or dysferlin overexpression at increasing transfection doses of plasmid DNA (FIG. 1D).

Figure 2A:
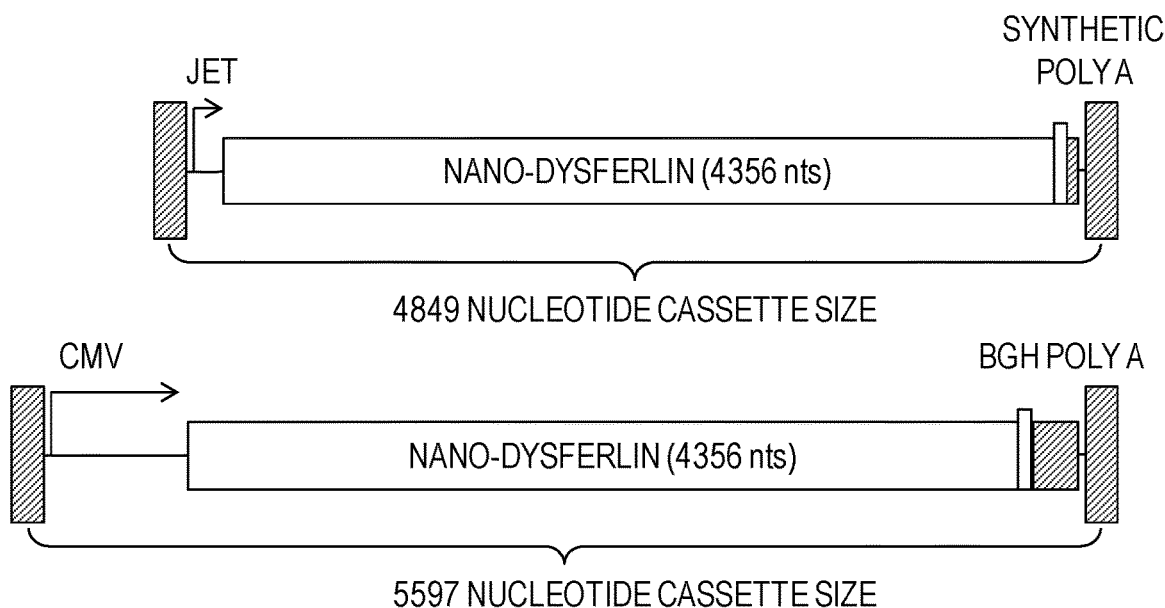
FIGS. 2A-2D show intact AAV transduction using a weak promoter is more efficient than fragment AAV using a strong promoter.
Figure 2B:
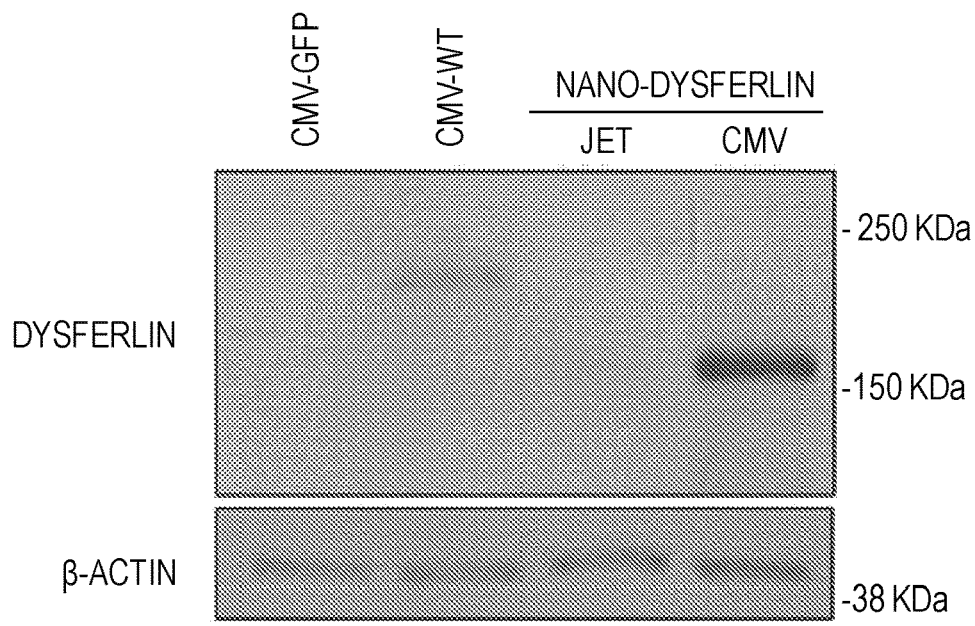
Figure 2C:
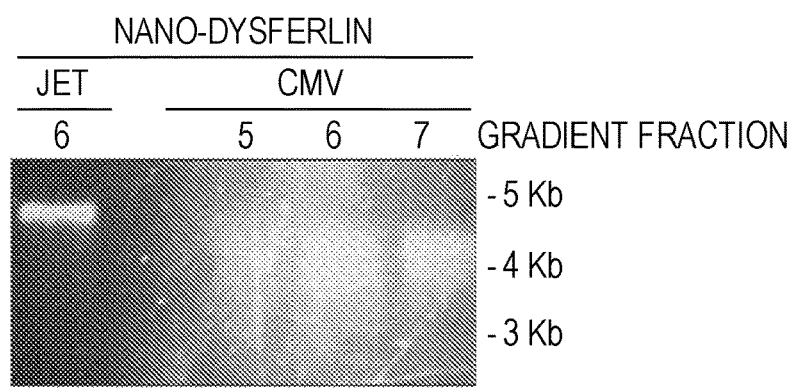
Figure 2D:
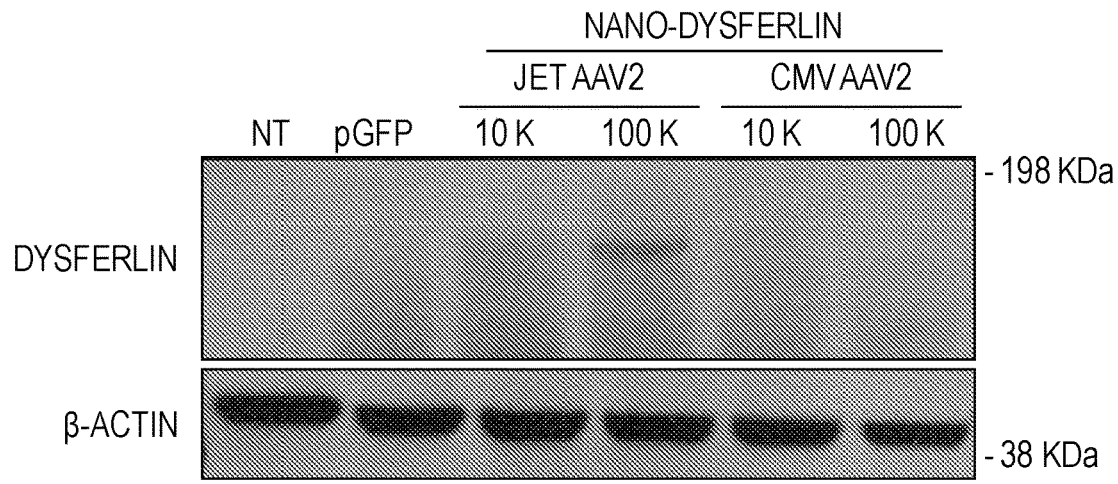

Intact AAV Transduction Using a Weak Promoter is More Efficient than Fragment AAV Using a Strong Promoter To find the most efficient therapy for in vivo studies, fragment AAV with a strong CMV promoter was evaluated against intact AAV with a small weak JeT promoter for Nano-Dysferlin protein production. CMV-Nano-Dysferlin has a cassette size of 5,597 nt, whereas JeT Nano-Dysferlin is theoretically within the AAV capsid packaging capacity at 4,849 nt (Tornoe et al., *Gene* 297:21 (2002)) (FIG. 2A). To determine Nano-Dysferlin protein production from each cassette in a plasmid context, western blotting was performed following HEK293 cell transfection. As expected, the larger CMV promoter produced approximately 15-fold more Nano-Dysferlin compared to the small JeT promoter (Torne et al., *Gene* 297:21 (2002)) (FIG. 2B). Given the existing AAV packaging dogma, it was hypothesized that the CMV-Nano-Dysferlin cassette at 5.6 kb would produce fragment AAV, whereas the smaller JeT cassette could be packaged as an intact genome at 4.85 kb in the AAV2 capsid. To investigate this, the capsid-packaged DNA species were separated by alkaline gel electrophoresis and then stained with SYBR gold. A single DNA species of the intended size was observed for the smaller JeT driven cassette, whereas Nano-Dysferlin expressed from the larger CMV promoter resulted in the packaging of heterogeneous DNA species within the size range of approximately 3.5-4.5 kb, much smaller than the intended 5.6-kb genome (FIG. 2C). The efficiency of fragment AAV transduction compared to intact AAV is dramatically decreased between 5- and 100-fold (Hirsch et al., *Mol. Ther.* 21:2205 (2013); Hirsch et al., *PLoS ONE* 4:e7705 (2009)). To determine if the CMV promoter, which is much stronger that the JeT promoter (FIG. 2B), can overcome the decreased efficiency of fragment AAV, Nano-Dysferlin abundance was determined by western blot following transduction at increasing doses. Despite the differences in promoter strength favoring CMV, intact AAV2-JeT-Nano-Dysferlin vector transduction showed superior protein production compared to fragment AAV2-CMV-Nano-Dysferlin when administered at increasing doses (FIG. 2D). Given the defined nature of the packaged transgenic DNA (FIG. 2C), increased efficiency of intact AAV vector transduction (FIG. 2D), envisioned systemic clinical intravenous (IV) administration, and potential for an unwanted immunological response to the vector at high doses in the clinic, the higher efficiency intact JeT-Nano-Dysferlin-based vector was selected for the remaining in vivo studies.

AAV-Nano-Dysferlin Improves Muscle Integrity Following Intramuscular Injection Next, the safety and efficacy of AAV-Nano-Dysferlin was investigated in blinded experiments following intramuscular injections using the AAV1 capsid due to its ability for widespread muscle transduction. The TAs of 6-week-old dysferlin-deficient (BLA/J) mice were injected with AAV1-JeT-Nano-Dysferlin, with the contralateral leg receiving AAV1-CMV-GFP as a control. 40 hr before sacrifice, at 9 weeks, mice were injected intraperitoneally with Evans blue dye, a muscle damage marker that binds intra-fiber albumin, helping detect breaches in the sarcolemma of damaged muscle fibers (Matsuda et al., *J. Biochem.* 118:959 (1995)). Upon counting positive fibers normalized to total fibers in cross-sections, variability in Evans blue dye-positive fibers in the AAV1-GFP control muscles was observed between individual BLA/J mice, suggesting different disease severities in genetically identical mice (FIG. 3A, "GFP"). This is consistent with early disease variability in human dysferlinopathy patients, as previously reported (Nguyen et al., *Hum. Mutat.* 26:165 (2005)). Despite baseline variations between TAs treated with control vector between the mice, within each mouse, every muscle treated with AAV1-JeT-Nano-Dysferlin demonstrated fewer Evans blue dye-positive fibers compared to the respective contralateral GFP control (FIG. 3A). Collectively, the mouse cohort showed a significant difference between treated and control muscles by a paired two-tailed t test, p=0.005 (FIG. 3A). Central nucleation, a marker for muscle regeneration and thus indirectly muscle fiber turnover, was quantitated upon H&E staining of sections. The data indicate a decrease in central nucleation in all but one TA muscle injected with AAV1-Jet-Nano-Dysferlin compared to the internal AAV1-GFP control (FIG. 3B; two-tailed t test, p=0.0125). AAV-treated muscles also showed visibly improved histology (FIG. 3C). Immunofluorescence detected Nano-Dysferlin in approximately 30% of muscle fibers; however, its localization in each muscle fiber was more distributed compared to the sarcolemma predominance observed for endogenous dysferlin. This is a common, yet puzzling, observation consistently reported for dysferlin gene addition studies in dysferlin-deficient mice (Lostal et al., *Hum. Mol. Genet.* 19:1897 (2010); Sondergaard et al., *Ann. Clin. Transl. Neurol.* 2:256 (2015); Grose et al., *WPLoS ONE* 7:e39233 (2012)) (FIG. 3D).

AAV-Nano-Dysferlin Improves Motor Function Following Systemic Injection

Figure 4A:
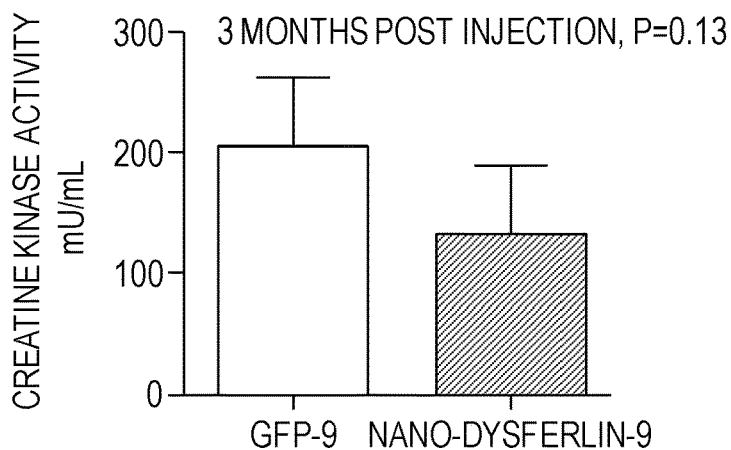
FIGS. 4A-4C show AAV-Nano-Dysferlin improves motor function following systemic injection.
Figure 4B:
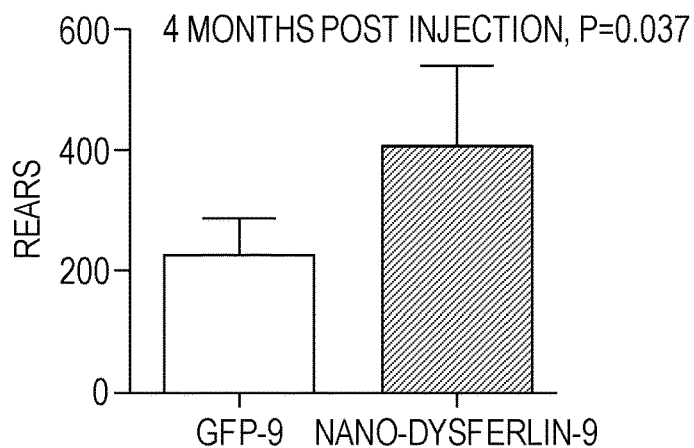
Figure 4C:
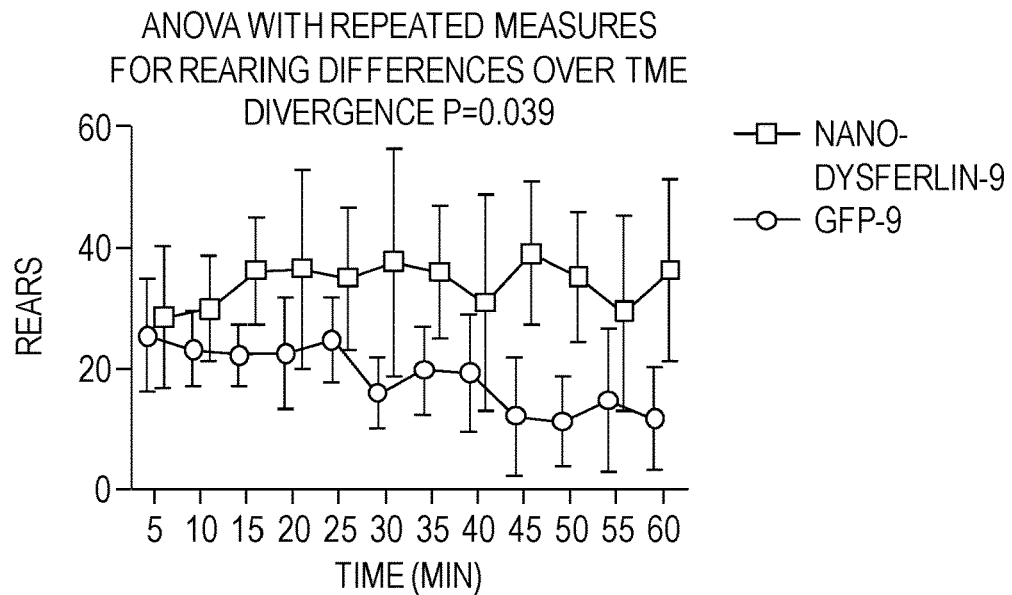

The BLA/J mouse model of dysferlinopathy varies from the human condition with only mild motor deficits that significantly manifest, depending on the motor challenge and sensitivity of acquisition, at approximately 12 months of age (Nagy et al., *Physiol. Rep.* 5:e13173 (2017)). Consistently, human dysferlinopathy becomes evident normally after 12 years of age with normal, or even enhanced, athleticism earlier in life. In attempts to mimic the timing of diagnosis and the subsequent human therapeutic window of treatment, BLA/J mice were treated systemically with AAV9-JeT-NanoDysferlin (n=6) or an AAV9-CMV-GFP control vector (n=4), with a dose of $1e^{11}$ viral genomes. Blood creatine kinase activity, a marker often elevated in muscular dystrophies (Cabaniss (1990). Creatine kinase. In *Clinical Methods: The History*, Third Edition, H. K. Walker, W. D. Hall, and J. W. Hurst, eds. (Butterworths)), was measured at 39 weeks, with the AAV9-Nano-Dysferlin cohort, showing a non-significant, yet trending, decrease by an unpaired t test with Welch's correction (p=0.13) (FIG. 4A). Based on previous findings of reduced rearing, the ability to stand on the two hind legs with arms/head in the air, over time in older BLA/J mice, this cohort's rearing activity was observed at 43 weeks of age, roughly 5 and a half months postinjection (Nagy et al., *Physiol. Rep.* 5:e13173 (2017)). The data demonstrate a significant increase in total rears, on average >200 more times within an hour, only in mice that received AAV9-JeT-Nano-Dysferlin by a t test with Welch's correction (p=0.037) (FIG. 4B). Furthermore, analysis of rearing performance over time suggested AAV9-Jet-Nano-Dysferlin-injected mice were not fatigued and maintained rearing at a constant level, whereas the performance of AAV9-CMV-GFP-injected mice decreased over time when analyzed by an ANOVA with repeated measures (p=0.039) (FIG. 4C). Horizontal activity showed no differences over the first 30 min (p=0.58); however, over the last 30 min of evaluation, a non-significant (p=0.13), yet trending, higher horizontal activity was observed in Nano-Dysferlin-treated mice by t test. This propensity to early "fatigue" has been observed in a BLA/J dysferlinopathy mouse model when compared to C56B7 mice (Nagy et al., *Physiol. Rep.* 5:e13173 (2017)).

AAV-Nano-Dysferlin Improves Muscle Integrity Following Systemic Injection

Figure 5A:
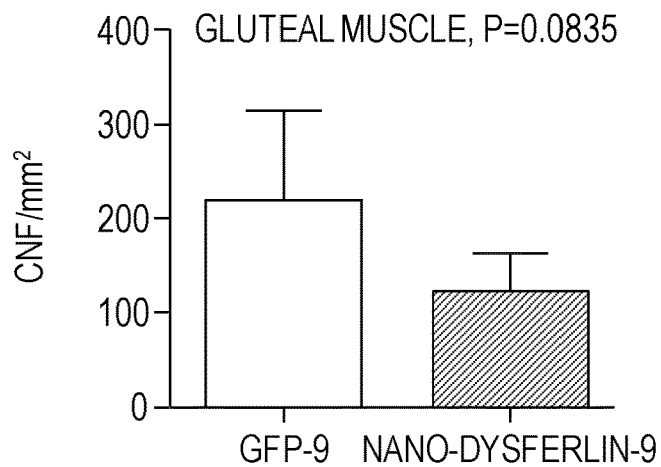
FIGS. 5A-5E show the effect of AAV-Nano-Dysferlin on muscle histology following systemic injection.
Figure 5B:
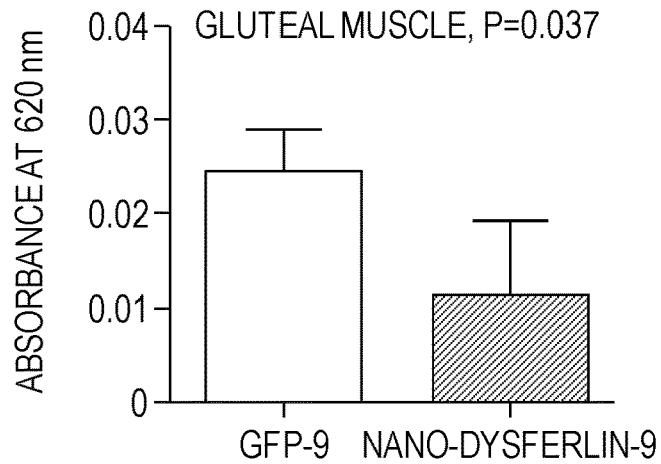
Figure 5D:
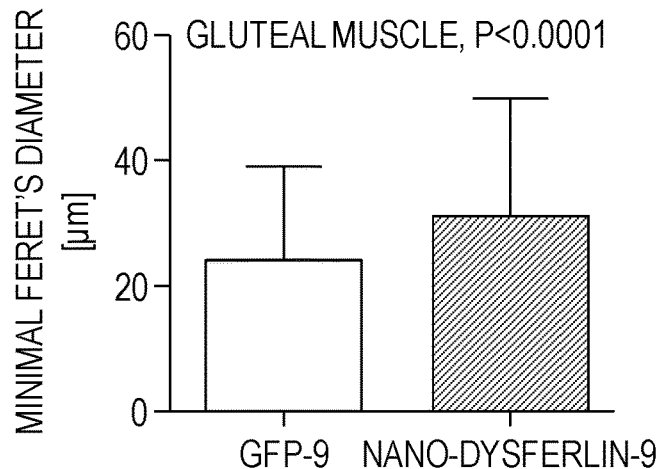
Figure 5C:
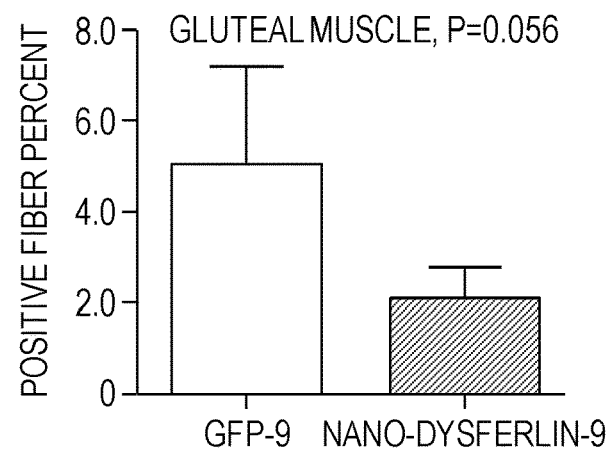
Figure 5C:
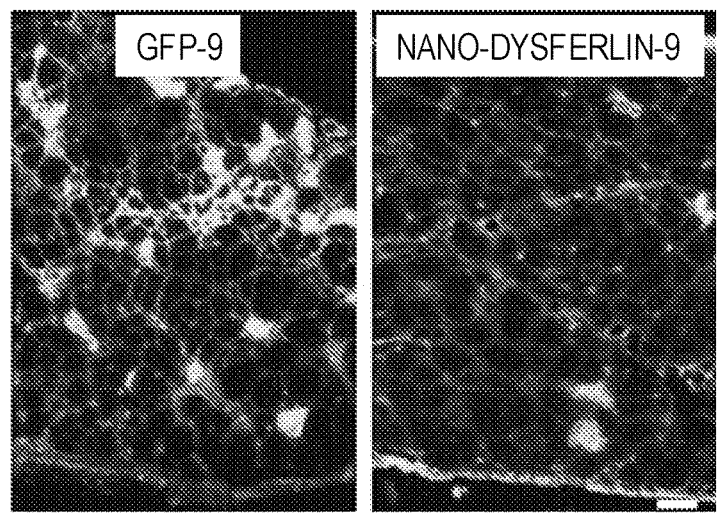
Figure 6A:
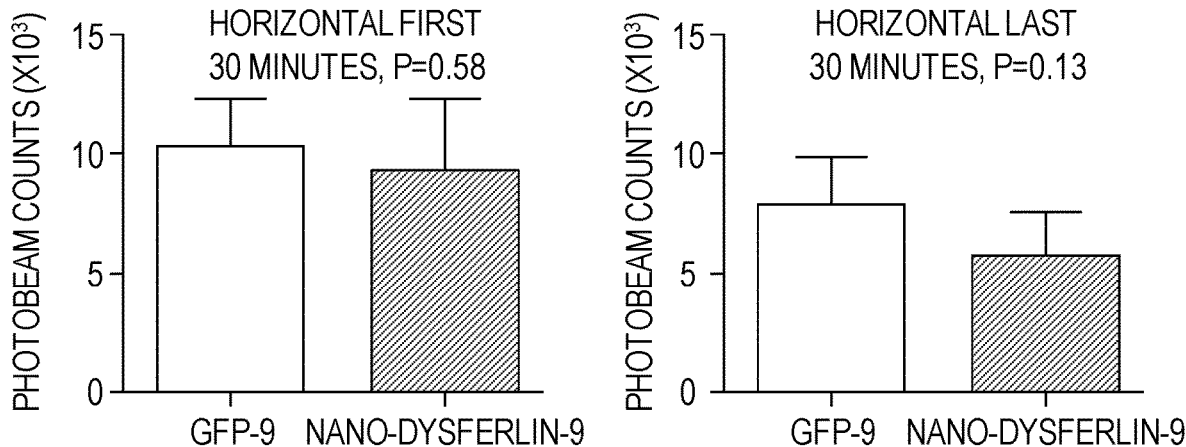
FIGS. 6A-6C show additional data.
Figure 6B:
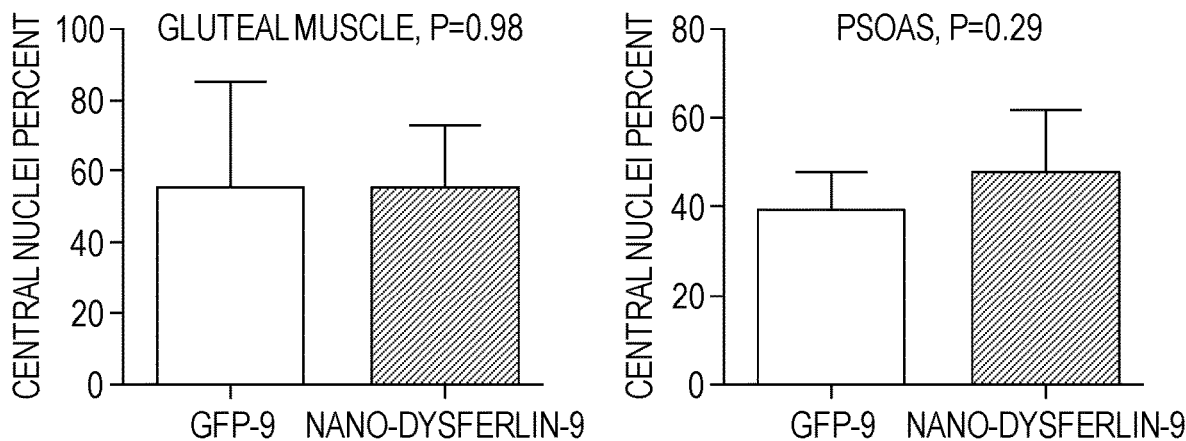
Figure 6C:
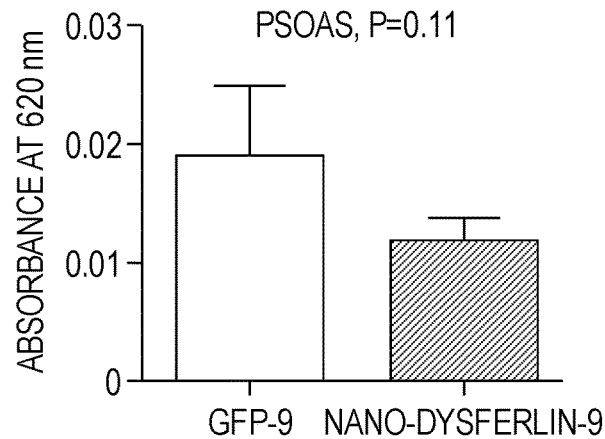
Figure 7:
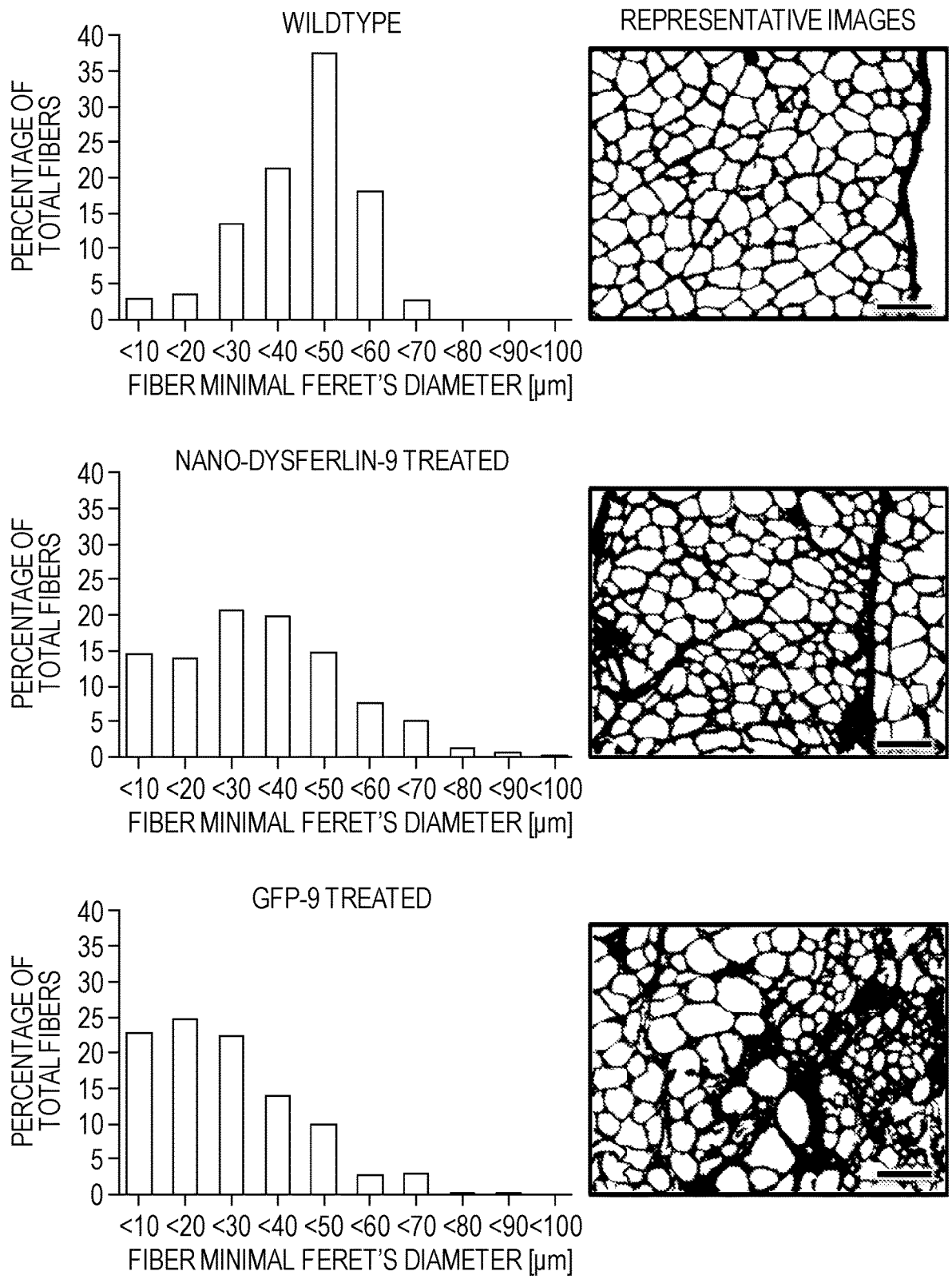
FIG. 7 shows fiber size distribution. Minimum Feret's Diameter, an artifact resilient measure of muscle fiber size was performed on WGA lectin labeled Gluteus Maximus muscle sections run through an ImageJ protocol. Nano-Dysferlin treated mice fiber size distributions (n=610) showed larger fiber sizes than GFP treated mice fiber size distributions (n=619), showing partial correction compared to wild-type untreated distributions (n=467). Total sums in range shown. Scale Bar=100 μm.
Figure 8:
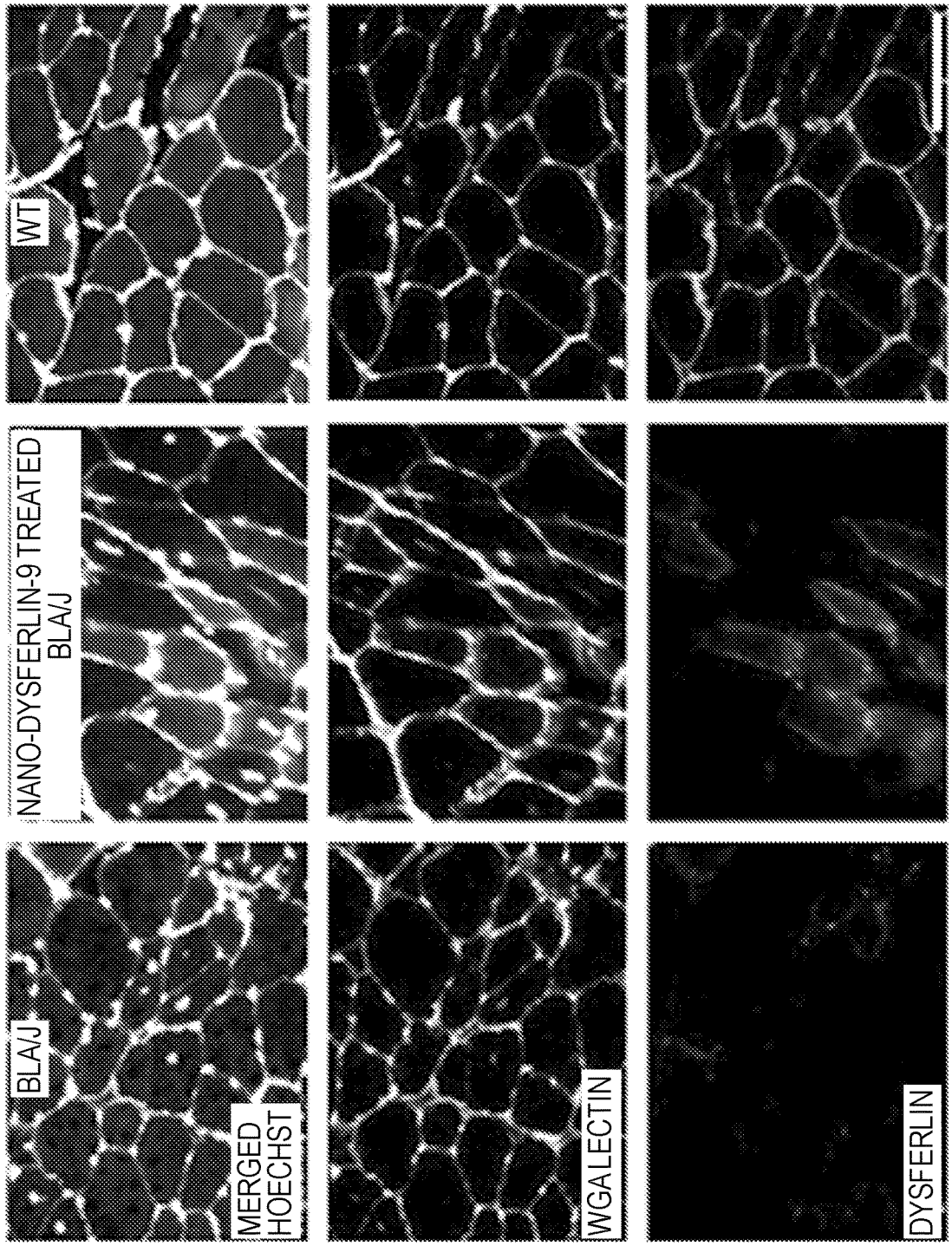
FIG. 8 shows Nano-Dysferlin detection by immunofluorescence. Immunofluorescence staining of gluteal muscles from the indicated mice with a dysferlin antibody, Hoechst nuclear stain, and wheat germ agglutinin membrane stain. Nano-Dysferlin localization throughout the membrane and cytoplasm was noted while endogenous dysferlin is uniquely localized to the membrane. Approximately 10% of muscle fibers stained positive for Nano-Dysferlin (total fiber n=441). Scale bar, 100 μm.
Figure 9A:
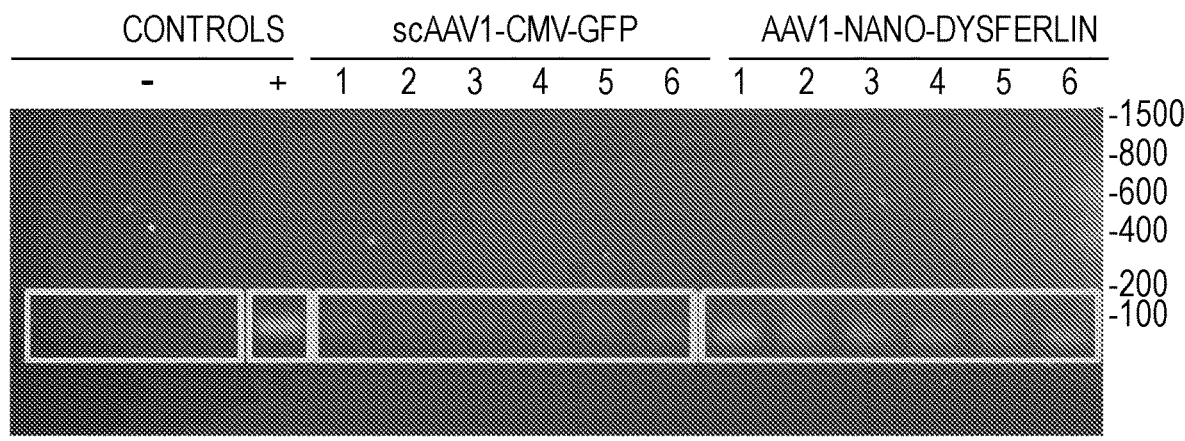
FIGS. 9A-9B show detection by RT-PCR.
Figure 9B:
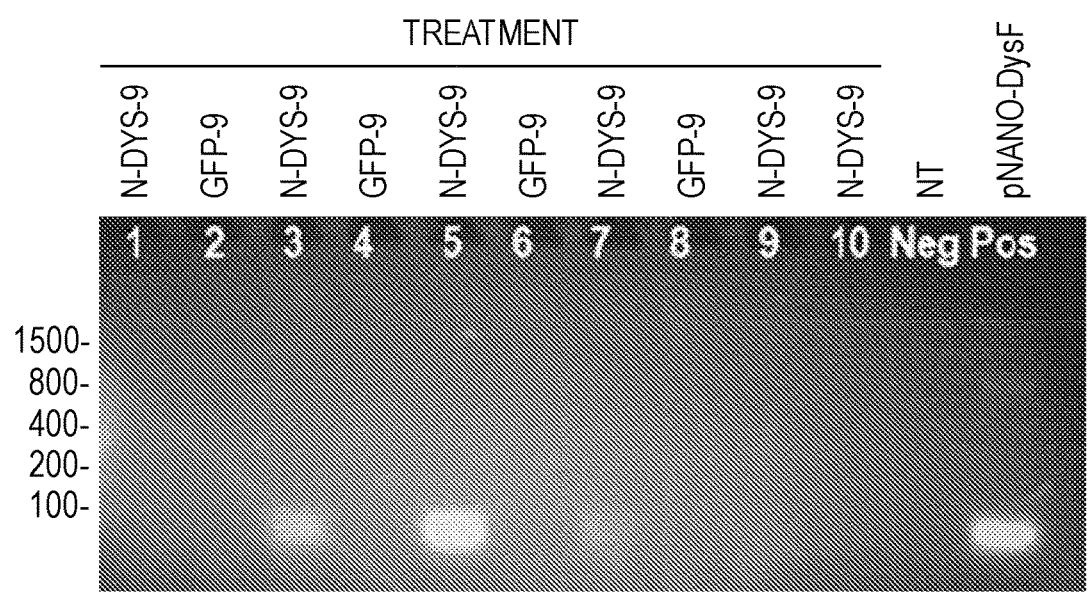

The systemically treated cohort described above for motor function was sacrificed at 54 weeks, roughly 8 months following a single injection at 4.5 months of age. Evans blue dye was administered prior to euthanasia, and dye uptake, indicative of damaged muscle, was analyzed in a whole muscle assay and separately in a fiber-by-fiber manner following histology (Matsuda et al., *J. Biochem.* 118:959 (1995)). The whole muscle Evans blue dye assay was performed using the gluteal and psoas muscles, which were determined in previous work to be the most affected in the BLA/J mouse (Nagy et al., *Physiol. Rep.* 5:e13173 (2017)). In this assay, a higher absorbance indicates increased dye uptake and more muscle damage (Matsuda et al., *J. Biochem.* 118:959 (1995)). The gluteal muscles, thought to be most affected in the BLA/J mouse model by our previous studies (Nagy et al., *Physiol. Rep.* 5:e13173 (2017)), showed significantly lower Evans blue dye uptake in mice treated with AAV9-JeT-Nano-Dysferlin compared to controls by a t test with Welch's correction (p=0.037) (FIG. 5B). Meanwhile, analysis of the psoas muscle showed a non-significant trend of reduced Evans blue dye whole muscle uptake in AAV9-JeT-Nano-Dysferlin-treated mice (n=6) compared to controls (n=4) by a t test with Welch's correction (p=0.11) (FIGS. 6A-6B). To confirm the Evans blue dye whole muscle analysis, Evans blue dye-positive fibers were directly counted following histology and normalized to total fibers, with AAV9-Jet-Nano-Dysferlin-treated muscles showing an almost significant (p=0.056) reduction of Evans blue dye-positive fibers (FIG. 5C). Central nucleated fibers, indicative of muscular regeneration and turnover, also revealed a non-significant, yet strong, trend of reduction (p=0.0835) in AAV9-Jet-Nano-Dysferlin-treated gluteal muscles (FIG. 5A). Total central nuclei/total fibers were also evaluated and non-significant differences were found between treatments (FIGS. 6A-6B). As an additional measure of muscle fiber health, gluteal muscle fiber size was measured by the minimal Feret's diameter from wheat germ agglutinin (WGA) lectin-stained muscle sections (Briguet et al., *Neuromuscul. Disord.* 14:675 (2004)), and analyzed with ImageJ. Past studies have found increased variability and decreased mean fiber size in dysferlin-null mice muscles when compared to wild-type genetic background mice (Bansal et al., *Nature* 423:168 (2003). The present results found muscle fibers from systemically treated AAV9-Jet-Nano-Dysferlin-treated mice were significantly larger than GFP-mouse-treated muscle fibers (p<0.0001) (FIG. 5D), with fiber size distribution graphs showing a right-shifted bell curve in the AAV9-Jet-Nano-dysferlin treated cohort (FIG. 7). Given the significant fatty infiltration observed in the gluteal muscles in a previous study (Nagy et al., *Physiol. Rep.* 5:e13173 (2017)), oil red staining of lipids was performed in gluteus muscle sections, observing a drastic decrease of staining, which suggested lower lipid accumulation in AAV9-Jet-NanoDysferlin-treated mice gluteal muscles. To determine the extent of Nano-Dysferlin production in the gluteal muscles resulting in improved integrity, western blots were performed; however, Nano-Dysferlin was below the limit of detection by this assay and these blots were negative. This was followed by immunofluorescent staining performed on muscle sections, and wheat germ agglutinin lectin was used to stain the muscle sarcolemma. Expression was evident in approximately 10% of muscle fibers (Nano-Dysferlin total fiber, n=256; no treatment total fiber, n=185) (FIG. 8). Nano-Dysferlin presence was also confirmed in the gluteal muscles of treated mice by RT-qPCR (FIGS. 9A-9B). Nano-Dysferlin appeared to have a preference for sarcolemma localization, with some protein apparently localized throughout the cytosol, similar to the IM injections (FIG. 3) and several prior reports (Lostal et al., *Hum. Mol. Genet.* 19:1897 (2010); Sondergaard et al., *Ann. Clin. Transl. Neurol.* 2:256 (2015); Grose et al., *WPLoS ONE* 7:e39233 (2012)).

Discussion

AAV-mediated gene therapy is currently considered a promising method to treat diseases such as Duchenne muscular dystrophy (DMD) and dysferlinopathy (Lostal et al., *Hum. Mol. Genet.* 19:1897 (2010); Sondergaard et al., *Ann. Clin. Transl. Neurol.* 2:256 (2015); Hirsch et al., *Mol. Ther.* 21:2205 (2013); Grose et al., *WPLoS ONE* 7:e39233 (2012)). However, both these musclewasting diseases highlight a primary deficiency of AAV vectors: the viral capsid is too small to package the full-length cDNA for a simple gene addition strategy (Pryadkina et al., *Mol. Ther. Methods Clin. Dev.* 2:15009 (2015)). To overcome this limitation, we and others have investigated the ability of multiple AAV capsids to deliver portions of a large gene to the nucleus, wherein the host's DNA damage response mediates the possibility for large gene reconstruction (Wu et al., *Mol. Ther.* 18:80 (2010); Hirsch et al., *Mol. Ther.* 21:2205 (2013); Dong et al., *Mol Ther.* 18:87 (2010); Lai et al., *Mol Ther.* 18:75 (2010)). Although intriguing, these DNA-repair-dependent multiple vector formats for AAV large gene delivery (Hirsch et al., *Mol Ther.* 18:6 (2010)) suffer from dramatically reduced transduction efficiency compared to a single AAV particle with an intact transgenic genome (Hirsch et al., *Mol. Ther.* 21:2205 (2013); Hirsch et al., *PLoS ONE* 4:e7705 (2009)). Unlike a single particle AAV gene addition strategy, which theoretically relies on one particle infecting a single cell, AAV oversized gene transduction is highly inefficient, especially when delivered systemically (Hirsch et al., *Mol. Ther.* 21:2205 (2013); Hirsch et al., *PLoS ONE* 4:e7705 (2009)). This is due primarily to (1) the requirement for several different vector genomes to be uncoated within a single nucleus, and (2) inefficient homology-directed repair in non-dividing cells, such as muscle fibers that are biased toward non-homologous end joining, thereby generating aberrant non-functional, and potentially immunogenic, transgene products. Due to the decreased efficiency of oversized AAV transduction approaches, higher effective doses are required (compared to single particle AAV transduction) (Hirsch et al., *Mol. Ther.* 21:2205 (2013)). In many cases, increasing the dosage of virus exacerbates the problem by producing undesired immunological complications and resulting in therapeutic failure. Additionally, the current production titers of clinical grade AAV vector preparations for other muscular diseases that require only single AAV vector transduction are a serious limitation on restricting the number of patients able to be treated. Despite these two major concerns with AAV large gene transduction, preclinical data in a dysferlin-deficient mouse have led to recruitment of dysferlinopathy patients for a phase 1 clinical trial proposing the use of AAV-oversized transduction for the treatment of dysferlinopathy (Grose et al., *WPLoS ONE* 7:e39233 (2012)). Notably, this will be the first AAV trial intentionally relying on multiple vector transduction of single cells and the capacity of the patients' DNA damage response for homology-directed repair in muscle fibers for clinical success. To provide an alternative treatment strategy to patients with dysferlinopathy, we have followed suit with the DMD community and rationally designed Nano-Dysferlin, a compact dysferlin-like open reading frame that is amenable to single AAV vector genome packaging and transduction.

In general, C2 domains are modular protein domains that can bind to the inner leaflet of phospholipid membranes (Davletov et al., *J. Biol. Chem.* 268:26386 (1993)). Most C2 domains bind to membranes in a $Ca^{2+}$-dependent manner, but there are some that do not. Wild-type dysferlin possesses seven tandem C2 domains, each separated by long linkers (Abdullah et al., *Biophys. J.* 106:382 (2014)). Our central hypothesis in constructing more compact dysferlin proteins is that multiple tandem C2 domains contribute individually to the membrane-binding avidity of the entire protein. Therefore, there must be a point where fewer domains still bind membrane and still provide their function, but can provide therapeutic benefit by being amenable to intact AAV packaging. This strategy implies a knowledge of what makes up a C2 domain. There have been other attempts at minimizing the overall size of dysferlin (Ghosh et al., *Hum. Gene Ther.* 22:77 (2011)); however, these experiments were conducted without an in-depth understanding of the structure of C2 domains. Without a clear domain definition, the folded inadvertent truncation of even a single folded domain could misfold the entire protein, thereby leading to degradation, loss of function, or even aggregation. After testing several constructs, we discovered that retaining the amino-terminal C2 domains, C2A, C2B, and C2C, with their inter-domain linkers, in addition to the FerA, DysF, C2G, and transmembrane domain results in a molecule correcting for the absence of dysferlin function in a dysferlin-deficient mouse model.

The transgenic DNA packaging limitation of AAV (<5 kb) not only precludes packaging of full-length dysferlin cDNA, but also restricted our promoter size for Nano-Dysferlin expression. Examination of packaged AAV genomes clearly demonstrated that Nano-Dysferlin expressed from the JeT promoter (4,849 nt) is packaged as a single species; in contrast, when using CMV (5,597 nt), heterogeneous DNA species were encapsidated, which ranged in size from 3 to 5 kb (Tornoe et al., *Gene* 297:21 (2002)) (FIG. 2C). This fragment AAV vector was less efficient than AAV single vector transduction, even despite the >10-fold increased expression of the CMV promoter when compared to the JeT promoter (FIGS. 2B and 2D).

In previous experiments, we have demonstrated that fragment AAV oversized gene transduction is better than or similar to the other approaches of AAV large gene transduction, which in general are referred to as "dual vector" approaches (reviewed by Pryadkina et al., *Mol. Ther. Methods Clin. Dev.* 2:15009 (2015); Hirsch et al., *Mol Ther.* 18:6 (2010); Hirsch et al., *Mol Ther.* 21:2205 (2013)). In our published work investigating fragment AAV and dual AAV transduction efficiencies, intact AAV remained 5- to 100-fold more efficient than an AAV capsid packaged that relies on single AAV vector transduction.

Therefore, our focus for in vivo analysis relied on the JeT-Nano-Dysferlin cassette for single AAV vector transduction. A limitation of our efforts herein is that the JeT promoter is small, as required for intact genome packaging, yet relatively weak and ubiquitous in nature, which is not ideal for a skeletal muscle therapy delivered IV (Tornøe et al., *Gene* 297:21 (2002)) (FIGS. 2A-2D). Currently, the small muscle-specific promoters C2-27 and C5-12 are under investigation, which are hypothesized to allow intact genome packaging when combined with Nano-Dysferlin, in an AAV context while likely having significantly enhanced transcriptional activity in muscle (Li et al., *Nat. Biotechnol.* 17:241 (1999)).

Contralateral administration of AAV1-JeT-Nano-Dysferlin directly to dysferlin-deficient skeletal muscle resulted in increased muscle integrity in every mouse tested, as determined by decreased Evans blue dye fiber staining, and all but one mouse tested by central nucleated fibers (FIGS. 3A-3B). This contralateral intra-mouse comparison is important because the dysferlin phenotype between animals (FIGS. 3A-3B, black bars) was variable, perhaps due to environmental contexts (i.e., increased individual activity for particular mice). Despite this inter-mouse variability in disease severity, the results clearly demonstrated increased integrity and significantly improved muscle phenotype as a result of Nano-Dysferlin, evident by immunofluorescence (IF) in approximately 30% of treated fibers (FIG. 3C). Interestingly, we note that Nano-Dysferlin localization following gene delivery is not primarily restricted to the sarcolemma, as observed for native dysferlin in WT mice (FIG. 3D). This result is puzzling yet not specific to Nano-Dysferlin because restoration of WT dysferlin via a multiple vector approach also results in abnormal intracellular distribution, as evidenced by previous reports (Lostal et al., *Hum. Mol. Genet.* 19:1897 (2010); Grose et al., *WPLoS ONE* 7:e39233 (2012)). The reason for this aberrant localization is speculated to result from restoration of dysferlin (or Nano-Dysferlin) to terminally differentiated myofibers because dysferlin has been suggested to be regulated during differentiation; however, other theories, such as altered abundance per fiber, are also entertained.

Figure 5E:
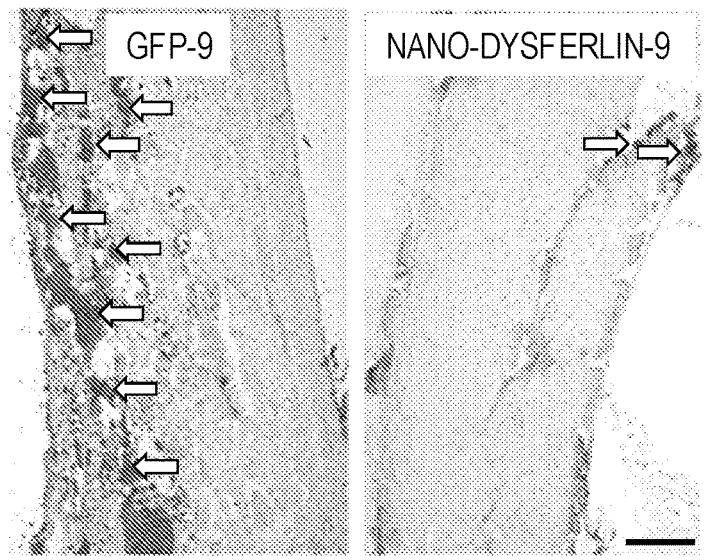

Curiously, the onset of dysferlinopathy in human patients generally begins during the teenage years in previously asymptomatic, and often athletic, individuals. Reports have suggested the reason for this may be related to the metabolic switch in cellular respiration from oxidative to glycolytic predominance during this time (Armstrong et al., *Pediatr. Exerc. Sci.* 21:130 (2009); Stephens et al., *Int. J. Sport Nutr. Exerc. Metab.* 16:166 (2006); Taylor et al., *Mol. Cell. Biochem.* 174:321 (1997); Timmons et al., *Appl. Physiol. Nutr. Metab.* 32:416 (2007); Timmons et al., *J. Appl. Physiol.* 94:278 (2003)). This is consistent with the emergence of muscular dystrophy phenotype in BLA/J dysferlin-deficient mice starting at 15 weeks of age (Nagy et al., *Physiol. Rep.* 5:e13173 (2017)). In fact, studies have found both dysferlin-deficient BLA/J mice and primary human myoblasts have an impaired glucose and lipid uptake/metabolism (Keller (2014) Thesis (Berlin: Universitätsmedizin Berlin)). Furthermore, prior reports have shown lipid accumulation is a feature observed in human and BLA/J mouse dysferlinopathy yet has not been reported in other muscular dystrophies, such as calpainopathy, DMD, and myotonic dystrophy (Grounds et al., *Am. J. Pathol.* 184:1668 (2014)). Consistent with this line of thought, our previous study found an increase in extramyocellular lipids (EMCLs) in gluteal and psoas BLA/J mouse muscles, the most affected muscles in the BLA/J mouse model, with visible fatty infiltration in MRI images of gluteal muscles (Nagy et al., *Physiol. Rep.* 5:e13173 (2017)). After analysis of muscle sections stained by H&E in the present study, differences in potential fatty infiltrates became apparent between treatments. To confirm this, we performed oil red O staining for lipids, which revealed a drastic reduction of fat infiltrates in AAV9Jet-Nano-Dysferlin-treated mice (FIG. 5E).

The experiments designed herein attempted to imitate a potential clinical situation by systemically treating 6-month animals already demonstrating progressive muscular disease, with a single dose of AAV9-JeT-Nano-Dysferlin. The results of blinded experiments demonstrate that BLA/J mice treated with AAV9-Jet-Nano-Dysferlin reared on average 200 more times during a 1-hr evaluation, totaling nearly twice the activity of control treated mice. In previous work, we observed that the rearing deficit compared to WT mice increased over time, suggesting earlier onset of fatigue in BLA/J mice (Nagy et al., *Physiol. Rep.* 5:e13173 (2017)). The work herein is consistent with a therapeutic effect of AAV9-JetNano-Dysferlin because, when analyzed over time, treated mice performance strongly suggested fatigue correction and demonstrated rearing levels similar to those of WT mice, as observed in our previous study (Nagy et al., *Physiol. Rep.* 5:e13173 (2017)). One additional take away from this study for future locomotor evaluation of therapeutics, and given the observed "fatigue" of BLA/J mice, is that appropriately designing locomotor experiments that extend the time of activity testing beyond 60 min may reveal stronger, more drastic deficiencies present in this model for dysferlinopathy. This remains to be tested in future studies (FIG. 4C).

Post-mortem analysis of Evans blue dye uptake using a whole muscle assay (FIG. 5B) by conventional Evans blue dye histology (FIG. 5C), central nucleated fibers (FIG. 5A), and semi-automated fiber size analysis by Feret diameter (FIGS. 5D and 7) agreed that BLA/J mice treated with AAV9-Jet-Nano-Dysferlin were increased for muscle integrity in the most affected BLA/J muscle group, the gluteal muscles (Nagy et al., *Physiol. Rep.* 5:e13173 (2017)), where approximately 10% of muscle fibers stained positive for Nano-Dysferlin by immunofluorescence (FIG. 8), consistent with the notion that a little dysferlin (or in this case Nano-Dysferlin) goes a long way in maintaining muscle integrity (Lostal et al., *Hum. Mol. Genet.* 19:1897 (2010)). In no cases herein, whether dysferlin-deficient patient myoblasts or unrestricted production in the BLA/J model, did we see toxicity for Nano-Dysferlin or AAV vector transduction. However, again, we note that the ubiquitous JeT promoter is relatively weak, resulting in detectable but low levels of Nano-Dysferlin.

Further experimentation with stronger and muscle-restricted promoters is needed to confirm this result. In addition, we note that a single new epitope was generated by deletion of the C2D, E, and F domains, which raises the potential of a Nano-Dysferlin-specific cellular-mediated immune response, depending on the nature of the patient's mutation. This is a similar scenario to the application of micro- or mini-dystrophin to DMD patients or even full-length dysferlin administration to dysferlinopathy patients due to the myriad of possible mutations. Despite these standard therapeutic concerns, Nano-Dysferlin represents the only single AAV-vector amenable dysferlin variant that restores motor function in dysferlin-deficient mice and represents an attractive candidate for the treatment of dysferlinopathy in the clinic.

Materials and Methods

Study Design: This study was designed to generate an AAV therapeutic for dysferlinopathy. To test this, Nano-Dysferlin, an abridged dysferlin-like molecule, was created and tested functionally in vivo using AAV technology. The currently best animal model of dysferlinopathy, BLA/J mice, was chosen due to its clinically relevant phenotypic characteristics. All mouse experiments were blinded to the handler in terms of the type of treatment, and the results were un-blinded only after statistical analysis. The experimental endpoints and time of initial treatment were based on earlier characterization of the BLA/J model (Nagy et al., *Physiol. Rep.* 5:e13173 (2017)). The in vitro experiments were repeated on at least 2 separate days, with a minimal replicate number of 3 for each occasion. The animal experiments were performed once with the indicated replicate number and duration. For the intramuscular experiment, littermates were administered randomly assigned treatments with contralateral controls. For the systemic experiment, mice were randomly assigned treatments. Investigators performing all animal interaction and data collection were blinded. Alpha was set at the traditional 0.05 for significance. Post hoc power analysis of the rearing behavioral performance assay was done in G-Power 3.1.9.2 software, an effect size of 1.77 was obtained using group means, and standard deviation within each group was estimated by the pooled standard deviation equation, with a power (1-b error probability) of 0.76. One mouse was eliminated from the intramuscular experiment due to a missed Nano-Dysferlin injection, as evidenced by lack of India ink in the targeted TA muscle. In the systemic experiment, one Nano-Dysferlin-treated mouse was eliminated as an outlier because it had less than half the rearing performance of the median for all other Nano-Dysferlin-treated mice. No major changes in p value throughout the performed experiments arose from this exclusion.

Designing Nano-Dysferlin: The Nano-Dysferlin gene was based on the wild-type dysferlin isoform eight cDNA (6,240 nt), which contains domains C2A-C2BC2C-FerA-DysF-C2D-C2E-C2F-C2G-TM. Wild-type domains were defined in terms of the available primary sequence as follows. Each C2 domain range in Table 2 was analyzed for predicted b strand content, potential $Ca^{2+}$-binding residues, C2 domain topology, overall C2 domain length, and continuity of hydrophobic packing of the domain's core. Once this was completed, dysferlin could be edited in silico by defining excision sites that extended from the N-terminal linker to the C-terminal linker of each C2 domain. All abbreviated protein constructs retained the C2A domain, FerA domain, DysF domain, C2G domain, and transmembrane helix in addition to the short extra-cellular portion of the protein. All other C2 domains were dispensable. Finally, genes corresponding to the new proteins were assembled by GenScript, with codon optimization for human synthesis. Nano-Dysferlin itself possesses domains C2A-C2B-C2CFerA-DysF-C2G-TM at a total length of 4,356 nt.

Cell Lines and Culture Media: HeLa cells were used for immunofluorescence and grown in DMEM supplemented with 10% Sigma fetal bovine serum (FBS) (F7524) and 1% Pen/Strep antibiotic. Immortalized human patient "ER" myoblasts bearing dysferlin exon 44: c.4882G>A HMZ, p.G1628R homozygous mutation were obtained from Dr. E. Gallardo and grown in Promocell Skeletal Muscle Cell Growth Medium Kit (C-23060) supplemented with 15% Sigma FBS (F7524), 2 mM Glutamax by Life Technologies (35050), and 100 mg/mL Primocin by Invivogen (ant-pm-1). C2C12 myoblasts were obtained from ATCC (CRL1772) and grown in DMEM supplemented with 10% Sigma FBS (F7524) and 1% Pen/Strep antibiotic. HEK293 cells, used for western blots and AAV vector production, were obtained from ATCC (CRL1573) and cultured in DMEM supplemented with 10% Sigma FBS (F7524) and 1% Pen/Strep antibiotic.

Plasmids and Viral Production: The Nano-Dysferlin nucleotide sequence was generated by GenScript based on our amino acid sequence submission and their human codon optimization algorithm. PCR sub-cloning added a 3× FLAG tag to the 3° ORF and moved the Nano-Dysferlin sequence into pSJG-JeT-GFP-synpolyA self-complementary plasmid (kind gift of Dr. S. Gray at University of North Carolina [UNC]) at the NcoI and XhoI sites. This cassette was then excised using KpnI and MluI, and the ends were blunted and then cloned into blunted KpnI/SphI sites of pTReGFP (a single-strand AAV plasmid) (Zolotukhin et al., J. Virol. 70:4646 (1996)). The region from between the AAV2-inverted terminal repeats on this resultant plasmid was then confirmed by sequencing. For these experiments, phpaTRSK-CMV-GFP was used to generate the GFP control AAV vector (McCarty et al., Gene Ther. 8:1248 (2001)). Virus was produced by triple transfection protocol in HEK293 cells (Grieger et al., Nat. Protoc. 1:1412 (2006)). This method used the pXR1, pXR2, and pXR9 plasmids, along with the pXX680 helper (kind gifts of Dr. R. J. Samulski). The titer of all vector preps was determined by southern dot blot and confirmed by qPCR. When applicable, the packaged genome species were confirmed by alkaline gel electrophoresis and SYBR gold staining (Grieger et al., Nat. Protoc. 1:1412 (2006)).

Nano-Dysferlin Intramuscular and Systemic Administration: For the intramuscular experiment, data shown in FIGS. 3A-3D, AAV1Nano-Dysferlin or AAV1-CMV-GFP was injected intramuscularly into contralateral TA muscles a single time at 6 weeks of age. Isoflurane-sedated mice were injected with a BD 8-mm 31-gauge needle in 50 μl of total volume (5e10 total viral genomes) administered per TA containing 2% India ink (America Master Tech Cat: STIIN25). For the systemic experiment, AAV9-JeT-Nano-Dysferlin (n=6) or AAV9-CMV-GFP (n=4) was administered by a tail-vein injection a single time at 4 and a half months of age with a BD 8-mm 31-gauge needle in a total volume of 200 μl (2e11 total viral genomes).

Western Blots: CMV Nano-Dysferlin plasmid was first tested by western blot alongside CMV wild-type dysferlin 48 hr post-transfections of C2C12 mouse myoblasts using Lipofectamine 3000 (ThermoFisher Cat: L3000001), as described in the product protocol. Mammalian protein extraction reagent (MPER; Thermo Scientific Cat: 78501) was used to extract protein for total protein lysate western blots. Isolated cytoplasm and membrane-associated protein lysates were obtained via the Mem-PER Plus Membrane Protein Extraction kit (ThermoFisher Cat: 89842). For intramuscular and intravenous experiments, muscle was harvested and followed the mammalian protein extraction reagent protocol (ThermoFisher Cat: 78501). All protein lysates were subsequently denatured, added to 4× NuPage solution (ThermoFisher Cat: NP0008) with a final concentration of 5% β-mercaptoethanol, and run on a precast 4%-12% BIS-TRIS gradient gel (ThermoFisher Cat: NP0321). All dysferlin and Nano-Dysferlin detection experiments employed the Romeo primary antibody (Abcam Cat: 124684) at a 1:2,000 concentration, followed by a secondary anti Rabbit HRP antibody (Abcam Cat: ab6721) at a 1:10,000 concentration. Sirius chemiluminescence kit (Advansta Cat: K-12043-D20) was used for all blots, and blots were imaged by the Amersham A600 imager.

Toxicity Assay: Dysferlin-deficient (ER) human patient cells, courtesy of the Jain Foundation, were plated in a 24-well plate and grown in Promocell Skeletal Muscle Cell Growth Medium Kit (C-23060) supplemented with 15% Sigma FBS (F7524), 2 mM Glutamax by Life Technologies (35050), and 100 mg/mL Primocin by Invivogen (ant-pm-1). Cells were approximately 70% confluent when Lipofectamine 3000 was used for transfection using the recommended protocol. Low, medium, and high doses consisted of 0.5 mg, 1 mg, and 1.5 mg of pCMV-GFP, pCMV-Nano-Dysferlin, or pCMV-dysferlin DNA plasmids. The cell's medium was replaced 24 hr after transfection, and 50 μl of alamar Blue cell viability reagent (DAL1100) was added to each well 48 hr after transfection; readouts were followed per product protocol. 100 μl of medium was taken from each well 72 hr after transfection for analysis in a fluorescent plate reader.

Animals and Animal Care: Subjects for all in vivo experiments were a total of 15 BLA/J mice on a C57BL/67 background bred from mice originally obtained from Jackson Laboratory. Intramuscular experiments used an equal number of male and female littermates. Intravenous experiments used three females for both groups, two males for the Nano-Dysferlin group, and one male for the control group. Subjects were group housed in ventilated cages, with free access to water and mouse chow. The housing room was maintained on a 12L:12D circadian schedule, with lights on at 7 AM. All testing procedures were conducted in strict compliance with the "Guide for the Care and Use of Laboratory Animals" (Institute of Laboratory Animal Resources, National Research Council, 1996) and approved by the Institutional Animal Care and Use Committee of UNC.

Evans Blue Dye Assays: Mice were injected intraperitoneally 40 hr prior to sacrifice with Evans blue dye (10 mg/mL) at 5 mL/g of body weight. Mice were housed in a new environment on the last day prior to sacrifice to exacerbate the relatively mild dysferlin-deficient phenotype. For the positive fiber count assay, muscles were cross-sectioned at a 10-mm thickness over seven locations at least 500 mm apart throughout the muscle. Utilizing fluorescent microscopy, total fibers were counted and compared against positive fibers. For the Evans blue dye absorbance assay, muscle pieces were normalized by weight and placed in Eppendorf tubes. 1 mL of formamide was added and incubated at 55° C. for 2 hr. Samples were centrifuged at 12,000 rpm for 2 min to remove debris, and supernatants were added to a 96 well plate in triplicate for each muscle. Absorbance was measured at 620 nm in a plate reader. One intravenous mouse did not receive Evans blue dye and was used to quantitate immunofluorescence staining.

H&E Central Nucleation: Muscle cross-sections, as described above, were stained for H&E by the UNC Histology Core. Central nucleated fibers were counted against area in mm$^2$, as previously evaluated in the literature (Lostal et al., *PLoS ONE* 7:e38036 (2012)). Additionally, an alternate measure of central nucleation comparing total intact fibers counted against total central nuclei was also evaluated (Duddy et al., *Skelet. Muscle* 5:16 (2015)).

Oil Red O Staining: Muscle cross-sections, as described above, were stained for Oil Red O by the UNC Histology Core.

Fiber Size Analysis: Muscle sections were stained with WGA lectin and analyzed on ImageJ by first splitting RGB channels and using the find edges function with the green channel. This was followed by applying an auto Huang threshold and using the binary options open function set at a "4" count over ten iterations (black background). This was followed by the binary options fill holes function, and remaining open fiber edges were closed manually. This was followed by the analyze particles function, and the minimal Feret diameter measurement was converted to microns.

Immunofluorescence: Muscle tissue from the intramuscular and intravenous cohort were flash frozen in Sakura TissueTek Cryomolds (REF4557) using optimal cutting temperature (OCT) by dipping into isopentane cooled by liquid nitrogen. Tissue was then sliced at 10 mm using a Leica CM3050-S cryostat and stored at 80° C. Tissue was then thawed in a humidity chamber at room temperature. Thawed tissue was fixed for 15 min in 4% paraformaldehyde/4% sucrose solution. Muscle was then stained with WGA-Alexa 488 conjugate at a concentration of 50 mg/mL for 10 min at room temperature. 10% BSA was used to block the tissue, and Abcam ab124684 anti-dysferlin antibody was used at a 1:200 dilution for 2 hr at 37° C. Secondary antibody goat anti Rabbit 594 Life Technologies (A11037) was used at a 1:1,000 dilution. Hoechst stain (H3569) was used at a 1:10,000 dilution for 5 min at room temperature. Coverslips were mounted and imaged in an Olympus IX-83 fluorescence microscope.

Immunofluorescence Fiber Counts: For intramuscular experiments, fibers staining above background for Nano-Dysferlin were counted manually against total fibers based on fiber outlines employing the ImageJ cell counter and multi-point analysis tool. This procedure was carried out in both Nano-Dysferlin and its contralateral GFP controls. GFP control "false positives" were then also subtracted to estimate the approximate Nano-dysferlin expression. It is worth mentioning vector systemic shedding is a common occurrence with AAV, which may account for transduction of the contralateral leg. For systemic experiments, due to expected weaker staining, one treated mouse was not injected with Evans blue dye. In this case, WGA-stained outlines were used to determine total fibers, which were used to normalize the total positive fibers observed. Positive fibers observed in a no-treatment control mouse were used to subtract "false positives."

Creatine Kinase Assay: Blood drawn from the submandibular vein, approximately 200 μL, was placed in EDTA tubes and centrifuged at 1,500 rpm for 10 min to separate blood solids. Plasma was processed using the creatine kinase activity colorimetric assay kit (Abcam Cat: 155-901) following protocol instructions. Samples were measured in a Perkins colorimetric plate reader.

Rearing Behavioral Assay: The number of times the mice stood on two legs (termed rearing) was quantitated over 60 min at 5-min intervals. Rearing in a novel environment was assessed in a photocell-equipped open field automatic (41 cm 41 cm 30 cm; Versamax system, Accuscan Instruments). Activity chambers were themselves placed in sound-attenuating containers equipped with fans and houselights.

Horizontal Activity Behavioral Assay: The horizontal activity of mice was quantitated over 60 minutes at 5 minute intervals. Horizontal activity in a novel environment was assessed in a photocell-equipped open field automatic (41 cm×41 cm×30 cm; Versamax system, Accuscan Instruments). Activity chambers themselves were placed in sound-attenuating containers equipped with fans and houselights.

Fiber Size Analysis: Muscle sections were stained with WGA lectin and were analyzed on ImageJ by first splitting RGB channels, and using the find edges function with the green channel. This was followed by applying an auto Huang threshold, and using the binary options open function set at a "4" count, over 10 iterations (black background). This was followed by binary options fill holes function, and remaining open fiber edges were closed manually. This was followed by the analyze particles function, and the Minimal Feret Diameter measurement was converted to microns (Briguet et al., *Neuromuscular disorders: NMD* 14: 675 (2004); Bansal et al., *Nature* 423:168 (2003).

Detection by RT-PCR: Extracted tissue from mouse muscles evaluated was immediately stored in dry ice and then −80° C. freezer in 1.5 ml epi tubes. Trizol reagent (Thermo Fisher: 15596026) was added to samples and then allowed to thaw. After mechanical homogenization, lysing and phase separation was carried out per product protocol. RNA was then purified by Qiagen RNeasy Fibrous Tissue Kit (Cat No./ID: 74704) by the product protocol. Reverse transcription was performed, and primers ccgacacgcctacctgag (SEQ ID NO:13) and ccggcactaaaatcgtcag (SEQ ID NO:14), obtained from Roche UPL primer design library were used to generate a 60 nucleotide amplicon. Samples were treated with Exo-Sap-it PCR Cleanup Reagent (Thermo Fisher 78200.200), run on a 2% agarose gel, and imaged subsequently.

The foregoing is illustrative of the present invention, and is not to be construed as limiting thereof. The invention is defined by the following claims, with equivalents of the claims to be included therein.

That which is claimed is:

1. A polynucleotide encoding a truncated variant of a wild-type mammalian dysferlin polypeptide, the wild-type mammalian dysferlin polypeptide comprising an amino acid sequence for each of domains C2A, C2B, C2C, FerA, DysF, C2D, C2E, C2F, C2G, and TM, wherein the truncated variant of the wild-type mammalian dysferlin polypeptide comprises, in order, at least 95% of the amino acid sequence of each of domains C2A, C2B, C2C, FerA, DysF, C2G, and TM of the wild-type mammalian dysferlin polypeptide, wherein at least 95% of the amino acid sequence of each of domains C2D, C2E, and C2F of the wild-type mammalian dysferlin polypeptide is deleted, wherein the truncated variant of the wild-type mammalian dysferlin polypeptide exhibits sarcolemma localization and/or maintains muscle membrane integrity, and wherein the polynucleotide is: (a) a polynucleotide comprising a sequence at least 95% identical to any one of SEQ ID NOS: 2 or 5 or (b) a polynucleotide comprising a sequence encoding a polypeptide identical to any one of SEQ ID NOS: 7 or 10.

2. The polynucleotide of claim 1, wherein the wild-type mammalian dysferlin polypeptide is a human dysferlin polypeptide.

3. The polynucleotide of claim 1, wherein the polynucleotide is a polynucleotide comprising a sequence identical to any one of SEQ ID NOS: 2 or 5.

4. An expression cassette comprising the polynucleotide of claim 1.

5. The expression cassette of claim 4, wherein the polynucleotide is operably linked to a promoter.

6. A vector comprising the polynucleotide of claim 1.

7. The vector of claim 6, which is a viral vector.

8. The vector of claim 7, which is an adeno-associated virus (AAV) vector.

9. A transformed cell comprising the polynucleotide of claim 1.

10. A truncated variant of a wild-type mammalian dysferlin polypeptide, the wild-type mammalian dysferlin polypeptide comprising an amino acid sequence for each of domains C2A, C2B, C2C, FerA, DysF, C2D, C2E, C2F, C2G, and TM, wherein the truncated variant of the wild-type mammalian dysferlin polypeptide comprises, in order, at least 95% of the amino acid sequence of each of domains C2A, C2B, C2C, FerA, DysF, C2G, and TM of the wild-type mammalian dysferlin polypeptide, wherein at least 95% of the amino acid sequence of each of domains C2D, C2E, and C2F of the wild-type mammalian dysferlin polypeptide is deleted, wherein the truncated variant of the wild-type mammalian dysferlin polypeptide exhibits sarcolemma localization and/or maintains muscle membrane integrity, and wherein the polypeptide is:
   (a) a polypeptide encoded by a polynucleotide comprising a sequence at least 95% identical to any one of SEQ ID NOS: 2 or 5; or
   (b) a polypeptide comprising a sequence at least 95% identical to any one of SEQ ID NOS: 7 or 10.

11. A recombinant AAV particle comprising the polynucleotide of claim 1.

12. A method of administering dysferlin to a mammalian subject, comprising administering to the mammalian subject the recombinant AAV particle of claim 11 or a cell that has been contacted with the recombinant AAV particle of claim 11, thereby administering dysferlin to the mammalian subject.

13. A method of treating dysferlinopathy in a mammalian subject in need thereof, comprising administering to the mammalian subject the recombinant AAV particle of claim 11 or a cell that has been contacted with the recombinant AAV particle of claim 11, thereby treating the dysferlinopathy.

14. The polypeptide of claim 10, wherein the polypeptide is:
   (a) a polypeptide encoded by a polynucleotide comprising a sequence identical to any one of SEQ ID NOS: 2 or 5; or
   (b) a polypeptide comprising a sequence identical to any one of SEQ ID NOS: 7 or 10.

15. The polypeptide of claim 10, wherein the wild-type mammalian dysferlin polypeptide is a human dysferlin polypeptide.

* * * * *

SEQUENCE LISTING

<160> NUMBER OF SEQ ID NOS: 14

<210> SEQ ID NO 1
<211> LENGTH: 4500
<212> TYPE: DNA
<213> ORGANISM: Artificial
<220> FEATURE:
<223> OTHER INFORMATION: Clone_318 No Flag (433)

<400> SEQUENCE: 1

| | | | | | |
|---|---|---|---|---|---|
| atgctgaggg | tgttcatcct | gtatgctgag | aacgtgcaca | cacccgacac | tgatattagc | 60 |
| gacgcctact | gctccgccgt | gtttgctgga | gtgaagaaaa | gaaccaaggt | gatcaaaaac | 120 |
| tctgtgaatc | ccgtgtggaa | cgaagggttc | gagtgggatc | tgaagggaat | tcctctggac | 180 |
| caggggagtg | agctgcacgt | ggtggtgaaa | gatcatgaaa | caatgggcag | aaaccggttt | 240 |
| ctgggagaag | ctaaggtgcc | actgagggag | gtgctggcta | ctccaagcct | gtccgcttct | 300 |
| ttcaatgctc | ctctgctgga | cactaagaaa | cagccaaccg | gagcttctct | ggtgctgcag | 360 |
| gtgtcttaca | ccgacctgga | tgtggtggcc | gacactggcg | aggaagacac | cgaggatcag | 420 |
| ggactgacac | ctttcctgga | ccagagcgga | ggaccaagaa | agctgccatc | ccggggcatc | 480 |
| aagcgcaaaa | ggagcattcg | cgtgcaggtg | atcgagggga | ggcagctgcc | tggcgtgaac | 540 |
| atcaagccag | tggtgaaagt | gaccgccgct | ggacagacca | agagaacacg | gattcacaaa | 600 |
| gggaactctc | ccctgttcaa | tgagacactg | ttctttaatc | tgtttgatag | tccaggcgaa | 660 |
| ctgttcgacg | agcccatctt | tattacagtg | gtggatagtc | gcagcctgag | gactgacgct | 720 |
| ctgctgggcg | agtttcgcat | ggatgtggga | accatctata | gagaaccacg | gcatgcctac | 780 |
| ctgaggaaat | ggctgctgct | gagcgaccca | gacgatttct | ccgctggagc | tagaggatac | 840 |
| ctgaagacat | ctctgtgcgt | gctgggacct | ggggatgaag | ccccactgga | gcggaaggac | 900 |
| ccttctgaag | acaaagagga | tatcgaaagt | aacctgctga | gaccaaccgg | agtggctctg | 960 |
| aggggagctc | acttctgtct | gaaagtgttt | cgcgctgagg | atctgcctca | gatggacgat | 1020 |
| gccgtgatgg | acaatgtgaa | gcagatcttc | ggctttgaga | gcaacaagaa | aaatctggtg | 1080 |
| gacccttcg | tggaagtgag | ctttgccgga | agatgctgt | gctccaagat | cctggagaaa | 1140 |
| actgctaacc | cacagtggaa | ccagaatatt | accctgcctg | ccatgttccc | aagcatgtgt | 1200 |
| gagaagatgc | gcatcaggat | cattgactgg | gataggctga | cccacaatga | cattgtggct | 1260 |
| actacctacc | tgtccatgtc | taagatttcc | gcccctggag | gagagatcga | ggaagagcca | 1320 |
| gctggagctg | tgaagcctag | caaagcctcc | gatctggacg | attatctggg | gtttctggag | 1380 |
| cacagtgaac | agaaagtgga | ggatctgcct | gccgacgata | tcctgcgcgt | ggaaaagtat | 1440 |
| ctgaggagac | ggaaatacag | cctgtttgcc | gctttctact | ccgctacaat | gctgcaggac | 1500 |
| gtggacgatg | ccattcagtt | cgaggtgtcc | atcgggaacc | atcgcatcga | gcccagaat | 1560 |
| cagctgctgg | gcatcgccga | caggctggaa | gctggactgg | agcaggtgca | cctggccctg | 1620 |
| aaggctcagt | gctctaccga | ggacgtggat | agtctggtgg | ctcagctgac | agacgaactg | 1680 |
| atcgccggat | gtagccagcc | actggggat | attcacgaga | caccctccgc | cactcatctg | 1740 |
| gaccagtatc | tgtaccagct | gagaacccac | catctgagcc | agatcacaga | ggccgctctg | 1800 |
| gctctgaagc | tgggccattc | cgaactgcca | gctgctctgg | agcaggctga | agactggctg | 1860 |
| ctgaggctga | gggctctgaa | actgcagacc | atcttcctga | agtacccaat | ggagaaagtg | 1920 |
| cccggcgccc | gcatgcctgt | gcagattagg | gtgaagctgt | ggtttggact | gtctgtggac | 1980 |
| gagaaggaat | taaccagtt | cgctgaaggg | aaactgagtg | tgttcgccga | gacctacgag | 2040 |

```
aacgaaacta agctggccct ggtgatggat gccggccatc tgtctttcgt ggaagaggtg    2100
tttgagaacc agactcgcct gccaggcgga cagtggatct atatgagtga caactacacc    2160
gatgtgaatg gcgagaaggt gctgcctaaa gacgatattg aatgtccact gggatggaag    2220
tgggaggacg aagagtggag caccgatctg aaccgggctg tggacgaaca gggctgggag    2280
tactccatca caattccccc tgagcgcaag ccaaaacact gggtgcccgc cgaaaaaatg    2340
tattacaccc atagaaggag gagatgggtc aggctgagaa ggagggatct gtctcagatg    2400
gaggccctga agagacatag gcaggctgag gctgaaggag agggatggga gtatgctagc    2460
ctgtttggct ggaagttcca cctggaatac agaaaaaccg acgcctttag gagaaggagg    2520
tggaggagaa ggatggagcc actggaaaaa acacctgcca ttcaccatat ccccggattc    2580
gaggtgcagg aaacaagccg gatcctggac gaatccgagg acactgatct gccttatcct    2640 ccacccagc gcgaggctaa catttacatg gtgcctcaga atatcaaacc agccctgcag    2700
cgcactgcta tcgagattct ggcctggggc ctgaggaaca tgaagtctta ccagctggcc    2760
aatatctcta gtcctagtct ggtggtggag tgcggagggc agaccgtgca gagctgtgtg    2820
atcagaaacc tgcggaagaa ccccaatttc gacatttgca ctctgtttat ggaggtgatg    2880
ctgcctagag aagagctgta ctgtcctcca attaccgtga aggtgatcga taatagacag    2940
tttggaagga ggccagtggt gggacagtgc accatccgga gcctggagtc cttcctgtgt    3000
gacccttata gcgctgaaag ccccttcccca cagggaggac ctgacgatgt gtctctgctg    3060
agtccaggcg aggacgtgct gatcgatatt gacgataagg aacccgagaa ggactttgat    3120
actctgaaag tgtacgatac ccagctggag aacgtggaag ccttcgaggg gaataccttc    3180
aagctgtaca ggggcaaaac cgatccatcc gtgattgggg agtttaaggg cctgctcgtg    3240
agaatctaca ttgtgcgggc cttcgggctg cagcctaagg atccaaacgg caaatgtgac    3300
ccctatatca agatttccat cggaaagaaa tctgtgagtg accaggataa ttacatcccc    3360
tgcacactgg aacctgtgtt tgggaagatg ttcgagctga cttgtaccct gcctctggaa    3420
aaggacctga aaatcactct gtatgactac gatctgctga gcaaggatga aaaaattggg    3480
gagaccgtgg tggacctgga aacagactg ctgtccaagt tcggagctag atgcggactg    3540
ccacagacat actgtgtgtc tggccctaat cagtggcgcg accagctgac tcaggacaaa    3600
gaatacagca ttgaggaaat cgaggctgga agaatcccaa acccagagga aaggctggcc    3660
ctgcatgtgc tgcagcagca gggcctggtg cccgaacacg tgaaagctct gggacgccca    3720
gggccaccct ttaacatcac ccctagacgg gcccgcaggt tctttctgcg ctgcatcatt    3780
tggaatacta gggatgtgat cctggacgat ctgtctctga ccggagagaa gatgagtgac    3840
atttatgtga aaggctggat gatcggattt gaggaacaca gcagaaaac agatgtgcat    3900 tacagatctc tgggggggcga gggcaacttc aattggcggt tcatctttcc attcgactat    3960
ctgcccgctg aacaagtgtg taccattgcc aagaaagatg ctttctggcg cctggacaag    4020
acagagagca aaattcctgc cagggtggtg ttccagatct gggacaacga taagtttagc    4080
ttcgacgatt ttctgggatc cctgcagctg gatctgaatc ggatgcctaa gccagccaaa    4140
accgctaaga aatgctctct ggaccagctg gacgatgcct tccatccaga atggtttgtg    4200
agtctgttcg agcagaagac tgtgaaaggc tggtggccct gtgtggctga ggaaggagag    4260
aagaaaatcc tggccgggaa gctggaaatg accctggaga ttgtggctga agaccagct    4320 ggaccaagac ggcccgatac atcttttctg tggttcacca gtaaattcat cctgtggcgc    4380
```

```
aggtttagat gggccatcat tctgtttatc attctgttca ttctgctgct gtttctggct    4440
attttcatct atgcctttcc taactacgcc gctatgaagc tggtgaaacc attcagctga    4500

<210> SEQ ID NO 2
<211> LENGTH: 4284
<212> TYPE: DNA
<213> ORGANISM: Artificial
<220> FEATURE:
<223> OTHER INFORMATION: Clone_431 No Flag (431)

<400> SEQUENCE: 2
atgctgcgag tctttattct gtatgccgaa aacgtccaca ccccgacac cgacatctct      60 gatgcttact gctccgccgt ctttgccggg gtcaagaaaa ggaccaaagt gatcaagaac    120
agtgtgaatc ctgtctggaa cgagggattc gaatgggatc tgaagggcat tccactggac    180
caggggtcag aactgcacgt ggtcgtgaaa gaccatgaga caatgggaag gaaccgcttc    240
ctgggcgaag caaaggtgcc tctgcgagag gtcctggcaa ctccatctct gagtgccagc    300
ttcaacgctc cctgctggta actaagaaaa cagcctaccg gggcaagcct ggtgctgcag    360
gtctcctata cacctctgcc aggagcagtg cctctgttcc cacctccaac tccactggaa    420
cccagcccta cctgccaga cctggatgtc gtggccgaca ctggcgggga ggaagacacc    480
gaggatcagg gcctgacagg ggatgaagct gagccctttc tggaccagtc aggaggcccc    540
ggagcaccta ccacacccag aaagctgcca agcagacccc ctccacacta ccccggcatc    600
aagcgaaaac gatcagcacc aaccagccgg aagctgctgt ccgacaaacc tcaggatttt    660
cagatccgcg tgcaggtcat tgagggccga cagctgcctg ggtcaacat caagccagtc    720 gtgaaagtga ctgccgctgg acagactaag agaaccagga ttcataaagg caactccccc    780
ctgttcaatg agaccctgtt ctttaatctg tttgattctc ccggcgaact gttcgacgag    840
cctatcttta ttactgtcgt ggatagcaga tccctgagga ccgacgctct gctgggagaa    900
ttcagaatgg acgtgggcac tatctatcgc gagccccgac acgcctacct gaggaaatgg    960
ctgctgctgt ctgatcctga cgattttagt gccggagctc gcggctacct gaagacctct    1020
ctgtgcgtgc tgggaccagg ggatgaagca ccactggaga ggaaggaccc atcagaggac    1080
aaagaagata tcgagagcaa cctgctgcga cccaccggag tcgcactgcg gggcgcccac    1140
ttctgtctga agtgtttcg cgctgaggac ctgccccaga tggacgatgc agtgatggat    1200
aatgtcaagc agatcttcgg cttttgaaagc aacaagaaaa atctggtgga cccccttcgtg    1260 gaggtctcct tgccgggaa gatgctgtgc tctaagatcc tggagaaaac agccaaccct    1320
cagtggaacc agaatattac tctgccagct atgttcccca gcatgtgtga aaaatgcgc    1380 atccgaatca ttgactggga tagactgaca cacaatgata ttgtggccac tacctatctg    1440
tctatgagta agatctccgc tccagggggga gagattgagg aagagcccgc aggcgccgtg    1500
aagccttcta agccagtgaa cctggacgat tacctgggg ttctgcctac attcggacca    1560
tgctatatca acctgtacgg gtccccccgg gagtttactg gattcccaga tccctacaca    1620
gaactgaata ctggaaaggg cgaggggtg gcttatcggg gcagactgct gctgagtctg    1680
gagaccaagc tggtcgaaca ttcagagcag aaagtggaag acctgcccgc cgacgatatc    1740
ctgagagtgg agaagtatct gcggagaagg aaatacagtc tgtttgcagc cttctattca    1800
gccaccatgc tgcaggatgt cgacgatgct atccagttcg aggtgagcat tgggaactac    1860
ggaaataagt ttgacatgac atgcctgcct ctggcaagta caactcagta ttcacgggcc    1920
gtcttcgatg gtgtcactta ctattacctg ccctggggaa acgtgaagcc cgtcgtggtc    1980
```

```
ctgagctcct actgggaaga catctcccac cgcattgaga cacagaatca gctgctggga    2040
atcgccgatc ggctggaagc tggcctggag caggtgcatc tggcactgaa ggcccagtgc    2100
tcaaccgaag acgtggatag cctggtcgct cagctgacag acgagctgat cgcaggctgt    2160
tctcagcctc tgggggacat tcacgagacc ccaagtgcca cacatctgga tcagtatctg    2220
taccagctga gaacacacca tctgagtcag atcactgaag ctgcactggc tctgaagctg    2280
ggccactcag agctgcctgc cgctctggaa caggcagagg actggctgct gaggctgcga    2340
gctctggcag aagagcctca gaactctctg ccagacatcg tgatttggat gctgcaggga    2400
gataagaggg tggcctacca gcgcgtccca gctcatcagg tgctgttcag tcgccgaggc    2460
gctaactact gcggaaagaa ttgtggcaaa ctgcagacca tctttctgaa gtatcctatg    2520
gagaaagtgc ctggcgcccg aatgccagtg cagattcggg tcaagctgtg gttcgggctg    2580
agcgtggacg aaaaggagtt taatcagttc gccgaaggaa aactgtccgt ctttgctgag    2640
acatacgaaa acgagactaa gctggccctg gtgggcaatt gggggaccac aggactgacc    2700
tatcccaagt tcagcgacgt gacaggcaag atcaaactgc ctaaagattc cttccggcca    2760
tctgcagggt ggacatgggc aggagactgg tttgtgtgcc ctgaaaagac tctgctgcac    2820
gacatggatg ccgggcatct gtccttcgtg aagaggtct ttgagaacca gactagactg    2880
ccaggcgggc agtggatcta tatgtctgac aactacaccg atgtcaatgg cgagaaggtg    2940
ctgccaaaag acgatattga atgtccctg gggtggaagt gggaggacga agagtggtct    3000
accgatctga atcgggctgt ggacgaacag ggctgggagt acagtatcac aattcccct    3060
gaaagaaagc ccaaacactg ggtgcctgcc gagaaaatgt attacaccca tcgaagaagg    3120
cgatgggtga ggctgcgacg gagagacctg agccagatgg aggccctgaa gcgacaccga    3180
caggcagaag ctgagggaga aggctgggaa tacgcatccc tgtttggctg gaagttccat    3240
ctggagtatc gcaaaactga tgccttcagg cgccgacgat ggagaaggcg aatggaacca    3300
ctggagaaga ccggacctgc agccgtcttt gctctggaag gggcactggg aggcgtgatg    3360
gacgataaaa gcgaggactc aatgagcgtg tccaccctgt cctttggcct gttcccaaag    3420
gcactgggaa ggccaggacc acccttcaac atcacacccc gacgggctag aaggttcttt    3480
ctgagatgca tcatttggaa tactagggac gtgactaaag gtgcttttgg tgatatgtta    3540
gatactcctg atatctacgt gaaagggtgg atgattggat tcgaagagca caagcagaaa    3600
acagacgtgc attatcgctc tctgggggga gaaggaaact ttaattggcg gttcatctt    3660
ccattcgatt acctgcccgc agagcaggtg gctaccattg caaagaaaga tgccttctgg    3720
agactggaca agacagagag caaaatccct gccagggtgg tcttccagat ttgggacaac    3780
gataagtttt ctttcgacga ttttctgggc agtctgcagc tggacctgaa taggatgcct    3840
aagccagcca aaaccgctaa gaaagcatca ctggatcagc tggacgatgc ctttcaccct    3900
gaatggtttg tgagcctgtt cgagcagaag acagtcaaag gctggtggcc atgtgtggca    3960
gaagagggcg agaagaaaat cctggccggg aaactggaaa tgactctgga gattgtggct    4020
gagtctgaac atgaagagag accgcaggg caggggaagg gacgaaccca acatgaatcct    4080
aagctggagg accccagacg acctgatacc tcctttctgt ggttcacctc tccttacaag    4140
acaatgaaat tcatcctgtg gcggagattt cgctgggcca tcattctgtt tatcattctg    4200
ttcattctgc tgctgtttct ggctatcttc atctacgcat ttccaaacta cgctgcaatg    4260
aagctggtga aacccttcag ctga                                          4284
```

<210> SEQ ID NO 3
<211> LENGTH: 3873
<212> TYPE: DNA
<213> ORGANISM: Artificial
<220> FEATURE:
<223> OTHER INFORMATION: Clone_430 No Flag (430)

<400> SEQUENCE: 3

| | | | | | |
|---|---|---|---|---|---|
| atgctgcgag | tctttattct | gtatgccgaa | acgtccaca | cccccgacac | cgacatctct | 60 |
| gatgcttact | gctccgccgt | ctttgccggg | gtcaagaaaa | ggaccaaagt | gatcaagaac | 120 |
| agtgtgaatc | ctgtctggaa | cgagggattc | gaatgggatc | tgaagggcat | tccactggac | 180 |
| caggggtcag | aactgcacgt | ggtcgtgaaa | gaccatgaga | caatgggaag | gaaccgcttc | 240 |
| ctgggcgaag | caaaggtgcc | tctgcgagag | gtcctggcaa | ctccatctct | gagtgccagc | 300 |
| ttcaacgctc | ccctgctgga | tactaagaaa | cagcctaccg | gggcaagcct | ggtgctgcag | 360 |
| gtctcctata | cacctctgcc | aggagcagtg | cctctgttcc | cacctccaac | tccactggaa | 420 |
| cccagcccta | ccctgccaga | cctggatgtc | gtggccgaca | ctggcgggga | ggaagacacc | 480 |
| gaggatcagg | gcctgacagg | ggatgaagct | gagcccttc | tggaccagtc | aggaggcccc | 540 |
| ggagcaccta | ccacacccag | aaagctgcca | agcagacccc | ctccacacta | ccccggcatc | 600 |
| aagcgaaaac | gatcagcacc | aaccagccgg | aagctgctgt | ccgacaaacc | tcagccatca | 660 |
| gaggacaaag | aagatatcga | gagcaacctg | ctgcgaccca | ccggagtcgc | actgcggggc | 720 |
| gcccacttct | gtctgaaagt | gtttcgcgct | gaggacctgc | cccagatgga | cgatgcagtg | 780 |
| atggataatg | tcaagcagat | cttcggcttt | gaaagcaaca | agaaaaatct | ggtggacccc | 840 |
| ttcgtggagg | tctcctttgc | cgggaagatg | ctgtgctcta | agatcctgga | gaaaacagcc | 900 |
| aaccctcagt | ggaaccagaa | tattactctg | ccagctatgt | tccccagcat | gtgtgagaaa | 960 |
| atgcgcatcc | gaatcattga | ctgggataga | ctgacacaca | atgatattgt | ggccactacc | 1020 |
| tatctgtcta | tgagtaagat | ctccgctcca | ggggagaga | ttgaggaaga | gcccgcaggc | 1080 |
| gccgtgaagc | cttctaaagc | cagtgacctg | gacgattacc | tggggtttct | gcctacattc | 1140 |
| ggaccatgct | atatcaacct | gtacgggtcc | ccccggagt | ttactggatt | cccagatccc | 1200 |
| tacacagaac | tgaatactgg | aaagggcgag | ggggtggctt | atcggggcag | actgctgctg | 1260 |
| agtctggaga | ccaagctggt | cgaacattca | gagcagaaag | tggaagacct | gcccgccgac | 1320 |
| gatatcctga | gagtggagaa | gtatctgcgg | agaaggaaat | acagtctgtt | tgcagccttc | 1380 |
| tattcagcca | ccatgctgca | ggatgtcgac | gatgctatcc | agttcgaggt | gagcattggg | 1440 |
| aactacggaa | ataagtttga | catgacatgc | ctgcctctgg | caagtacaac | tcagtattca | 1500 |
| cgggccgtct | tcgatgggtg | tcactactat | tacctgccct | ggggaaacgt | gaagcccgtc | 1560 |
| gtggtcctga | gctcctactg | gaagacatc | tcccaccgca | ttgagacaca | gaatcagctg | 1620 |
| ctgggaatcg | ccgatcggct | ggaagctggc | ctggagcagg | tgcatctggc | actgaaggcc | 1680 |
| cagtgctcaa | ccgaagacgt | ggatagcctg | gtcgctcagc | tgacagacga | gctgatcgca | 1740 |
| ggctgttctc | agcctctggg | ggacattcac | gagaccccaa | gtgccacaca | tctggatcag | 1800 |
| tatctgtacc | agctgagaac | acaccatctg | agtcagatca | ctgaagctgc | actggctctg | 1860 |
| aagctgggcc | actcagagct | gcctgccgct | ctggaacagg | cagaggactg | gctgctgagg | 1920 |
| ctgcgagctc | tggcagaaga | gcctcagaac | tctctgccag | acatcgtgat | ttggatgctg | 1980 |
| cagggagata | agagggtggc | ctaccagcgc | gtcccagctc | atcaggtgct | gttcagtcgc | 2040 |
| cgaggcgcta | actactgcgg | aaagaattgt | ggcaaactgc | agaccatctt | tctgaagtat | 2100 |

```
cctatggaga aagtgcctgg cgcccgaatg ccagtgcaga ttcgggtcaa gctgtggttc    2160
gggctgagcg tggacgaaaa ggagtttaat cagttcgccg aaggaaaact gtccgtcttt    2220
gctgagacat acgaaaacga gactaagctg ccctggtgg gcaattgggg gaccacagga     2280
ctgacctatc ccaagttcag cgacgtgaca ggcaagatca aactgcctaa agattccttc    2340
cggccatctg cagggtggac atgggcagga gactggtttg tgtgccctga aaagactctg    2400
ctgcacgaca tggatgccgg gcatctgtcc ttcgtggaag aggtctttga gaaccagact    2460
agactgccag gcgggcagtg gatctatatg tctgacaact acaccgatgt caatggcgag    2520
aaggtgctgc caaaagacga tattgaatgt cccctggggt ggaagtggga ggacgaagag    2580
tggtctaccg atctgaatcg ggctgtggac gaacagggct gggagtacag tatcacaatt    2640 cccctgaaa gaaagcccaa acactggtg cctgccgaga aatgtatta cacccatcga      2700 agaaggcgat gggtgaggct gcgacggaga gacctgagcc agatggaggc cctgaagcga    2760
caccgacagg cagaagctga gggagaaggc tggaatacg catccctgtt tggctggaag    2820
ttccatctgg agtatcgcaa aactgatgcc ttcaggcgcc gacgatggag aaggcgaatg    2880
gaaccactgg agaagaccgg acctgcagcc gtctttgctc tggaaggggc actgggaggc    2940
gtgatggacg ataaaagcga ggactcaatg agcgtgtcca ccctgtcctt tggcctgttc    3000
ccaaaggcac tggaaggcc aggaccaccc ttcaacatca cacccgacgg gctagaagg     3060 ttctttctga gatgcatcat ttggaatact agggacgtga ttctggacga tctgagcctg    3120
accggggaga agatgtccga tatctacgtg aaagggtgga tgattggatt cgaagagcac    3180
aagcagaaaa cagacgtgca ttatcgctct ctgggggag aaggaaactt taattggcgg     3240
ttcatctttc cattcgatta cctgcccgca gagcaggtgg ctaccattgc aaagaaagat    3300
gccttctgga gactggacaa gacagagagc aaaatccctg ccagggtggt cttccagatt    3360
tgggacaacg ataagttttc tttcgacgat tttctgggca gtctgcagct ggacctgaat    3420
aggatgccta agccagccaa aaccgctaag aaagcatcac tggatcagct ggacgatgcc    3480
tttcaccctg aatggtttgt gagcctgttc gagcagaaga cagtcaaagg ctggtggcca    3540
tgtgtggcag aagagggcga aagaaaatc ctggccggga aactggaaat gactctggag    3600
attgtggctg agtctgaaca tgaagagaga cccgcagggc agggaaggga cgaacccaac    3660
atgaatccta agctggagga ccccagacga cctgatacct cctttctgtg gttcacctct    3720
ccttacaaga caatgaaatt catcctgtgg cggagatttc gctgggccat cattctgttt    3780
atcattctgt tcattctgct gctgtttctg gctatcttca tctacgcatt tccaaactac    3840
gctgcaatga agctggtgaa acccttcagc tga                                 3873
```

<210> SEQ ID NO 4
<211> LENGTH: 4476
<212> TYPE: DNA
<213> ORGANISM: Artificial
<220> FEATURE:
<223> OTHER INFORMATION: Clone_342 No Flag (426)

<400> SEQUENCE: 4

```
atgctgagag tctttattct gtacgctgaa aacgtgcata ccctgatac cgacattagt      60 gacgcttatt gctccgctgt gttcgccggc gtcaagaaac gcacaaaagt gatcaagaac    120
agcgtgaatc ctgtctggaa cgaggggttc gaatgggatc tgaagggaat cccactggac    180
cagggctccg aactgcacgt ggtcgtgaaa gaccatgaga caatgggcag gaaccgcttc    240
```

```
ctgggagagg ctaaggtgcc tctgcgggaa gtcctggcaa caccatctct gagtgcaagc    300
ttcaacgccc ccctgctgga tactaagaaa cagcctaccg gcgcttcact ggtgctgcag    360
gtcagctata cccctctgcc aggagcagtg ccactgttcc cacctccaac tccactggaa    420
ccaagcccta ccctgcccga cctggatgtc gtggccgaca ctggcgggga ggaagacacc    480
gaggatcagg ggctgacagg agatgaagcc gagccttttc tggaccagag cggcggacca    540
ggagctccaa ccacacctcg caagctgcca tctcgacccc ctccacatta ccccggaatc    600
aagcgaaaac ggtcagcccc aactagccgc aagctgctga gtgacaaacc tcagtcaaac    660
ctgctgcgac caaccggggt cgctctgcga ggagcacact tctgcctgaa agtgtttcgg    720
gccgaggacc tgccccagat ggacgatgct gtgatggata atgtcaagca gatcttcgga    780
ttcgaatcta acaagaaaaa tctggtggat cctttcgtgg aggtctcctt tgccggcaag    840
atgctgtgct ctaagattct ggagaaaact gcaaacccac agtggaacca gaatatcacc    900
ctgccagcca tgttcccctc tatgtgtgag aaaatgagaa ttaggatcat tgactgggat    960
agactgaccc acaatgacat cgtggcaact acctatctga gcatgtccaa gattagcgcc   1020
cctgggggag agatcgagga agagcctgct ggcgcagtga agccatctaa agccagtgac   1080
ctggacgatt acctgggctt tctgcctact ttcgggccat gttatatcaa cctgtacggg   1140
agcccaagag agtttaccgg attcccagat ccctacacag agctgaatac tggcaagggg   1200
gaaggagtgg cttatcgcgg ccgactgctg ctgagtctgg agaccaagct ggtcgagcac   1260
tcagaacaga agtggaaga cctgccagcc gacgatatcc tgagggtgga gaagtatctg   1320
cggagaagga atacagcct gtttgccgct ttctattccg caacaatgct gcaggatgtc   1380
gacgatgcca ttcagttcga ggtgtctatc ggcaactacg ggaataagtt tgacatgact   1440
tgcctgcctc tggctagcac aactcagtat tccagagcag tcttcgatgg atgtcactac   1500
tattacctgc cctggggcaa cgtgaagcct gtcgtggtcc tgagctccta ctgggaggac   1560
attagccata gaatcgaaac ccagaatcag ctgctgggaa tcgcagatag gctgaggca   1620 ggactggaac aggtgcacct ggctctgaag gcacagtgct ccacagaaga cgtggattct   1680
ctggtcgccc agctgactga cgagctgatt gctggatgtt ctcagcctct gggcgacatc   1740
cacgagaccc caagtgccac acatctggat cagtatctgt accagctgag gacacaccat   1800
ctgagtcaga tcactgaagc agccctggcc ctgaagctgg ccattcaga gctgccgct   1860 gcactggagc aggctgaaga ctggctgctg cggctgagag ccctggctga agagccacag   1920
aacagcctgc ccgacatcgt gatttggatg ctgcaggggg ataagcgggt ggcataccag   1980
agagtccctg cacaccaggt gctgttctcc cgccgaggag ctaactactg cgggaagaat   2040
tgtgaaaaac tgcagaccat tttctgaag tatcctatgg agaaagtgcc aggagcccga   2100
atgcccgtgc agatccgggt caagctgtgg ttcggcctga gcgtggacga aaaggagttt   2160
aatcagttcg cagaggggaa actgtccgtc tttgccgaaa catacgaaaa cgagactaag   2220
ctggccctgg tgggaaattg gggcaccaca gggctgacct atcccaagtt ctccgacgtg   2280
acaggcaaga tcaaactgcc aaaagattcc ttcagaccct ctgctggctg gacttgggca   2340
ggggactggt ttgtgtgccc agaaaagacc ctgctgcacg acatggatgc cggccatctg   2400
agtttcgtgg aagaggtctt tgagaaccag accaggctgc aggaggaca gtggatctac   2460 atgtcagaca actacacaga tgtcaatgga gagaaggtgc tgcccaaaga cgatatcgag   2520
tgtcctctgg gctggaagtg ggaagacgaa gagtggtcta cagatctgaa tcgcgcagtg   2580
gacgagcagg gctgggaata cagtatcact attccccctg aacggaagcc taaacactgg   2640
```

```
gtgccagccg agaaaatgta ttacacccat cgaagaaggc gatgggtgcg cctgcgacgg    2700
agagacctgt ctcagatgga ggccctgaag aggcatcgac aggcagaagc agagggagaa    2760
ggatgggaat acgctagtct gtttggctgg aagttccacc tggagtatcg gaaaacagat    2820
gcattcaggc gccgacgatg gagaaggcga atggagcctc tggaaaaaac tgggccagcc    2880
gctgtctttg ccctggaagg agctctggga ggcgtgatgg acgataagag cgaggactct    2940
atgagtgtgt caactctgtc cttcggcctg gtcaggatct acattgtgcg cgcctttggg    3000
ctgcagccaa aggatcccaa cggaaaatgc gaccccctaca tcaaaatttc catcggcaag    3060
aaaagcgtct ccgaccagga taattatatc ccctgcaccc tggagcctgt gtttgggaag    3120
atgttcgaac tgacttgtac cctgcctctg gagaaggacc tgaaaattac cctgtatgac    3180
tacgatctgt gtccaagga cgagaaaatc ggggaaacag tggtcgatct ggagaacaga    3240
ctgctgtcta agttcggagc tagatgcgga ctgccacaga cctattgtgt gtcaggacct    3300
aatcagtgga gagatcagct gaggcccagc cagctgctgc acctgttctg tcagcagcat    3360
agggtgaagg cccctgtcta ccgaacagat agagtgatgt ttcaggacaa agagtatagc    3420
attgaagaga tcgaagccgg ccgcattcct aacccacacc tgggaccgt cgaagagcga    3480 ctggctctgc atgtgctgca gcagcaggga ctggtgccag agcacgtcga atctagaccc    3540
ctgtacagtc ctctgcagcc agacatcgag cagggcaagc tgcagatgtg ggtggatctg    3600
ttccccaaag cactgggaag gcctggccca cccttaaca ttacacccg acgggccaga    3660 aggttctttc tgcgctgcat catttggaat acccggacg tgatcctgga cgatctgtct    3720
ctgacaggcg agaagatgag tgatatctac gtgaaaggat ggatgatcgg cttcgaagag    3780
cacaagcaga aaaccgacgt gcattatcgc agcctggggg gagaagggaa ctttaattgg    3840
cggttcattt ttccattcga ttacctgccc gctgagcagg tggccacaat cgctaagaaa    3900
gatgcattct ggagactgga caagactgag tccaaaattc ccgccagggt ggtcttccag    3960
atctgggaca acgataagtt ttcattcgac gattttctgg gcagcctgca gctggacctg    4020
aatcgcatgc ccaagcctgc aaaaacagcc aagaaagctt cactggatca gctggacgat    4080
gcctttcatc cagagtggtt tgtgagcctg ttcaacaga agactgtcaa aggatggtgg    4140
ccatgcgtgg ctgaagaggg agagaagaaa attctggcag ggaaactgga gatgaccctg    4200
gaaatcgtgg ccgagagcga acacgaagag agacctgctg acagggcag ggacgaaccc    4260 aacatgaatc ctaagctgga ggaccccaga cgacctgata ccagttttct gtggttcacc    4320
tcaccataca agacaatgaa attcattctg tggcggagat ttcggtgggc catcattctg    4380
tttatcattc tgttcatcct gctgctgttt ctggccattt tcatctatgc ttttccaaac    4440
tacgcagcca tgaagctggt gaaacccttc tcctga                             4476
```

<210> SEQ ID NO 5
<211> LENGTH: 4287
<212> TYPE: DNA
<213> ORGANISM: Artificial
<220> FEATURE:
<223> OTHER INFORMATION: Clone_425 No Flag (425)

<400> SEQUENCE: 5

```
atgctgcgag tctttattct gtatgccgaa aacgtccaca ccccccgacac cgacatctct      60 gatgcttact gctccgccgt cttttgccggg gtcaagaaaa ggaccaaagt gatcaagaac    120
agtgtgaatc ctgtctggaa cgagggattc gaatgggatc tgaagggcat tccactggac    180
```

```
caggggtcag aactgcacgt ggtcgtgaaa gaccatgaga caatgggaag gaaccgcttc    240
ctgggcgaag caaaggtgcc tctgcgagag gtcctggcaa ctccatctct gagtgccagc    300
ttcaacgctc ccctgctgga tactaagaaa cagcctaccg gggcaagcct ggtgctgcag    360
gtctcctata cacctctgcc aggagcagtg cctctgttcc cacctccaac tccactggaa    420
cccagcccta ccctgccaga cctggatgtc gtggccgaca ctggcgggga ggaagacacc    480
gaggatcagg gcctgacagg ggatgaagct gagccctttc tggaccagtc aggaggcccc    540
ggagcaccta ccacacccag aaagctgcca agcagacccc ctccacacta ccccggcatc    600
aagcgaaaac gatcagcacc aaccagccgg aagctgctgt ccgacaaacc tcaggatttt    660
cagatccgcg tgcaggtcat tgagggccga cagctgcctg gggtcaacat caagccagtc    720
gtgaaagtga ctgccgctgg acagactaag agaaccagga ttcataaagg caactccccc    780
ctgttcaatg agaccctgtt ctttaatctg tttgattctc ccggcgaact gttcgacgag    840
cctatcttta ttactgtcgt ggatagcaga tccctgagga ccgacgctct gctgggagaa    900
ttcagaatgg acgtgggcac tatctatcgc gagccccgac acgcctacct gaggaaatgg    960
ctgctgctgt ctgatcctga cgattttagt gccggagctc gcggctacct gaagacctct   1020
ctgtgcgtgc tgggaccagg ggatgaagca ccactgagga ggaaggaccc atcagaggac   1080
aaagaagata tcgagagcaa cctgctgcga cccaccggag tcgcactgcg gggcgcccac   1140
ttctgtctga agtgtttcg cgctgaggac ctgcccagga tggacgatgc agtgatggat   1200
aatgtcaagc agatcttcgg ctttgaaagc aacaagaaaa atctggtgga ccccttcgtg   1260
gaggtctcct tgccgggaa gatgctgtgc tctaagatcc tggagaaaac agccaaccct   1320
cagtggaacc agaatattac tctgccagct atgttcccca gcatgtgtga aaaatgcgc   1380
atccgaatca ttgactggga tagactgaca cacaatgata ttgtggccac tacctatctg   1440
tctatgagta agatctccgc tccaggggga gagattgagg aagagcccgc aggcgccgtg   1500
aagccttcta agccagtga cctggacgat tacctgggt ttctgcctac attcggacca   1560
tgctatatca acctgtacgg gtccccccgg gagtttactg gattcccaga tccctacaca   1620
gaactgaata ctgaaaaggg cgaggggggtg gcttatcggg gcagactgct gctgagtctg   1680
gagaccaagc tggtcgaaca ttcagagcag aaagtggaag acctgcccgc cgacgatatc   1740
ctgagagtgg agaagtatct gcggagaagg aaatacagtc tgtttgcagc cttctattca   1800
gccaccatgc tgcaggatgt cgacgatgct atccagttcg aggtgagcat tgggaactac   1860
ggaaataagt ttgacatgac atgcctgcct ctggcaagta caactcagta ttcacgggcc   1920
gtcttcgatg ggtgtcacta ctattacctg ccctggggaa acgtgaagcc cgtcgtggtc   1980
ctgagctcct actgggaaga catctcccac cgcattgaga cacagaatca gctgctggga   2040
atcgccgatc ggctggaagc tggcctggag caggtgcatc tggcactgaa ggcccagtgc   2100
tcaaccgaag acgtggatag cctggtcgct cagctgacag acgagctgat cgcaggctgt   2160
tctcagcctc tggggacat tcacgagacc ccaagtgcca cacatctgga tcagtatctg   2220
taccagctga gaacacacca tctgagtcag atcactgaag ctgcactggc tctgaagctg   2280
ggccactcag agctgcctgc cgctctggaa caggcagagg actggctgct gaggctgcga   2340
gctctggcag aagagcctca gaactctctg ccagacatcg tgatttggat gctgcaggga   2400
gataagaggg tggcctacca gcgcgtccca gctcatcagg tgctgttcag tcgccgaggc   2460
gctaactact gcggaaagaa ttgtggcaaa ctgcagacca tctttctgaa gtatcctatg   2520
gagaaagtgc ctggcgcccg aatgccagtg cagattcggg tcaagctgtg gttcgggctg   2580
```

-continued

```
agcgtggacg aaaaggagtt taatcagttc gccgaaggaa aactgtccgt ctttgctgag    2640
acatacgaaa acgagactaa gctggccctg gtgggcaatt gggggaccac aggactgacc    2700
tatcccaagt tcagcgacgt gacaggcaag atcaaactgc ctaaagattc cttccggcca    2760
tctgcagggt ggacatgggc aggagactgg tttgtgtgcc ctgaaaagac tctgctgcac    2820
gacatggatg ccgggcatct gtccttcgtg aagaggtct ttgagaacca gactagactg     2880
ccaggcgggc agtggatcta tatgtctgac aactacaccg atgtcaatgg cgagaaggtg    2940
ctgccaaaag acgatattga atgtcccctg ggtggaagt gggaggacga agagtggtct     3000
accgatctga atcgggctgt ggacgaacag ggctgggagt acagtatcac aattccccct    3060
gaaagaaagc ccaaacactg ggtgcctgcc gagaaatgt attcacccca tcgaagaagg     3120
cgatgggtga ggctgcgacg gagagacctg agccagatgg aggccctgaa gcacaccga     3180
caggcagaag ctgagggaga aggctgggaa tacgcatccc tgtttggctg aagttccat    3240
ctggagtatc gcaaaactga tgccttcagg cgccgacgat ggagaaggcg aatggaacca    3300
ctggagaaga ccggacctgc agccgtcttt gctctggaag gggcactggg aggcgtgatg    3360
gacgataaaa gcgaggactc aatgagcgtg tccaccctgt cctttggcct gttcccaaag    3420
gcactgggaa ggccaggacc acccttcaac atcacacccc gacgggctag aaggttcttt    3480
ctgagatgca tcatttggaa tactagggac gtgattctgg acgatctgag cctgaccggg    3540
gagaagatgt ccgatatcta cgtgaaaggg tggatgattg gattcgaaga gcacaagcag    3600
aaaacagacg tgcattatcg ctctctgggg ggagaaggaa actttaattg gcggttcatc    3660
tttccattcg attacctgcc cgcagagcag gtggctacca ttgcaaagaa agatgccttc    3720
tggagactgg acaagacaga gagcaaaatc cctgccaggg tggtcttcca gatttgggac    3780
aacgataagt tttctttcga cgattttctg ggcagtctgc agctggacct gaataggatg    3840
cctaagccag ccaaaaccgc taagaaagca tcactggatc agctggacga tgcctttcac    3900
cctgaatggt ttgtgagcct gttcgagcag aagacagtca aaggctggtg gccatgtgtg    3960
gcagaagagg gcgagaagaa aatcctggcc gggaaactgg aaatgactct ggagattgtg    4020
gctgagtctg aacatgaaga gagacccgca gggcaggaa gggacgaacc caacatgaat    4080
cctaagctgg aggaccccag acgacctgat acctcctttc tgtggttcac ctctccttac    4140
aagacaatga aattcatcct gtggcggaga tttcgctggg ccatcattct gtttatcatt    4200
ctgttcattc tgctgctgtt tctggctatc ttcatctacg catttccaaa ctacgctgca    4260
atgaagctgg tgaaacccct cagctga                                        4287
```

<210> SEQ ID NO 6
<211> LENGTH: 1499
<212> TYPE: PRT
<213> ORGANISM: Artificial
<220> FEATURE:
<223> OTHER INFORMATION: 318 No flag (433)

<400> SEQUENCE: 6

Met Leu Arg Val Phe Ile Leu Tyr Ala Glu Asn Val His Thr Pro Asp
1               5                   10                  15

Thr Asp Ile Ser Asp Ala Tyr Cys Ser Ala Val Phe Ala Gly Val Lys
            20                  25                  30

Lys Arg Thr Lys Val Ile Lys Asn Ser Val Asn Pro Val Trp Asn Glu
        35                  40                  45

Gly Phe Glu Trp Asp Leu Lys Gly Ile Pro Leu Asp Gln Gly Ser Glu

```
                  50                  55                  60
Leu His Val Val Lys Asp His Glu Thr Met Gly Arg Asn Arg Phe
 65                  70                  75                  80

Leu Gly Glu Ala Lys Val Pro Leu Arg Glu Val Leu Ala Thr Pro Ser
                     85                  90                  95

Leu Ser Ala Ser Phe Asn Ala Pro Leu Leu Asp Thr Lys Lys Gln Pro
                    100                 105                 110

Thr Gly Ala Ser Leu Val Leu Gln Val Ser Tyr Thr Asp Leu Asp Val
                    115                 120                 125

Val Ala Asp Thr Gly Glu Glu Asp Thr Glu Asp Gln Gly Leu Thr Pro
130                 135                 140

Phe Leu Asp Gln Ser Gly Gly Pro Arg Lys Leu Pro Ser Arg Gly Ile
145                 150                 155                 160

Lys Arg Lys Arg Ser Ile Arg Val Gln Val Ile Glu Gly Arg Gln Leu
                    165                 170                 175

Pro Gly Val Asn Ile Lys Pro Val Val Lys Val Thr Ala Ala Gly Gln
                    180                 185                 190

Thr Lys Arg Thr Arg Ile His Lys Gly Asn Ser Pro Leu Phe Asn Glu
                    195                 200                 205

Thr Leu Phe Phe Asn Leu Phe Asp Ser Pro Gly Glu Leu Phe Asp Glu
                    210                 215                 220

Pro Ile Phe Ile Thr Val Val Asp Ser Arg Ser Leu Arg Thr Asp Ala
225                 230                 235                 240

Leu Leu Gly Glu Phe Arg Met Asp Val Gly Thr Ile Tyr Arg Glu Pro
                    245                 250                 255

Arg His Ala Tyr Leu Arg Lys Trp Leu Leu Leu Ser Asp Pro Asp Asp
                    260                 265                 270

Phe Ser Ala Gly Ala Arg Gly Tyr Leu Lys Thr Ser Leu Cys Val Leu
                    275                 280                 285

Gly Pro Gly Asp Glu Ala Pro Leu Glu Arg Lys Asp Pro Ser Glu Asp
                    290                 295                 300

Lys Glu Asp Ile Glu Ser Asn Leu Leu Arg Pro Thr Gly Val Ala Leu
305                 310                 315                 320

Arg Gly Ala His Phe Cys Leu Lys Val Phe Arg Ala Glu Asp Leu Pro
                    325                 330                 335

Gln Met Asp Asp Ala Val Met Asp Asn Val Lys Gln Ile Phe Gly Phe
                    340                 345                 350

Glu Ser Asn Lys Lys Asn Leu Val Asp Pro Phe Val Glu Val Ser Phe
                    355                 360                 365

Ala Gly Lys Met Leu Cys Ser Lys Ile Leu Glu Lys Thr Ala Asn Pro
370                 375                 380

Gln Trp Asn Gln Asn Ile Thr Leu Pro Ala Met Phe Pro Ser Met Cys
385                 390                 395                 400

Glu Lys Met Arg Ile Arg Ile Ile Asp Trp Asp Arg Leu Thr His Asn
                    405                 410                 415

Asp Ile Val Ala Thr Thr Tyr Leu Ser Met Ser Lys Ile Ser Ala Pro
                    420                 425                 430

Gly Gly Glu Ile Glu Glu Pro Ala Gly Ala Val Lys Pro Ser Lys
                    435                 440                 445

Ala Ser Asp Leu Asp Asp Tyr Leu Gly Phe Leu Glu His Ser Glu Gln
                    450                 455                 460

Lys Val Glu Asp Leu Pro Ala Asp Asp Ile Leu Arg Val Glu Lys Tyr
465                 470                 475                 480
```

```
Leu Arg Arg Arg Lys Tyr Ser Leu Phe Ala Ala Phe Tyr Ser Ala Thr
                485                 490                 495

Met Leu Gln Asp Val Asp Ala Ile Gln Phe Glu Val Ser Ile Gly
            500                 505                 510

Asn His Arg Ile Glu Thr Gln Asn Gln Leu Leu Gly Ile Ala Asp Arg
            515                 520                 525

Leu Glu Ala Gly Leu Glu Gln Val His Leu Ala Leu Lys Ala Gln Cys
        530                 535                 540

Ser Thr Glu Asp Val Asp Ser Leu Val Ala Gln Leu Thr Asp Glu Leu
545                 550                 555                 560

Ile Ala Gly Cys Ser Gln Pro Leu Gly Asp Ile His Glu Thr Pro Ser
                565                 570                 575

Ala Thr His Leu Asp Gln Tyr Leu Tyr Gln Leu Arg Thr His His Leu
            580                 585                 590

Ser Gln Ile Thr Glu Ala Ala Leu Ala Leu Lys Leu Gly His Ser Glu
        595                 600                 605

Leu Pro Ala Ala Leu Glu Gln Ala Glu Asp Trp Leu Leu Arg Leu Arg
610                 615                 620

Ala Leu Lys Leu Gln Thr Ile Phe Leu Lys Tyr Pro Met Glu Lys Val
625                 630                 635                 640

Pro Gly Ala Arg Met Pro Val Gln Ile Arg Val Lys Leu Trp Phe Gly
                645                 650                 655

Leu Ser Val Asp Glu Lys Glu Phe Asn Gln Phe Ala Glu Gly Lys Leu
            660                 665                 670

Ser Val Phe Ala Glu Thr Tyr Glu Asn Glu Thr Lys Leu Ala Leu Val
        675                 680                 685

Met Asp Ala Gly His Leu Ser Phe Val Glu Glu Val Phe Glu Asn Gln
690                 695                 700

Thr Arg Leu Pro Gly Gly Gln Trp Ile Tyr Met Ser Asp Asn Tyr Thr
705                 710                 715                 720

Asp Val Asn Gly Glu Lys Val Leu Pro Lys Asp Ile Glu Cys Pro
                725                 730                 735

Leu Gly Trp Lys Trp Glu Asp Glu Glu Trp Ser Thr Asp Leu Asn Arg
            740                 745                 750

Ala Val Asp Glu Gln Gly Trp Glu Tyr Ser Ile Thr Ile Pro Pro Glu
        755                 760                 765

Arg Lys Pro Lys His Trp Val Pro Ala Glu Lys Met Tyr Tyr Thr His
770                 775                 780

Arg Arg Arg Arg Trp Val Arg Leu Arg Arg Asp Leu Ser Gln Met
785                 790                 795                 800

Glu Ala Leu Lys Arg His Arg Gln Ala Glu Ala Glu Gly Glu Gly Trp
                805                 810                 815

Glu Tyr Ala Ser Leu Phe Gly Trp Lys Phe His Leu Glu Tyr Arg Lys
            820                 825                 830

Thr Asp Ala Phe Arg Arg Arg Trp Arg Arg Met Glu Pro Leu
        835                 840                 845

Glu Lys Thr Pro Ala Ile His His Ile Pro Gly Phe Glu Val Gln Glu
850                 855                 860

Thr Ser Arg Ile Leu Asp Glu Ser Glu Asp Thr Asp Leu Pro Tyr Pro
865                 870                 875                 880

Pro Pro Gln Arg Glu Ala Asn Ile Tyr Met Val Pro Gln Asn Ile Lys
                885                 890                 895
```

```
Pro Ala Leu Gln Arg Thr Ala Ile Glu Ile Leu Ala Trp Gly Leu Arg
            900                 905                 910

Asn Met Lys Ser Tyr Gln Leu Ala Asn Ile Ser Ser Pro Ser Leu Val
        915                 920                 925

Val Glu Cys Gly Gly Gln Thr Val Gln Ser Cys Val Ile Arg Asn Leu
    930                 935                 940

Arg Lys Asn Pro Asn Phe Asp Ile Cys Thr Leu Phe Met Glu Val Met
945                 950                 955                 960

Leu Pro Arg Glu Glu Leu Tyr Cys Pro Pro Ile Thr Val Lys Val Ile
                965                 970                 975

Asp Asn Arg Gln Phe Gly Arg Arg Pro Val Val Gly Gln Cys Thr Ile
            980                 985                 990

Arg Ser Leu Glu Ser Phe Leu Cys  Asp Pro Tyr Ser Ala  Glu Ser Pro
        995                 1000                1005

Ser Pro  Gln Gly Gly Pro  Asp Val Ser Leu Leu  Ser Pro Gly
    1010             1015                1020

Glu Asp  Val Leu Ile Asp  Ile Asp Lys Glu Pro  Glu Lys Asp
    1025             1030                1035

Phe Asp  Thr Leu Lys Val Tyr  Asp Thr Gln Leu Glu  Asn Val Glu
    1040             1045                 1050

Ala Phe  Glu Gly Asn Thr Phe  Lys Leu Tyr Arg Gly  Lys Thr Asp
    1055             1060                 1065

Pro Ser  Val Ile Gly Glu Phe  Lys Gly Leu Leu Val  Arg Ile Tyr
    1070             1075                 1080

Ile Val  Arg Ala Phe Gly Leu  Gln Pro Lys Asp Pro  Asn Gly Lys
    1085             1090                 1095

Cys Asp  Pro Tyr Ile Lys Ile  Ser Ile Gly Lys Lys  Ser Val Ser
    1100             1105                 1110

Asp Gln  Asp Asn Tyr Ile Pro  Cys Thr Leu Glu Pro  Val Phe Gly
    1115             1120                 1125

Lys Met  Phe Glu Leu Thr Cys  Thr Leu Pro Leu Glu  Lys Asp Leu
    1130             1135                 1140

Lys Ile  Thr Leu Tyr Asp Tyr  Asp Leu Leu Ser Lys  Asp Glu Lys
    1145             1150                 1155

Ile Gly  Glu Thr Val Val Asp  Leu Glu Asn Arg Leu  Leu Ser Lys
    1160             1165                 1170

Phe Gly  Ala Arg Cys Gly Leu  Pro Gln Thr Tyr Cys  Val Ser Gly
    1175             1180                 1185

Pro Asn  Gln Trp Arg Asp Gln  Leu Thr Gln Asp Lys  Glu Tyr Ser
    1190             1195                 1200

Ile Glu  Glu Ile Glu Ala Gly  Arg Ile Pro Asn Pro  Glu Glu Arg
    1205             1210                 1215

Leu Ala  Leu His Val Leu Gln  Gln Gln Gly Leu Val  Pro Glu His
    1220             1225                 1230

Val Lys  Ala Leu Gly Arg Pro  Gly Pro Pro Phe Asn  Ile Thr Pro
    1235             1240                 1245

Arg Arg  Ala Arg Arg Phe Leu  Arg Cys Ile Ile  Trp Asn Thr
    1250             1255                 1260

Arg Asp  Val Ile Leu Asp Asp  Leu Ser Leu Thr Gly  Glu Lys Met
    1265             1270                 1275

Ser Asp  Ile Tyr Val Lys Gly  Trp Met Ile Gly Phe  Glu Glu His
    1280             1285                 1290

Lys Gln  Lys Thr Asp Val His  Tyr Arg Ser Leu Gly  Gly Glu Gly
```

-continued

```
                1295                1300                1305

Asn Phe Asn Trp Arg Phe Ile Phe Pro Phe Asp Tyr Leu Pro Ala
    1310                1315                1320

Glu Gln Val Cys Thr Ile Ala Lys Lys Asp Ala Phe Trp Arg Leu
1325                1330                1335

Asp Lys Thr Glu Ser Lys Ile Pro Ala Arg Val Val Phe Gln Ile
    1340                1345                1350

Trp Asp Asn Asp Lys Phe Ser Phe Asp Asp Phe Leu Gly Ser Leu
    1355                1360                1365

Gln Leu Asp Leu Asn Arg Met Pro Lys Pro Ala Lys Thr Ala Lys
1370                1375                1380

Lys Cys Ser Leu Asp Gln Leu Asp Asp Ala Phe His Pro Glu Trp
    1385                1390                1395

Phe Val Ser Leu Phe Glu Gln Lys Thr Val Lys Gly Trp Trp Pro
    1400                1405                1410

Cys Val Ala Glu Glu Gly Glu Lys Lys Ile Leu Ala Gly Lys Leu
    1415                1420                1425

Glu Met Thr Leu Glu Ile Val Ala Glu Arg Pro Ala Gly Pro Arg
1430                1435                1440

Arg Pro Asp Thr Ser Phe Leu Trp Phe Thr Ser Lys Phe Ile Leu
    1445                1450                1455

Trp Arg Arg Phe Arg Trp Ala Ile Ile Leu Phe Ile Ile Leu Phe
    1460                1465                1470

Ile Leu Leu Leu Phe Leu Ala Ile Phe Ile Tyr Ala Phe Pro Asn
    1475                1480                1485

Tyr Ala Ala Met Lys Leu Val Lys Pro Phe Ser
    1490                1495

<210> SEQ ID NO 7
<211> LENGTH: 1427
<212> TYPE: PRT
<213> ORGANISM: Artificial
<220> FEATURE:
<223> OTHER INFORMATION: 431 No Flag (431)

<400> SEQUENCE: 7

Met Leu Arg Val Phe Ile Leu Tyr Ala Glu Asn Val His Thr Pro Asp
1               5                   10                  15

Thr Asp Ile Ser Asp Ala Tyr Cys Ser Ala Val Phe Ala Gly Val Lys
                20                  25                  30

Lys Arg Thr Lys Val Ile Lys Asn Ser Val Asn Pro Val Trp Asn Glu
            35                  40                  45

Gly Phe Glu Trp Asp Leu Lys Gly Ile Pro Leu Asp Gln Gly Ser Glu
        50                  55                  60

Leu His Val Val Lys Asp His Glu Thr Met Gly Arg Asn Arg Phe
65              70                  75                  80

Leu Gly Glu Ala Lys Val Pro Leu Arg Glu Val Leu Ala Thr Pro Ser
                85                  90                  95

Leu Ser Ala Ser Phe Asn Ala Pro Leu Leu Asp Thr Lys Lys Gln Pro
            100                 105                 110

Thr Gly Ala Ser Leu Val Leu Gln Val Ser Tyr Thr Pro Leu Pro Gly
        115                 120                 125

Ala Val Pro Leu Phe Pro Pro Thr Pro Leu Glu Pro Ser Pro Thr
    130                 135                 140

Leu Pro Asp Leu Asp Val Val Ala Asp Thr Gly Gly Glu Glu Asp Thr
```

```
            145                 150                 155                 160
        Glu Asp Gln Gly Leu Thr Gly Asp Glu Ala Glu Pro Phe Leu Asp Gln
                        165                 170                 175

Ser Gly Gly Pro Gly Ala Pro Thr Thr Pro Arg Lys Leu Pro Ser Arg
                        180                 185                 190

Pro Pro Pro His Tyr Pro Gly Ile Lys Arg Lys Arg Ser Ala Pro Thr
                        195                 200                 205

Ser Arg Lys Leu Leu Ser Asp Lys Pro Gln Asp Phe Gln Ile Arg Val
                        210                 215                 220

Gln Val Ile Glu Gly Arg Gln Leu Pro Gly Val Asn Ile Lys Pro Val
        225                 230                 235                 240

Val Lys Val Thr Ala Ala Gly Gln Thr Lys Arg Thr Arg Ile His Lys
                        245                 250                 255

Gly Asn Ser Pro Leu Phe Asn Glu Thr Leu Phe Phe Asn Leu Phe Asp
                        260                 265                 270

Ser Pro Gly Glu Leu Phe Asp Glu Pro Ile Phe Ile Thr Val Val Asp
                        275                 280                 285

Ser Arg Ser Leu Arg Thr Asp Ala Leu Leu Gly Glu Phe Arg Met Asp
                        290                 295                 300

Val Gly Thr Ile Tyr Arg Glu Pro Arg His Ala Tyr Leu Arg Lys Trp
        305                 310                 315                 320

Leu Leu Leu Ser Asp Pro Asp Asp Phe Ser Ala Gly Ala Arg Gly Tyr
                        325                 330                 335

Leu Lys Thr Ser Leu Cys Val Leu Gly Pro Gly Asp Glu Ala Pro Leu
                        340                 345                 350

Glu Arg Lys Asp Pro Ser Glu Asp Lys Glu Asp Ile Glu Ser Asn Leu
                        355                 360                 365

Leu Arg Pro Thr Gly Val Ala Leu Arg Gly Ala His Phe Cys Leu Lys
                        370                 375                 380

Val Phe Arg Ala Glu Asp Leu Pro Gln Met Asp Asp Ala Val Met Asp
        385                 390                 395                 400

Asn Val Lys Gln Ile Phe Gly Phe Glu Ser Asn Lys Lys Asn Leu Val
                        405                 410                 415

Asp Pro Phe Val Glu Val Ser Phe Ala Gly Lys Met Leu Cys Ser Lys
                        420                 425                 430

Ile Leu Glu Lys Thr Ala Asn Pro Gln Trp Asn Gln Asn Ile Thr Leu
                        435                 440                 445

Pro Ala Met Phe Pro Ser Met Cys Glu Lys Met Arg Ile Arg Ile Ile
                        450                 455                 460

Asp Trp Asp Arg Leu Thr His Asn Asp Ile Val Ala Thr Thr Tyr Leu
        465                 470                 475                 480

Ser Met Ser Lys Ile Ser Ala Pro Gly Gly Glu Ile Glu Glu Glu Pro
                        485                 490                 495

Ala Gly Ala Val Lys Pro Ser Lys Ala Ser Asp Leu Asp Asp Tyr Leu
                        500                 505                 510

Gly Phe Leu Pro Thr Phe Gly Pro Cys Tyr Ile Asn Leu Tyr Gly Ser
                        515                 520                 525

Pro Arg Glu Phe Thr Gly Phe Pro Asp Pro Tyr Thr Glu Leu Asn Thr
                        530                 535                 540

Gly Lys Gly Glu Gly Val Ala Tyr Arg Gly Arg Leu Leu Leu Ser Leu
        545                 550                 555                 560

Glu Thr Lys Leu Val Glu His Ser Glu Gln Lys Val Glu Asp Leu Pro
                        565                 570                 575
```

Ala Asp Asp Ile Leu Arg Val Glu Lys Tyr Leu Arg Arg Lys Tyr
            580                 585                 590

Ser Leu Phe Ala Ala Phe Tyr Ser Ala Thr Met Leu Gln Asp Val Asp
            595                 600                 605

Asp Ala Ile Gln Phe Glu Val Ser Ile Gly Asn Tyr Gly Asn Lys Phe
    610                 615                 620

Asp Met Thr Cys Leu Pro Leu Ala Ser Thr Thr Gln Tyr Ser Arg Ala
625                 630                 635                 640

Val Phe Asp Gly Cys His Tyr Tyr Leu Pro Trp Gly Asn Val Lys
                645                 650                 655

Pro Val Val Val Leu Ser Ser Tyr Trp Glu Asp Ile Ser His Arg Ile
            660                 665                 670

Glu Thr Gln Asn Gln Leu Leu Gly Ile Ala Asp Arg Leu Glu Ala Gly
            675                 680                 685

Leu Glu Gln Val His Leu Ala Leu Lys Ala Gln Cys Ser Thr Glu Asp
            690                 695                 700

Val Asp Ser Leu Val Ala Gln Leu Thr Asp Glu Leu Ile Ala Gly Cys
705                 710                 715                 720

Ser Gln Pro Leu Gly Asp Ile His Glu Thr Pro Ser Ala Thr His Leu
                725                 730                 735

Asp Gln Tyr Leu Tyr Gln Leu Arg Thr His His Leu Ser Gln Ile Thr
            740                 745                 750

Glu Ala Ala Leu Ala Leu Lys Leu Gly His Ser Glu Leu Pro Ala Ala
            755                 760                 765

Leu Glu Gln Ala Glu Asp Trp Leu Leu Arg Leu Arg Ala Leu Ala Glu
            770                 775                 780

Glu Pro Gln Asn Ser Leu Pro Asp Ile Val Ile Trp Met Leu Gln Gly
785                 790                 795                 800

Asp Lys Arg Val Ala Tyr Gln Arg Val Pro Ala His Gln Val Leu Phe
                805                 810                 815

Ser Arg Arg Gly Ala Asn Tyr Cys Gly Lys Asn Cys Gly Lys Leu Gln
                820                 825                 830

Thr Ile Phe Leu Lys Tyr Pro Met Glu Lys Val Pro Gly Ala Arg Met
            835                 840                 845

Pro Val Gln Ile Arg Val Lys Leu Trp Phe Gly Leu Ser Val Asp Glu
850                 855                 860

Lys Glu Phe Asn Gln Phe Ala Glu Gly Lys Leu Ser Val Phe Ala Glu
865                 870                 875                 880

Thr Tyr Glu Asn Glu Thr Lys Leu Ala Leu Val Gly Asn Trp Gly Thr
                885                 890                 895

Thr Gly Leu Thr Tyr Pro Lys Phe Ser Asp Val Thr Gly Lys Ile Lys
            900                 905                 910

Leu Pro Lys Asp Ser Phe Arg Pro Ser Ala Gly Trp Thr Trp Ala Gly
            915                 920                 925

Asp Trp Phe Val Cys Pro Glu Lys Thr Leu Leu His Asp Met Asp Ala
            930                 935                 940

Gly His Leu Ser Phe Val Glu Glu Val Phe Glu Asn Gln Thr Arg Leu
945                 950                 955                 960

Pro Gly Gly Gln Trp Ile Tyr Met Ser Asp Asn Tyr Thr Asp Val Asn
                965                 970                 975

Gly Glu Lys Val Leu Pro Lys Asp Asp Ile Glu Cys Pro Leu Gly Trp
            980                 985                 990

```
Lys Trp Glu Asp Glu Glu Trp Ser  Thr Asp Leu Asn Arg  Ala Val Asp
        995                 1000                 1005

Glu Gln  Gly Trp Glu Tyr Ser  Ile Thr Ile Pro Pro  Glu Arg Lys
   1010                 1015                 1020

Pro Lys  His Trp Val Pro Ala  Glu Lys Met Tyr Tyr  Thr His Arg
   1025                 1030                 1035

Arg Arg  Arg Trp Val Arg Leu  Arg Arg Arg Asp Leu  Ser Gln Met
   1040                 1045                 1050

Glu Ala  Leu Lys Arg His Arg  Gln Ala Glu Ala Glu  Gly Glu Gly
   1055                 1060                 1065

Trp Glu  Tyr Ala Ser Leu Phe  Gly Trp Lys Phe His  Leu Glu Tyr
   1070                 1075                 1080

Arg Lys  Thr Asp Ala Phe Arg  Arg Arg Trp Arg  Arg Arg Met
   1085                 1090                 1095

Glu Pro  Leu Glu Lys Thr Gly  Pro Ala Ala Val Phe  Ala Leu Glu
   1100                 1105                 1110

Gly Ala  Leu Gly Gly Val Met  Asp Asp Lys Ser Glu  Asp Ser Met
   1115                 1120                 1125

Ser Val  Ser Thr Leu Ser Phe  Gly Leu Phe Pro Lys  Ala Leu Gly
   1130                 1135                 1140

Arg Pro  Gly Pro Pro Phe Asn  Ile Thr Pro Arg Arg  Ala Arg Arg
   1145                 1150                 1155

Phe Phe  Leu Arg Cys Ile Ile  Trp Asn Thr Arg Asp  Val Thr Lys
   1160                 1165                 1170

Gly Ala  Phe Gly Asp Met Leu  Asp Thr Pro Asp Ile  Tyr Val Lys
   1175                 1180                 1185

Gly Trp  Met Ile Gly Phe Glu  Glu His Lys Gln Lys  Thr Asp Val
   1190                 1195                 1200

His Tyr  Arg Ser Leu Gly Gly  Glu Gly Asn Phe Asn  Trp Arg Phe
   1205                 1210                 1215

Ile Phe  Pro Phe Asp Tyr Leu  Pro Ala Glu Gln Val  Ala Thr Ile
   1220                 1225                 1230

Ala Lys  Lys Asp Ala Phe Trp  Arg Leu Asp Lys Thr  Glu Ser Lys
   1235                 1240                 1245

Ile Pro  Ala Arg Val Val Phe  Gln Ile Trp Asp Asn  Asp Lys Phe
   1250                 1255                 1260

Ser Phe  Asp Asp Phe Leu Gly  Ser Leu Gln Leu Asp  Leu Asn Arg
   1265                 1270                 1275

Met Pro  Lys Pro Ala Lys Thr  Ala Lys Lys Ala Ser  Leu Asp Gln
   1280                 1285                 1290

Leu Asp  Asp Ala Phe His Pro  Glu Trp Phe Val Ser  Leu Phe Glu
   1295                 1300                 1305

Gln Lys  Thr Val Lys Gly Trp  Trp Pro Cys Val Ala  Glu Glu Gly
   1310                 1315                 1320

Glu Lys  Lys Ile Leu Ala Gly  Lys Leu Glu Met Thr  Leu Glu Ile
   1325                 1330                 1335

Val Ala  Glu Ser Glu His Glu  Glu Arg Pro Ala Gly  Gln Gly Arg
   1340                 1345                 1350

Asp Glu  Pro Asn Met Asn Pro  Lys Leu Glu Asp Pro  Arg Arg Pro
   1355                 1360                 1365

Asp Thr  Ser Phe Leu Trp Phe  Thr Ser Pro Tyr Lys  Thr Met Lys
   1370                 1375                 1380

Phe Ile  Leu Trp Arg Arg Phe  Arg Trp Ala Ile Ile  Leu Phe Ile
```

-continued

```
                1385                1390                1395
Ile Leu Phe Ile Leu Leu Leu Phe Leu Ala Ile Phe Ile Tyr Ala
        1400                1405                1410
Phe Pro Asn Tyr Ala Ala Met Lys Leu Val Lys Pro Phe Ser
        1415                1420                1425

<210> SEQ ID NO 8
<211> LENGTH: 1290
<212> TYPE: PRT
<213> ORGANISM: Artificial
<220> FEATURE:
<223> OTHER INFORMATION: 430 (No Flag) (430)

<400> SEQUENCE: 8

Met Leu Arg Val Phe Ile Leu Tyr Ala Glu Asn Val His Thr Pro Asp
1               5                   10                  15
Thr Asp Ile Ser Asp Ala Tyr Cys Ser Ala Val Phe Ala Gly Val Lys
            20                  25                  30
Lys Arg Thr Lys Val Ile Lys Asn Ser Val Asn Pro Val Trp Asn Glu
        35                  40                  45
Gly Phe Glu Trp Asp Leu Lys Gly Ile Pro Leu Asp Gln Gly Ser Glu
    50                  55                  60
Leu His Val Val Lys Asp His Glu Thr Met Gly Arg Asn Arg Phe
65                  70                  75                  80
Leu Gly Glu Ala Lys Val Pro Leu Arg Glu Val Leu Ala Thr Pro Ser
                85                  90                  95
Leu Ser Ala Ser Phe Asn Ala Pro Leu Leu Asp Thr Lys Lys Gln Pro
            100                 105                 110
Thr Gly Ala Ser Leu Val Leu Gln Val Ser Tyr Thr Pro Leu Pro Gly
        115                 120                 125
Ala Val Pro Leu Phe Pro Pro Thr Pro Leu Glu Pro Ser Pro Thr
    130                 135                 140
Leu Pro Asp Leu Asp Val Val Ala Asp Thr Gly Gly Glu Glu Asp Thr
145                 150                 155                 160
Glu Asp Gln Gly Leu Thr Gly Asp Glu Ala Glu Pro Phe Leu Asp Gln
                165                 170                 175
Ser Gly Gly Pro Gly Ala Pro Thr Thr Pro Arg Lys Leu Pro Ser Arg
            180                 185                 190
Pro Pro Pro His Tyr Pro Gly Ile Lys Arg Lys Arg Ser Ala Pro Thr
        195                 200                 205
Ser Arg Lys Leu Leu Ser Asp Lys Pro Gln Pro Ser Glu Asp Lys Glu
    210                 215                 220
Asp Ile Glu Ser Asn Leu Leu Arg Pro Thr Gly Val Ala Leu Arg Gly
225                 230                 235                 240
Ala His Phe Cys Leu Lys Val Phe Arg Ala Glu Asp Leu Pro Gln Met
                245                 250                 255
Asp Asp Ala Val Met Asp Asn Val Lys Gln Ile Phe Gly Phe Glu Ser
            260                 265                 270
Asn Lys Lys Asn Leu Val Asp Pro Phe Val Glu Val Ser Phe Ala Gly
        275                 280                 285
Lys Met Leu Cys Ser Lys Ile Leu Glu Lys Thr Ala Asn Pro Gln Trp
    290                 295                 300
Asn Gln Asn Ile Thr Leu Pro Ala Met Phe Pro Ser Met Cys Glu Lys
305                 310                 315                 320
Met Arg Ile Arg Ile Ile Asp Trp Asp Arg Leu Thr His Asn Asp Ile
```

```
                    325                 330                 335
        Val Ala Thr Thr Tyr Leu Ser Met Ser Lys Ile Ser Ala Pro Gly Gly
                        340                 345                 350
        Glu Ile Glu Glu Glu Pro Ala Gly Ala Val Lys Pro Ser Lys Ala Ser
                        355                 360                 365
        Asp Leu Asp Asp Tyr Leu Gly Phe Leu Pro Thr Phe Gly Pro Cys Tyr
                    370                 375                 380
        Ile Asn Leu Tyr Gly Ser Pro Arg Glu Phe Thr Gly Phe Pro Asp Pro
        385                 390                 395                 400
        Tyr Thr Glu Leu Asn Thr Gly Lys Gly Glu Gly Val Ala Tyr Arg Gly
                        405                 410                 415
        Arg Leu Leu Leu Ser Leu Glu Thr Lys Leu Val Glu His Ser Glu Gln
                        420                 425                 430
        Lys Val Glu Asp Leu Pro Ala Asp Asp Ile Leu Arg Val Glu Lys Tyr
                        435                 440                 445
        Leu Arg Arg Arg Lys Tyr Ser Leu Phe Ala Ala Phe Tyr Ser Ala Thr
                    450                 455                 460
        Met Leu Gln Asp Val Asp Asp Ala Ile Gln Phe Glu Val Ser Ile Gly
        465                 470                 475                 480
        Asn Tyr Gly Asn Lys Phe Asp Met Thr Cys Leu Pro Leu Ala Ser Thr
                        485                 490                 495
        Thr Gln Tyr Ser Arg Ala Val Phe Asp Gly Cys His Tyr Tyr Tyr Leu
                        500                 505                 510
        Pro Trp Gly Asn Val Lys Pro Val Val Leu Ser Ser Tyr Trp Glu
                        515                 520                 525
        Asp Ile Ser His Arg Ile Glu Thr Gln Asn Gln Leu Leu Gly Ile Ala
                    530                 535                 540
        Asp Arg Leu Glu Ala Gly Leu Glu Gln Val His Leu Ala Leu Lys Ala
        545                 550                 555                 560
        Gln Cys Ser Thr Glu Asp Val Asp Ser Leu Val Ala Gln Leu Thr Asp
                        565                 570                 575
        Glu Leu Ile Ala Gly Cys Ser Gln Pro Leu Gly Asp Ile His Glu Thr
                        580                 585                 590
        Pro Ser Ala Thr His Leu Asp Gln Tyr Leu Tyr Gln Leu Arg Thr His
                        595                 600                 605
        His Leu Ser Gln Ile Thr Glu Ala Ala Leu Ala Leu Lys Leu Gly His
                    610                 615                 620
        Ser Glu Leu Pro Ala Ala Leu Glu Gln Ala Glu Asp Trp Leu Leu Arg
        625                 630                 635                 640
        Leu Arg Ala Leu Ala Glu Glu Pro Gln Asn Ser Leu Pro Asp Ile Val
                        645                 650                 655
        Ile Trp Met Leu Gln Gly Asp Lys Arg Val Ala Tyr Gln Arg Val Pro
                        660                 665                 670
        Ala His Gln Val Leu Phe Ser Arg Arg Gly Ala Asn Tyr Cys Gly Lys
                        675                 680                 685
        Asn Cys Gly Lys Leu Gln Thr Ile Phe Leu Lys Tyr Pro Met Glu Lys
                    690                 695                 700
        Val Pro Gly Ala Arg Met Pro Val Gln Ile Arg Val Lys Leu Trp Phe
        705                 710                 715                 720
        Gly Leu Ser Val Asp Glu Lys Glu Phe Asn Gln Phe Ala Glu Gly Lys
                        725                 730                 735
        Leu Ser Val Phe Ala Glu Thr Tyr Glu Asn Glu Thr Lys Leu Ala Leu
                        740                 745                 750
```

-continued

```
Val Gly Asn Trp Gly Thr Thr Gly Leu Thr Tyr Pro Lys Phe Ser Asp
    755                 760                 765

Val Thr Gly Lys Ile Lys Leu Pro Lys Asp Ser Phe Arg Pro Ser Ala
770                 775                 780

Gly Trp Thr Trp Ala Gly Asp Trp Phe Val Cys Pro Glu Lys Thr Leu
785                 790                 795                 800

Leu His Asp Met Asp Ala Gly His Leu Ser Phe Val Glu Glu Val Phe
                805                 810                 815

Glu Asn Gln Thr Arg Leu Pro Gly Gly Gln Trp Ile Tyr Met Ser Asp
                820                 825                 830

Asn Tyr Thr Asp Val Asn Gly Glu Lys Val Leu Pro Lys Asp Asp Ile
                835                 840                 845

Glu Cys Pro Leu Gly Trp Lys Trp Glu Asp Glu Trp Ser Thr Asp
                850                 855                 860

Leu Asn Arg Ala Val Asp Glu Gln Gly Trp Glu Tyr Ser Ile Thr Ile
865                 870                 875                 880

Pro Pro Glu Arg Lys Pro Lys His Trp Val Pro Ala Glu Lys Met Tyr
                885                 890                 895

Tyr Thr His Arg Arg Arg Arg Trp Val Arg Leu Arg Arg Asp Leu
                900                 905                 910

Ser Gln Met Glu Ala Leu Lys Arg His Arg Gln Ala Glu Ala Glu Gly
                915                 920                 925

Glu Gly Trp Glu Tyr Ala Ser Leu Phe Gly Trp Lys Phe His Leu Glu
                930                 935                 940

Tyr Arg Lys Thr Asp Ala Phe Arg Arg Arg Trp Arg Arg Met
945                 950                 955                 960

Glu Pro Leu Glu Lys Thr Gly Pro Ala Ala Val Phe Ala Leu Glu Gly
                965                 970                 975

Ala Leu Gly Gly Val Met Asp Asp Lys Ser Glu Asp Ser Met Ser Val
                980                 985                 990

Ser Thr Leu Ser Phe Gly Leu Phe Pro Lys Ala Leu Gly Arg Pro Gly
                995                 1000                1005

Pro Pro Phe Asn Ile Thr Pro Arg Arg Ala Arg Arg Phe Phe Leu
    1010                1015                1020

Arg Cys Ile Ile Trp Asn Thr Arg Asp Val Ile Leu Asp Asp Leu
    1025                1030                1035

Ser Leu Thr Gly Glu Lys Met Ser Asp Ile Tyr Val Lys Gly Trp
    1040                1045                1050

Met Ile Gly Phe Glu Glu His Lys Gln Lys Thr Asp Val His Tyr
    1055                1060                1065

Arg Ser Leu Gly Gly Glu Gly Asn Phe Asn Trp Arg Phe Ile Phe
    1070                1075                1080

Pro Phe Asp Tyr Leu Pro Ala Glu Gln Val Ala Thr Ile Ala Lys
    1085                1090                1095

Lys Asp Ala Phe Trp Arg Leu Asp Lys Thr Glu Ser Lys Ile Pro
    1100                1105                1110

Ala Arg Val Val Phe Gln Ile Trp Asp Asn Asp Lys Phe Ser Phe
    1115                1120                1125

Asp Asp Phe Leu Gly Ser Leu Gln Leu Asp Leu Asn Arg Met Pro
    1130                1135                1140

Lys Pro Ala Lys Thr Ala Lys Lys Ala Ser Leu Asp Gln Leu Asp
    1145                1150                1155
```

```
Asp Ala Phe His Pro Glu Trp Phe Val Ser Leu Phe Glu Gln Lys
    1160                1165                1170

Thr Val Lys Gly Trp Trp Pro Cys Val Ala Glu Glu Gly Glu Lys
    1175                1180                1185

Lys Ile Leu Ala Gly Lys Leu Glu Met Thr Leu Glu Ile Val Ala
    1190                1195                1200

Glu Ser Glu His Glu Glu Arg Pro Ala Gly Gln Gly Arg Asp Glu
    1205                1210                1215

Pro Asn Met Asn Pro Lys Leu Glu Asp Pro Arg Arg Pro Asp Thr
    1220                1225                1230

Ser Phe Leu Trp Phe Thr Ser Pro Tyr Lys Thr Met Lys Phe Ile
    1235                1240                1245

Leu Trp Arg Arg Phe Arg Trp Ala Ile Ile Leu Phe Ile Ile Leu
    1250                1255                1260

Phe Ile Leu Leu Leu Phe Leu Ala Ile Phe Ile Tyr Ala Phe Pro
    1265                1270                1275

Asn Tyr Ala Ala Met Lys Leu Val Lys Pro Phe Ser
    1280                1285                1290

<210> SEQ ID NO 9
<211> LENGTH: 1491
<212> TYPE: PRT
<213> ORGANISM: Artificial
<220> FEATURE:
<223> OTHER INFORMATION: 342 No Flag (426)

<400> SEQUENCE: 9

Met Leu Arg Val Phe Ile Leu Tyr Ala Glu Asn Val His Thr Pro Asp
1               5                   10                  15

Thr Asp Ile Ser Asp Ala Tyr Cys Ser Ala Val Phe Ala Gly Val Lys
            20                  25                  30

Lys Arg Thr Lys Val Ile Lys Asn Ser Val Asn Pro Val Trp Asn Glu
        35                  40                  45

Gly Phe Glu Trp Asp Leu Lys Gly Ile Pro Leu Asp Gln Gly Ser Glu
    50                  55                  60

Leu His Val Val Lys Asp His Glu Thr Met Gly Arg Asn Arg Phe
65                  70                  75                  80

Leu Gly Glu Ala Lys Val Pro Leu Arg Glu Val Leu Ala Thr Pro Ser
                85                  90                  95

Leu Ser Ala Ser Phe Asn Ala Pro Leu Leu Asp Thr Lys Lys Gln Pro
            100                 105                 110

Thr Gly Ala Ser Leu Val Leu Gln Val Ser Tyr Thr Pro Leu Pro Gly
        115                 120                 125

Ala Val Pro Leu Phe Pro Pro Thr Pro Leu Glu Pro Ser Pro Thr
    130                 135                 140

Leu Pro Asp Leu Asp Val Val Ala Asp Thr Gly Gly Glu Glu Asp Thr
145                 150                 155                 160

Glu Asp Gln Gly Leu Thr Gly Asp Glu Ala Glu Pro Phe Leu Asp Gln
                165                 170                 175

Ser Gly Gly Pro Gly Ala Pro Thr Thr Pro Arg Lys Leu Pro Ser Arg
            180                 185                 190

Pro Pro Pro His Tyr Pro Gly Ile Lys Arg Lys Arg Ser Ala Pro Thr
        195                 200                 205

Ser Arg Lys Leu Leu Ser Asp Lys Pro Gln Ser Asn Leu Leu Arg Pro
    210                 215                 220
```

-continued

```
Thr Gly Val Ala Leu Arg Gly Ala His Phe Cys Leu Lys Val Phe Arg
225                 230                 235                 240

Ala Glu Asp Leu Pro Gln Met Asp Asp Ala Val Met Asp Asn Val Lys
            245                 250                 255

Gln Ile Phe Gly Phe Glu Ser Asn Lys Lys Asn Leu Val Asp Pro Phe
                260                 265                 270

Val Glu Val Ser Phe Ala Gly Lys Met Leu Cys Ser Lys Ile Leu Glu
        275                 280                 285

Lys Thr Ala Asn Pro Gln Trp Asn Gln Asn Ile Thr Leu Pro Ala Met
    290                 295                 300

Phe Pro Ser Met Cys Glu Lys Met Arg Ile Arg Ile Ile Asp Trp Asp
305                 310                 315                 320

Arg Leu Thr His Asn Asp Ile Val Ala Thr Thr Tyr Leu Ser Met Ser
                325                 330                 335

Lys Ile Ser Ala Pro Gly Gly Glu Ile Glu Glu Pro Ala Gly Ala
                340                 345                 350

Val Lys Pro Ser Lys Ala Ser Asp Leu Asp Asp Tyr Leu Gly Phe Leu
        355                 360                 365

Pro Thr Phe Gly Pro Cys Tyr Ile Asn Leu Tyr Gly Ser Pro Arg Glu
    370                 375                 380

Phe Thr Gly Phe Pro Asp Pro Tyr Thr Glu Leu Asn Thr Gly Lys Gly
385                 390                 395                 400

Glu Gly Val Ala Tyr Arg Gly Arg Leu Leu Ser Leu Glu Thr Lys
                405                 410                 415

Leu Val Glu His Ser Glu Gln Lys Val Glu Asp Leu Pro Ala Asp Asp
                420                 425                 430

Ile Leu Arg Val Glu Lys Tyr Leu Arg Arg Lys Tyr Ser Leu Phe
        435                 440                 445

Ala Ala Phe Tyr Ser Ala Thr Met Leu Gln Asp Val Asp Asp Ala Ile
    450                 455                 460

Gln Phe Glu Val Ser Ile Gly Asn Tyr Gly Asn Lys Phe Asp Met Thr
465                 470                 475                 480

Cys Leu Pro Leu Ala Ser Thr Thr Gln Tyr Ser Arg Ala Val Phe Asp
                485                 490                 495

Gly Cys His Tyr Tyr Tyr Leu Pro Trp Gly Asn Val Lys Pro Val Val
                500                 505                 510

Val Leu Ser Ser Tyr Trp Glu Asp Ile Ser His Arg Ile Glu Thr Gln
        515                 520                 525

Asn Gln Leu Leu Gly Ile Ala Asp Arg Leu Glu Ala Gly Leu Glu Gln
    530                 535                 540

Val His Leu Ala Leu Lys Ala Gln Cys Ser Thr Glu Asp Val Asp Ser
545                 550                 555                 560

Leu Val Ala Gln Leu Thr Asp Glu Leu Ile Ala Gly Cys Ser Gln Pro
                565                 570                 575

Leu Gly Asp Ile His Glu Thr Pro Ser Ala Thr His Leu Asp Gln Tyr
                580                 585                 590

Leu Tyr Gln Leu Arg Thr His His Leu Ser Gln Ile Thr Glu Ala Ala
        595                 600                 605

Leu Ala Leu Lys Leu Gly His Ser Glu Leu Pro Ala Ala Leu Glu Gln
    610                 615                 620

Ala Glu Asp Trp Leu Leu Arg Leu Arg Ala Leu Ala Glu Glu Pro Gln
625                 630                 635                 640

Asn Ser Leu Pro Asp Ile Val Ile Trp Met Leu Gln Gly Asp Lys Arg
```

```
                645                 650                 655
Val Ala Tyr Gln Arg Val Pro Ala His Gln Val Leu Phe Ser Arg Arg
                660                 665                 670

Gly Ala Asn Tyr Cys Gly Lys Asn Cys Gly Lys Leu Gln Thr Ile Phe
                675                 680                 685

Leu Lys Tyr Pro Met Glu Lys Val Pro Gly Ala Arg Met Pro Val Gln
                690                 695                 700

Ile Arg Val Lys Leu Trp Phe Gly Leu Ser Val Asp Glu Lys Glu Phe
705                 710                 715                 720

Asn Gln Phe Ala Glu Gly Lys Leu Ser Val Phe Ala Glu Thr Tyr Glu
                725                 730                 735

Asn Glu Thr Lys Leu Ala Leu Val Gly Asn Trp Gly Thr Thr Gly Leu
                740                 745                 750

Thr Tyr Pro Lys Phe Ser Asp Val Thr Gly Lys Ile Lys Leu Pro Lys
                755                 760                 765

Asp Ser Phe Arg Pro Ser Ala Gly Trp Thr Trp Ala Gly Asp Trp Phe
                770                 775                 780

Val Cys Pro Glu Lys Thr Leu Leu His Asp Met Asp Ala Gly His Leu
785                 790                 795                 800

Ser Phe Val Glu Glu Val Phe Glu Asn Gln Thr Arg Leu Pro Gly Gly
                805                 810                 815

Gln Trp Ile Tyr Met Ser Asp Asn Tyr Thr Asp Val Asn Gly Glu Lys
                820                 825                 830

Val Leu Pro Lys Asp Asp Ile Glu Cys Pro Leu Gly Trp Lys Trp Glu
                835                 840                 845

Asp Glu Glu Trp Ser Thr Asp Leu Asn Arg Ala Val Asp Glu Gln Gly
                850                 855                 860

Trp Glu Tyr Ser Ile Thr Ile Pro Pro Glu Arg Lys Pro Lys His Trp
865                 870                 875                 880

Val Pro Ala Glu Lys Met Tyr Tyr Thr His Arg Arg Arg Arg Trp Val
                885                 890                 895

Arg Leu Arg Arg Arg Asp Leu Ser Gln Met Glu Ala Leu Lys Arg His
                900                 905                 910

Arg Gln Ala Glu Ala Glu Gly Glu Gly Trp Glu Tyr Ala Ser Leu Phe
                915                 920                 925

Gly Trp Lys Phe His Leu Glu Tyr Arg Lys Thr Asp Ala Phe Arg Arg
                930                 935                 940

Arg Arg Trp Arg Arg Arg Met Glu Pro Leu Glu Lys Thr Gly Pro Ala
945                 950                 955                 960

Ala Val Phe Ala Leu Glu Gly Ala Leu Gly Gly Val Met Asp Asp Lys
                965                 970                 975

Ser Glu Asp Ser Met Ser Val Ser Thr Leu Ser Phe Gly Leu Val Arg
                980                 985                 990

Ile Tyr Ile Val Arg Ala Phe Gly Leu Gln Pro Lys Asp Pro Asn Gly
                995                 1000                1005

Lys Cys Asp Pro Tyr Ile Lys Ile Ser Ile Gly Lys Lys Ser Val
                1010                1015                1020

Ser Asp Gln Asp Asn Tyr Ile Pro Cys Thr Leu Glu Pro Val Phe
                1025                1030                1035

Gly Lys Met Phe Glu Leu Thr Cys Thr Leu Pro Leu Glu Lys Asp
                1040                1045                1050

Leu Lys Ile Thr Leu Tyr Asp Tyr Asp Leu Leu Ser Lys Asp Glu
                1055                1060                1065
```

```
Lys Ile Gly Glu Thr Val Val Asp Leu Glu Asn Arg Leu Leu Ser
    1070            1075            1080

Lys Phe Gly Ala Arg Cys Gly Leu Pro Gln Thr Tyr Cys Val Ser
    1085            1090            1095

Gly Pro Asn Gln Trp Arg Asp Gln Leu Arg Pro Ser Gln Leu Leu
    1100            1105            1110

His Leu Phe Cys Gln Gln His Arg Val Lys Ala Pro Val Tyr Arg
    1115            1120            1125

Thr Asp Arg Val Met Phe Gln Asp Lys Glu Tyr Ser Ile Glu Glu
    1130            1135            1140

Ile Glu Ala Gly Arg Ile Pro Asn Pro His Leu Gly Pro Val Glu
    1145            1150            1155

Glu Arg Leu Ala Leu His Val Leu Gln Gln Gln Gly Leu Val Pro
    1160            1165            1170

Glu His Val Glu Ser Arg Pro Leu Tyr Ser Pro Leu Gln Pro Asp
    1175            1180            1185

Ile Glu Gln Gly Lys Leu Gln Met Trp Val Asp Leu Phe Pro Lys
    1190            1195            1200

Ala Leu Gly Arg Pro Gly Pro Pro Phe Asn Ile Thr Pro Arg Arg
    1205            1210            1215

Ala Arg Arg Phe Phe Leu Arg Cys Ile Ile Trp Asn Thr Arg Asp
    1220            1225            1230

Val Ile Leu Asp Asp Leu Ser Leu Thr Gly Glu Lys Met Ser Asp
    1235            1240            1245

Ile Tyr Val Lys Gly Trp Met Ile Gly Phe Glu Glu His Lys Gln
    1250            1255            1260

Lys Thr Asp Val His Tyr Arg Ser Leu Gly Gly Glu Gly Asn Phe
    1265            1270            1275

Asn Trp Arg Phe Ile Phe Pro Phe Asp Tyr Leu Pro Ala Glu Gln
    1280            1285            1290

Val Ala Thr Ile Ala Lys Lys Asp Ala Phe Trp Arg Leu Asp Lys
    1295            1300            1305

Thr Glu Ser Lys Ile Pro Ala Arg Val Val Phe Gln Ile Trp Asp
    1310            1315            1320

Asn Asp Lys Phe Ser Phe Asp Phe Leu Gly Ser Leu Gln Leu
    1325            1330            1335

Asp Leu Asn Arg Met Pro Lys Pro Ala Lys Thr Ala Lys Lys Ala
    1340            1345            1350

Ser Leu Asp Gln Leu Asp Asp Ala Phe His Pro Glu Trp Phe Val
    1355            1360            1365

Ser Leu Phe Glu Gln Lys Thr Val Lys Gly Trp Trp Pro Cys Val
    1370            1375            1380

Ala Glu Glu Gly Glu Lys Lys Ile Leu Ala Gly Lys Leu Glu Met
    1385            1390            1395

Thr Leu Glu Ile Val Ala Glu Ser Glu His Glu Glu Arg Pro Ala
    1400            1405            1410

Gly Gln Gly Arg Asp Glu Pro Asn Met Asn Pro Lys Leu Glu Asp
    1415            1420            1425

Pro Arg Arg Pro Asp Thr Ser Phe Leu Trp Phe Thr Ser Pro Tyr
    1430            1435            1440

Lys Thr Met Lys Phe Ile Leu Trp Arg Arg Phe Arg Trp Ala Ile
    1445            1450            1455
```

```
Ile Leu Phe Ile Ile Leu Phe Ile Leu Leu Leu Phe Leu Ala Ile
    1460                1465                1470

Phe Ile Tyr Ala Phe Pro Asn Tyr Ala Ala Met Lys Leu Val Lys
    1475                1480                1485

Pro Phe Ser
    1490

<210> SEQ ID NO 10
<211> LENGTH: 1428
<212> TYPE: PRT
<213> ORGANISM: Artificial
<220> FEATURE:
<223> OTHER INFORMATION: 341/Nano-Dysferlin (425)

<400> SEQUENCE: 10

Met Leu Arg Val Phe Ile Leu Tyr Ala Glu Asn Val His Thr Pro Asp
1               5                   10                  15

Thr Asp Ile Ser Asp Ala Tyr Cys Ser Ala Val Phe Ala Gly Val Lys
            20                  25                  30

Lys Arg Thr Lys Val Ile Lys Asn Ser Val Asn Pro Val Trp Asn Glu
        35                  40                  45

Gly Phe Glu Trp Asp Leu Lys Gly Ile Pro Leu Asp Gln Gly Ser Glu
    50                  55                  60

Leu His Val Val Lys Asp His Glu Thr Met Gly Arg Asn Arg Phe
65                  70                  75                  80

Leu Gly Glu Ala Lys Val Pro Leu Arg Glu Val Leu Ala Thr Pro Ser
                85                  90                  95

Leu Ser Ala Ser Phe Asn Ala Pro Leu Leu Asp Thr Lys Lys Gln Pro
            100                 105                 110

Thr Gly Ala Ser Leu Val Leu Gln Val Ser Tyr Thr Pro Leu Pro Gly
        115                 120                 125

Ala Val Pro Leu Phe Pro Pro Thr Pro Leu Glu Pro Ser Pro Thr
    130                 135                 140

Leu Pro Asp Leu Asp Val Val Ala Asp Thr Gly Gly Glu Glu Asp Thr
145                 150                 155                 160

Glu Asp Gln Gly Leu Thr Gly Asp Glu Ala Glu Pro Phe Leu Asp Gln
                165                 170                 175

Ser Gly Gly Pro Gly Ala Pro Thr Thr Pro Arg Lys Leu Pro Ser Arg
            180                 185                 190

Pro Pro Pro His Tyr Pro Gly Ile Lys Arg Lys Arg Ser Ala Pro Thr
        195                 200                 205

Ser Arg Lys Leu Leu Ser Asp Lys Pro Gln Asp Phe Gln Ile Arg Val
    210                 215                 220

Gln Val Ile Glu Gly Arg Gln Leu Pro Gly Val Asn Ile Lys Pro Val
225                 230                 235                 240

Val Lys Val Thr Ala Ala Gly Gln Thr Lys Arg Thr Arg Ile His Lys
                245                 250                 255

Gly Asn Ser Pro Leu Phe Asn Glu Thr Leu Phe Phe Asn Leu Phe Asp
            260                 265                 270

Ser Pro Gly Glu Leu Phe Asp Glu Pro Ile Phe Ile Thr Val Val Asp
        275                 280                 285

Ser Arg Ser Leu Arg Thr Asp Ala Leu Leu Gly Glu Phe Arg Met Asp
    290                 295                 300

Val Gly Thr Ile Tyr Arg Glu Pro Arg His Ala Tyr Leu Arg Lys Trp
305                 310                 315                 320
```

```
Leu Leu Leu Ser Asp Pro Asp Phe Ser Ala Gly Ala Arg Gly Tyr
            325             330             335

Leu Lys Thr Ser Leu Cys Val Leu Gly Pro Gly Asp Glu Ala Pro Leu
        340             345             350

Glu Arg Lys Asp Pro Ser Glu Asp Lys Glu Asp Ile Glu Ser Asn Leu
            355             360             365

Leu Arg Pro Thr Gly Val Ala Leu Arg Gly Ala His Phe Cys Leu Lys
370             375             380

Val Phe Arg Ala Glu Leu Pro Gln Met Asp Ala Val Met Asp
385             390             395             400

Asn Val Lys Gln Ile Phe Gly Phe Glu Ser Asn Lys Lys Asn Leu Val
            405             410             415

Asp Pro Phe Val Glu Val Ser Phe Ala Gly Lys Met Leu Cys Ser Lys
            420             425             430

Ile Leu Glu Lys Thr Ala Asn Pro Gln Trp Asn Gln Asn Ile Thr Leu
        435             440             445

Pro Ala Met Phe Pro Ser Met Cys Glu Lys Met Arg Ile Arg Ile Ile
        450             455             460

Asp Trp Asp Arg Leu Thr His Asn Asp Ile Val Ala Thr Thr Tyr Leu
465             470             475             480

Ser Met Ser Lys Ile Ser Ala Pro Gly Gly Glu Ile Glu Glu Glu Pro
            485             490             495

Ala Gly Ala Val Lys Pro Ser Lys Ala Ser Asp Leu Asp Asp Tyr Leu
            500             505             510

Gly Phe Leu Pro Thr Phe Gly Pro Cys Tyr Ile Asn Leu Tyr Gly Ser
        515             520             525

Pro Arg Glu Phe Thr Gly Phe Pro Asp Pro Tyr Thr Glu Leu Asn Thr
        530             535             540

Gly Lys Gly Glu Gly Val Ala Tyr Arg Gly Arg Leu Leu Leu Ser Leu
545             550             555             560

Glu Thr Lys Leu Val Glu His Ser Glu Gln Lys Val Glu Asp Leu Pro
            565             570             575

Ala Asp Asp Ile Leu Arg Val Glu Lys Tyr Leu Arg Arg Lys Tyr
            580             585             590

Ser Leu Phe Ala Ala Phe Tyr Ser Ala Thr Met Leu Gln Asp Val Asp
        595             600             605

Asp Ala Ile Gln Phe Glu Val Ser Ile Gly Asn Tyr Gly Asn Lys Phe
        610             615             620

Asp Met Thr Cys Leu Pro Leu Ala Ser Thr Thr Gln Tyr Ser Arg Ala
625             630             635             640

Val Phe Asp Gly Cys His Tyr Tyr Leu Pro Trp Gly Asn Val Lys
            645             650             655

Pro Val Val Val Leu Ser Ser Tyr Trp Glu Asp Ile Ser His Arg Ile
            660             665             670

Glu Thr Gln Asn Gln Leu Leu Gly Ile Ala Asp Arg Leu Glu Ala Gly
        675             680             685

Leu Glu Gln Val His Leu Ala Leu Lys Ala Gln Cys Ser Thr Glu Asp
        690             695             700

Val Asp Ser Leu Val Ala Gln Leu Thr Asp Glu Leu Ile Ala Gly Cys
705             710             715             720

Ser Gln Pro Leu Gly Asp Ile His Glu Thr Pro Ser Ala Thr His Leu
            725             730             735

Asp Gln Tyr Leu Tyr Gln Leu Arg Thr His His Leu Ser Gln Ile Thr
```

```
                740             745                 750
Glu Ala Ala Leu Ala Leu Lys Leu Gly His Ser Glu Leu Pro Ala Ala
            755                 760                 765

Leu Glu Gln Ala Glu Asp Trp Leu Leu Arg Leu Arg Ala Leu Ala Glu
770                 775                 780

Glu Pro Gln Asn Ser Leu Pro Asp Ile Val Ile Trp Met Leu Gln Gly
785                 790                 795                 800

Asp Lys Arg Val Ala Tyr Gln Arg Val Pro Ala His Gln Val Leu Phe
                805                 810                 815

Ser Arg Arg Gly Ala Asn Tyr Cys Gly Lys Asn Cys Gly Lys Leu Gln
                820                 825                 830

Thr Ile Phe Leu Lys Tyr Pro Met Glu Lys Val Pro Gly Ala Arg Met
            835                 840                 845

Pro Val Gln Ile Arg Val Lys Leu Trp Phe Gly Leu Ser Val Asp Glu
            850                 855                 860

Lys Glu Phe Asn Gln Phe Ala Glu Gly Lys Leu Ser Val Phe Ala Glu
865                 870                 875                 880

Thr Tyr Glu Asn Glu Thr Lys Leu Ala Leu Val Gly Asn Trp Gly Thr
                885                 890                 895

Thr Gly Leu Thr Tyr Pro Lys Phe Ser Asp Val Thr Gly Lys Ile Lys
                900                 905                 910

Leu Pro Lys Asp Ser Phe Arg Pro Ser Ala Gly Trp Thr Trp Ala Gly
            915                 920                 925

Asp Trp Phe Val Cys Pro Glu Lys Thr Leu Leu His Asp Met Asp Ala
            930                 935                 940

Gly His Leu Ser Phe Val Glu Glu Val Phe Glu Asn Gln Thr Arg Leu
945                 950                 955                 960

Pro Gly Gly Gln Trp Ile Tyr Met Ser Asp Asn Tyr Thr Asp Val Asn
                965                 970                 975

Gly Glu Lys Val Leu Pro Lys Asp Asp Ile Glu Cys Pro Leu Gly Trp
                980                 985                 990

Lys Trp Glu Asp Glu Glu Trp Ser  Thr Asp Leu Asn Arg  Ala Val Asp
            995                  1000                1005

Glu Gln  Gly Trp Glu Tyr Ser  Ile Thr Ile Pro Pro  Glu Arg Lys
     1010                1015                1020

Pro Lys  His Trp Val Pro Ala  Glu Lys Met Tyr Tyr  Thr His Arg
     1025                1030                1035

Arg Arg  Arg Trp Val Arg Leu  Arg Arg Arg Asp Leu  Ser Gln Met
     1040                1045                1050

Glu Ala  Leu Lys Arg His Arg  Gln Ala Glu Ala Glu  Gly Glu Gly
     1055                1060                1065

Trp Glu  Tyr Ala Ser Leu Phe  Gly Trp Lys Phe His  Leu Glu Tyr
     1070                1075                1080

Arg Lys  Thr Asp Ala Phe Arg  Arg Arg Arg Trp Arg  Arg Arg Met
     1085                1090                1095

Glu Pro  Leu Glu Lys Thr Gly  Pro Ala Ala Val Phe  Ala Leu Glu
     1100                1105                1110

Gly Ala  Leu Gly Gly Val Met  Asp Asp Lys Ser Glu  Asp Ser Met
     1115                1120                1125

Ser Val  Ser Thr Leu Ser Phe  Gly Leu Phe Pro Lys  Ala Leu Gly
     1130                1135                1140

Arg Pro  Gly Pro Pro Phe Asn  Ile Thr Pro Arg Arg  Ala Arg Arg
     1145                1150                1155
```

```
Phe Phe Leu Arg Cys Ile Ile Trp Asn Thr Arg Asp Val Ile Leu
    1160            1165                1170

Asp Asp Leu Ser Leu Thr Gly Glu Lys Met Ser Asp Ile Tyr Val
    1175            1180                1185

Lys Gly Trp Met Ile Gly Phe Glu Glu His Lys Gln Lys Thr Asp
    1190            1195                1200

Val His Tyr Arg Ser Leu Gly Gly Glu Gly Asn Phe Asn Trp Arg
    1205            1210                1215

Phe Ile Phe Pro Phe Asp Tyr Leu Pro Ala Glu Gln Val Ala Thr
    1220            1225                1230

Ile Ala Lys Lys Asp Ala Phe Trp Arg Leu Asp Lys Thr Glu Ser
    1235            1240                1245

Lys Ile Pro Ala Arg Val Val Phe Gln Ile Trp Asp Asn Asp Lys
    1250            1255                1260

Phe Ser Phe Asp Asp Phe Leu Gly Ser Leu Gln Leu Asp Leu Asn
    1265            1270                1275

Arg Met Pro Lys Pro Ala Lys Thr Ala Lys Lys Ala Ser Leu Asp
    1280            1285                1290

Gln Leu Asp Asp Ala Phe His Pro Glu Trp Phe Val Ser Leu Phe
    1295            1300                1305

Glu Gln Lys Thr Val Lys Gly Trp Trp Pro Cys Val Ala Glu Glu
    1310            1315                1320

Gly Glu Lys Lys Ile Leu Ala Gly Lys Leu Glu Met Thr Leu Glu
    1325            1330                1335

Ile Val Ala Glu Ser Glu His Glu Glu Arg Pro Ala Gly Gln Gly
    1340            1345                1350

Arg Asp Glu Pro Asn Met Asn Pro Lys Leu Glu Asp Pro Arg Arg
    1355            1360                1365

Pro Asp Thr Ser Phe Leu Trp Phe Thr Ser Pro Tyr Lys Thr Met
    1370            1375                1380

Lys Phe Ile Leu Trp Arg Arg Phe Arg Trp Ala Ile Ile Leu Phe
    1385            1390                1395

Ile Ile Leu Phe Ile Leu Leu Leu Phe Leu Ala Ile Phe Ile Tyr
    1400            1405                1410

Ala Phe Pro Asn Tyr Ala Ala Met Lys Leu Val Lys Pro Phe Ser
    1415            1420                1425

<210> SEQ ID NO 11
<211> LENGTH: 2080
<212> TYPE: PRT
<213> ORGANISM: Homo sapiens

<400> SEQUENCE: 11

Met Leu Arg Val Phe Ile Leu Tyr Ala Glu Asn Val His Thr Pro Asp
1               5                   10                  15

Thr Asp Ile Ser Asp Ala Tyr Cys Ser Ala Val Phe Ala Gly Val Lys
                20                  25                  30

Lys Arg Thr Lys Val Ile Lys Asn Ser Val Asn Pro Val Trp Asn Glu
            35                  40                  45

Gly Phe Glu Trp Asp Leu Lys Gly Ile Pro Leu Asp Gln Gly Ser Glu
        50                  55                  60

Leu His Val Val Lys Asp His Glu Thr Met Gly Arg Asn Arg Phe
65                  70                  75                  80

Leu Gly Glu Ala Lys Val Pro Leu Arg Glu Val Leu Ala Thr Pro Ser
```

```
                    85                  90                  95
Leu Ser Ala Ser Phe Asn Ala Pro Leu Leu Asp Thr Lys Lys Gln Pro
            100                 105                 110

Thr Gly Ala Ser Leu Val Leu Gln Val Ser Tyr Thr Pro Leu Pro Gly
            115                 120                 125

Ala Val Pro Leu Phe Pro Pro Thr Pro Leu Glu Pro Ser Pro Thr
            130                 135                 140

Leu Pro Asp Leu Asp Val Val Ala Asp Thr Gly Gly Glu Glu Asp Thr
145                 150                 155                 160

Glu Asp Gln Gly Leu Thr Gly Asp Glu Ala Glu Pro Phe Leu Asp Gln
                165                 170                 175

Ser Gly Gly Pro Gly Ala Pro Thr Thr Pro Arg Lys Leu Pro Ser Arg
                180                 185                 190

Pro Pro Pro His Tyr Pro Gly Ile Lys Arg Lys Ser Ala Pro Thr
            195                 200                 205

Ser Arg Lys Leu Leu Ser Asp Lys Pro Gln Asp Phe Gln Ile Arg Val
            210                 215                 220

Gln Val Ile Glu Gly Arg Gln Leu Pro Gly Val Asn Ile Lys Pro Val
225                 230                 235                 240

Val Lys Val Thr Ala Ala Gly Gln Thr Lys Arg Thr Arg Ile His Lys
                245                 250                 255

Gly Asn Ser Pro Leu Phe Asn Glu Thr Leu Phe Phe Asn Leu Phe Asp
            260                 265                 270

Ser Pro Gly Glu Leu Phe Asp Glu Pro Ile Phe Ile Thr Val Val Asp
            275                 280                 285

Ser Arg Ser Leu Arg Thr Asp Ala Leu Leu Gly Glu Phe Arg Met Asp
            290                 295                 300

Val Gly Thr Ile Tyr Arg Glu Pro Arg His Ala Tyr Leu Arg Lys Trp
305                 310                 315                 320

Leu Leu Leu Ser Asp Pro Asp Asp Phe Ser Ala Gly Ala Arg Gly Tyr
                325                 330                 335

Leu Lys Thr Ser Leu Cys Val Leu Gly Pro Gly Asp Glu Ala Pro Leu
                340                 345                 350

Glu Arg Lys Asp Pro Ser Glu Asp Lys Glu Asp Ile Glu Ser Asn Leu
                355                 360                 365

Leu Arg Pro Thr Gly Val Ala Leu Arg Gly Ala His Phe Cys Leu Lys
                370                 375                 380

Val Phe Arg Ala Glu Asp Leu Pro Gln Met Asp Asp Ala Val Met Asp
385                 390                 395                 400

Asn Val Lys Gln Ile Phe Gly Phe Glu Ser Asn Lys Lys Asn Leu Val
                405                 410                 415

Asp Pro Phe Val Glu Val Ser Phe Ala Gly Lys Met Leu Cys Ser Lys
                420                 425                 430

Ile Leu Glu Lys Thr Ala Asn Pro Gln Trp Asn Gln Asn Ile Thr Leu
                435                 440                 445

Pro Ala Met Phe Pro Ser Met Cys Glu Lys Met Arg Ile Arg Ile Ile
            450                 455                 460

Asp Trp Asp Arg Leu Thr His Asn Asp Ile Val Ala Thr Thr Tyr Leu
465                 470                 475                 480

Ser Met Ser Lys Ile Ser Ala Pro Gly Gly Glu Ile Glu Glu Glu Pro
                485                 490                 495

Ala Gly Ala Val Lys Pro Ser Lys Ala Ser Asp Leu Asp Asp Tyr Leu
                500                 505                 510
```

```
Gly Phe Leu Pro Thr Phe Gly Pro Cys Tyr Ile Asn Leu Tyr Gly Ser
            515                 520                 525

Pro Arg Glu Phe Thr Gly Phe Pro Asp Pro Tyr Thr Glu Leu Asn Thr
    530                 535                 540

Gly Lys Gly Glu Gly Val Ala Tyr Arg Gly Arg Leu Leu Leu Ser Leu
545                 550                 555                 560

Glu Thr Lys Leu Val Glu His Ser Glu Gln Lys Val Glu Asp Leu Pro
                565                 570                 575

Ala Asp Asp Ile Leu Arg Val Glu Lys Tyr Leu Arg Arg Arg Lys Tyr
            580                 585                 590

Ser Leu Phe Ala Ala Phe Tyr Ser Ala Thr Met Leu Gln Asp Val Asp
    595                 600                 605

Asp Ala Ile Gln Phe Glu Val Ser Ile Gly Asn Tyr Gly Asn Lys Phe
    610                 615                 620

Asp Met Thr Cys Leu Pro Leu Ala Ser Thr Thr Gln Tyr Ser Arg Ala
625                 630                 635                 640

Val Phe Asp Gly Cys His Tyr Tyr Leu Pro Trp Gly Asn Val Lys
                645                 650                 655

Pro Val Val Val Leu Ser Ser Tyr Trp Glu Asp Ile Ser His Arg Ile
                660                 665                 670

Glu Thr Gln Asn Gln Leu Leu Gly Ile Ala Asp Arg Leu Glu Ala Gly
                675                 680                 685

Leu Glu Gln Val His Leu Ala Leu Lys Ala Gln Cys Ser Thr Glu Asp
    690                 695                 700

Val Asp Ser Leu Val Ala Gln Leu Thr Asp Glu Leu Ile Ala Gly Cys
705                 710                 715                 720

Ser Gln Pro Leu Gly Asp Ile His Glu Thr Pro Ser Ala Thr His Leu
                725                 730                 735

Asp Gln Tyr Leu Tyr Gln Leu Arg Thr His His Leu Ser Gln Ile Thr
                740                 745                 750

Glu Ala Ala Leu Ala Leu Lys Leu Gly His Ser Glu Leu Pro Ala Ala
            755                 760                 765

Leu Glu Gln Ala Glu Asp Trp Leu Leu Arg Leu Arg Ala Leu Ala Glu
    770                 775                 780

Glu Pro Gln Asn Ser Leu Pro Asp Ile Val Ile Trp Met Leu Gln Gly
785                 790                 795                 800

Asp Lys Arg Val Ala Tyr Gln Arg Val Pro Ala His Gln Val Leu Phe
                805                 810                 815

Ser Arg Arg Gly Ala Asn Tyr Cys Gly Lys Asn Cys Gly Lys Leu Gln
                820                 825                 830

Thr Ile Phe Leu Lys Tyr Pro Met Glu Lys Val Pro Gly Ala Arg Met
            835                 840                 845

Pro Val Gln Ile Arg Val Lys Leu Trp Phe Gly Leu Ser Val Asp Glu
    850                 855                 860

Lys Glu Phe Asn Gln Phe Ala Glu Gly Lys Leu Ser Val Phe Ala Glu
865                 870                 875                 880

Thr Tyr Glu Asn Glu Thr Lys Leu Ala Leu Val Gly Asn Trp Gly Thr
                885                 890                 895

Thr Gly Leu Thr Tyr Pro Lys Phe Ser Asp Val Thr Gly Lys Ile Lys
                900                 905                 910

Leu Pro Lys Asp Ser Phe Arg Pro Ser Ala Gly Trp Thr Trp Ala Gly
            915                 920                 925
```

-continued

```
Asp Trp Phe Val Cys Pro Glu Lys Thr Leu Leu His Asp Met Asp Ala
    930                 935                 940

Gly His Leu Ser Phe Val Glu Val Phe Glu Asn Gln Thr Arg Leu
945                 950                 955                 960

Pro Gly Gly Gln Trp Ile Tyr Met Ser Asp Asn Tyr Thr Asp Val Asn
                965                 970                 975

Gly Glu Lys Val Leu Pro Lys Asp Asp Ile Glu Cys Pro Leu Gly Trp
                980                 985                 990

Lys Trp Glu Asp Glu Glu Trp Ser  Thr Asp Leu Asn Arg  Ala Val Asp
                995                 1000                1005

Glu Gln Gly Trp Glu Tyr Ser  Ile Thr Ile Pro Pro  Glu Arg Lys
    1010                1015                1020

Pro Lys His Trp Val Pro Ala  Glu Lys Met Tyr Tyr  Thr His Arg
    1025                1030                1035

Arg Arg Arg Trp Val Arg Leu  Arg Arg Arg Asp Leu  Ser Gln Met
    1040                1045                1050

Glu Ala Leu Lys Arg His Arg  Gln Ala Glu Ala Glu  Gly Glu Gly
    1055                1060                1065

Trp Glu Tyr Ala Ser Leu Phe  Gly Trp Lys Phe His  Leu Glu Tyr
    1070                1075                1080

Arg Lys Thr Asp Ala Phe Arg  Arg Arg Arg Trp Arg  Arg Arg Met
    1085                1090                1095

Glu Pro Leu Glu Lys Thr Gly  Pro Ala Ala Val Phe  Ala Leu Glu
    1100                1105                1110

Gly Ala Leu Gly Gly Val Met  Asp Asp Lys Ser Glu  Asp Ser Met
    1115                1120                1125

Ser Val Ser Thr Leu Ser Phe  Gly Val Asn Arg Pro  Thr Ile Ser
    1130                1135                1140

Cys Ile Phe Asp Tyr Gly Asn  Arg Tyr His Leu Arg  Cys Tyr Met
    1145                1150                1155

Tyr Gln Ala Arg Asp Leu Ala  Ala Met Asp Lys Asp  Ser Phe Ser
    1160                1165                1170

Asp Pro Tyr Ala Ile Val Ser  Phe Leu His Gln Ser  Gln Lys Thr
    1175                1180                1185

Val Val Val Lys Asn Thr Leu  Asn Pro Thr Trp Asp  Gln Thr Leu
    1190                1195                1200

Ile Phe Tyr Glu Ile Glu Ile  Phe Gly Glu Pro Ala  Thr Val Ala
    1205                1210                1215

Glu Gln Pro Pro Ser Ile Val  Val Glu Leu Tyr Asp  His Asp Thr
    1220                1225                1230

Tyr Gly Ala Asp Glu Phe Met  Gly Arg Cys Ile Cys  Gln Pro Ser
    1235                1240                1245

Leu Glu Arg Met Pro Arg Leu  Ala Trp Phe Pro Leu  Thr Arg Gly
    1250                1255                1260

Ser Gln Pro Ser Gly Glu Leu  Leu Ala Ser Phe Glu  Leu Ile Gln
    1265                1270                1275

Arg Glu Lys Pro Ala Ile His  His Ile Pro Gly Phe  Glu Val Gln
    1280                1285                1290

Glu Thr Ser Arg Ile Leu Asp  Glu Ser Glu Asp Thr  Asp Leu Pro
    1295                1300                1305

Tyr Pro Pro Pro Gln Arg Glu  Ala Asn Ile Tyr Met  Val Pro Gln
    1310                1315                1320

Asn Ile Lys Pro Ala Leu Gln  Arg Thr Ala Ile Glu  Ile Leu Ala
```

-continued

```
            1325                1330                1335

Trp Gly Leu Arg Asn Met Lys Ser Tyr Gln Leu Ala Asn Ile Ser
        1340                1345                1350

Ser Pro Ser Leu Val Val Glu Cys Gly Gly Gln Thr Val Gln Ser
        1355                1360                1365

Cys Val Ile Arg Asn Leu Arg Lys Asn Pro Asn Phe Asp Ile Cys
        1370                1375                1380

Thr Leu Phe Met Glu Val Met Leu Pro Arg Glu Glu Leu Tyr Cys
        1385                1390                1395

Pro Pro Ile Thr Val Lys Val Ile Asp Asn Arg Gln Phe Gly Arg
        1400                1405                1410

Arg Pro Val Val Gly Gln Cys Thr Ile Arg Ser Leu Glu Ser Phe
        1415                1420                1425

Leu Cys Asp Pro Tyr Ser Ala Glu Ser Pro Ser Pro Gln Gly Gly
        1430                1435                1440

Pro Asp Asp Val Ser Leu Leu Ser Pro Gly Glu Asp Val Leu Ile
        1445                1450                1455

Asp Ile Asp Asp Lys Glu Pro Leu Ile Pro Ile Gln Glu Glu Glu
        1460                1465                1470

Phe Ile Asp Trp Trp Ser Lys Phe Phe Ala Ser Ile Gly Glu Arg
        1475                1480                1485

Glu Lys Cys Gly Ser Tyr Leu Glu Lys Asp Phe Asp Thr Leu Lys
        1490                1495                1500

Val Tyr Asp Thr Gln Leu Glu Asn Val Glu Ala Phe Glu Gly Leu
        1505                1510                1515

Ser Asp Phe Cys Asn Thr Phe Lys Leu Tyr Arg Gly Lys Thr Gln
        1520                1525                1530

Glu Glu Thr Glu Asp Pro Ser Val Ile Gly Glu Phe Lys Gly Leu
        1535                1540                1545

Phe Lys Ile Tyr Pro Leu Pro Glu Asp Pro Ala Ile Pro Met Pro
        1550                1555                1560

Pro Arg Gln Phe His Gln Leu Ala Ala Gln Gly Pro Gln Glu Cys
        1565                1570                1575

Leu Val Arg Ile Tyr Ile Val Arg Ala Phe Gly Leu Gln Pro Lys
        1580                1585                1590

Asp Pro Asn Gly Lys Cys Asp Pro Tyr Ile Lys Ile Ser Ile Gly
        1595                1600                1605

Lys Lys Ser Val Ser Asp Gln Asp Asn Tyr Ile Pro Cys Thr Leu
        1610                1615                1620

Glu Pro Val Phe Gly Lys Met Phe Glu Leu Thr Cys Thr Leu Pro
        1625                1630                1635

Leu Glu Lys Asp Leu Lys Ile Thr Leu Tyr Asp Tyr Asp Leu Leu
        1640                1645                1650

Ser Lys Asp Glu Lys Ile Gly Glu Thr Val Val Asp Leu Glu Asn
        1655                1660                1665

Arg Leu Leu Ser Lys Phe Gly Ala Arg Cys Gly Leu Pro Gln Thr
        1670                1675                1680

Tyr Cys Val Ser Gly Pro Asn Gln Trp Arg Asp Gln Leu Arg Pro
        1685                1690                1695

Ser Gln Leu Leu His Leu Phe Cys Gln Gln His Arg Val Lys Ala
        1700                1705                1710

Pro Val Tyr Arg Thr Asp Arg Val Met Phe Gln Asp Lys Glu Tyr
        1715                1720                1725
```

Ser Ile Glu Glu Ile Glu Ala Gly Arg Ile Pro Asn Pro His Leu
1730                1735                1740

Gly Pro Val Glu Glu Arg Leu Ala Leu His Val Leu Gln Gln Gln
    1745                1750                1755

Gly Leu Val Pro Glu His Val Glu Ser Arg Pro Leu Tyr Ser Pro
1760                1765                1770

Leu Gln Pro Asp Ile Glu Gln Gly Lys Leu Gln Met Trp Val Asp
    1775                1780                1785

Leu Phe Pro Lys Ala Leu Gly Arg Pro Gly Pro Phe Asn Ile
1790                1795                1800

Thr Pro Arg Arg Ala Arg Arg Phe Phe Leu Arg Cys Ile Ile Trp
    1805                1810                1815

Asn Thr Arg Asp Val Ile Leu Asp Asp Leu Ser Leu Thr Gly Glu
1820                1825                1830

Lys Met Ser Asp Ile Tyr Val Lys Gly Trp Met Ile Gly Phe Glu
    1835                1840                1845

Glu His Lys Gln Lys Thr Asp Val His Tyr Arg Ser Leu Gly Gly
1850                1855                1860

Glu Gly Asn Phe Asn Trp Arg Phe Ile Phe Pro Phe Asp Tyr Leu
    1865                1870                1875

Pro Ala Glu Gln Val Cys Thr Ile Ala Lys Lys Asp Ala Phe Trp
1880                1885                1890

Arg Leu Asp Lys Thr Glu Ser Lys Ile Pro Ala Arg Val Val Phe
    1895                1900                1905

Gln Ile Trp Asp Asn Asp Lys Phe Ser Phe Asp Asp Phe Leu Gly
1910                1915                1920

Ser Leu Gln Leu Asp Leu Asn Arg Met Pro Lys Pro Ala Lys Thr
    1925                1930                1935

Ala Lys Lys Cys Ser Leu Asp Gln Leu Asp Asp Ala Phe His Pro
1940                1945                1950

Glu Trp Phe Val Ser Leu Phe Glu Gln Lys Thr Val Lys Gly Trp
    1955                1960                1965

Trp Pro Cys Val Ala Glu Glu Gly Glu Lys Lys Ile Leu Ala Gly
1970                1975                1980

Lys Leu Glu Met Thr Leu Glu Ile Val Ala Glu Ser Glu His Glu
    1985                1990                1995

Glu Arg Pro Ala Gly Gln Gly Arg Asp Glu Pro Asn Met Asn Pro
2000                2005                2010

Lys Leu Glu Asp Pro Arg Arg Pro Asp Thr Ser Phe Leu Trp Phe
    2015                2020                2025

Thr Ser Pro Tyr Lys Thr Met Lys Phe Ile Leu Trp Arg Arg Phe
2030                2035                2040

Arg Trp Ala Ile Ile Leu Phe Ile Ile Leu Phe Ile Leu Leu Leu
    2045                2050                2055

Phe Leu Ala Ile Phe Ile Tyr Ala Phe Pro Asn Tyr Ala Ala Met
2060                2065                2070

Lys Leu Val Lys Pro Phe Ser
    2075                2080

<210> SEQ ID NO 12
<211> LENGTH: 6911
<212> TYPE: DNA
<213> ORGANISM: Homo sapiens

<400> SEQUENCE: 12

```
tcgaccgccc agccaggtgc aaaatgccgt gtcattggga gactccgcag ccggagcatt      60
agattacagc tcgacggagc tcgggaaggg cggcggggt ggaagatgag cagaagcccc     120
tgttctcgga acgccggctg acaagcgggg tgagcgcagg cggggcgggg acccagccta    180
gcccactgga gcagccgggg gtggcccgtt ccccttttaag agcaactgct ctaagccagg    240
agccagagat tcgagccggc ctcgcccagc cagccctctc cagcgagggg acccacaagc    300
ggcgcctcgg ccctcccgac ctttccgagc cctctttgcg ccctgggcgc acggggccct    360
acacgcgcca agcatgctga gggtcttcat cctctatgcc gagaacgtcc acacacccga    420
caccgacatc agcgatgcct actgctccgc ggtgtttgca ggggtgaaga agagaaccaa    480
agtcatcaag aacagcgtga accctgtatg gaatgaggga tttgaatggg acctcaaggg    540
catcccctg gaccagggct ctgagcttca tgtggtggtc aaagaccatg agacgatggg    600
gaggaacagg ttcctggggg aagccaaggt cccactccga gaggtcctcg ccaccccag    660
tctgtccgcc agcttcaatg cccccctgct ggacaccaag aagcagccca caggggcctc    720
gctggtcctg caggtgtcct acacaccgct gcctggagct gtgcccctgt cccgccccc    780
tactcctctg gagccctccc cgactctgcc tgacctggat gtagtggcag acacaggagg    840
agaggaagac acagaggacc agggactcac tggagatgag gcggagccat tcctggatca    900
aagcggaggc ccggggggctc ccaccacccc aaggaaacta ccttcacgtc ctccgcccca    960
ctaccccggg atcaaaagaa agcgaagtgc gcctacatct agaaagctgc tgtcagacaa   1020
accgcaggat ttccagatca gggtccaggt gatcgagggg cgccagctgc cggggtgaa    1080
catcaagcct gtggtcaagg ttaccgctgc agggcagacc aagcggacgc ggatccacaa   1140
gggaaacagc ccactcttca atgagactct tttcttcaac ttgtttgact ctcctgggga   1200
gctgtttgat gagcccatct ttatcacggt ggtagactct cgttctctca ggacagatgc   1260
tctcctcggg gagttccgga tggacgtggg caccatttac agagagcccc ggcacgccta   1320
tctcaggaag tggctgctgc tctcagaccc tgatgacttc tctgctgggg ccagaggcta   1380
cctgaaaaca gccttttgtg tgctggggcc tggggacgaa gcgcctctgg agagaaaaga   1440
cccctctgaa gacaaggagg acattgaaag caacctgctc cggcccacag gcgtagccct   1500
gcgaggagcc cacttctgcc tgaaggtctt ccgggccgag gacttgccgc agatggacga   1560
tgccgtgatg gacaacgtga acagatcttt ggcttcgag agtaacaaga gaacttggt    1620
ggacccctt gtggaggtca gctttgcggg gaaaatgctg tgcagcaaga tcttggagaa   1680
gacggccaac cctcagtgga accagaacat cacactgcct gccatgtttc cctccatgtg   1740
cgaaaaaatg aggattcgta tcatagactg ggaccgcctg actcacaatg acatcgtggc   1800
taccacctac ctgagtatgt cgaaaatctc tgcccctgga ggagaaatag aagaggagcc   1860
tgcaggtgct gtcaagcctt cgaaagcctc agacttggat gactacctgg gcttcctccc   1920
cactttttgggg ccctgctaca tcaacctcta tggcagtccc agagagttca caggcttccc   1980
agacccctac acagagctca acacaggcaa gggggaaggt gtggcttatc gtggccggct   2040
tctgctctcc ctggagacca gctggtgga gcacagtgaa cagaaggtgg aggaccttcc   2100
tgcggatgac atcctccggg tggagaagta ccttaggagg cgcaagtact ccctgtttgc   2160
ggccttctac tcagccacca tgctgcagga tgtggatgat gccatccagt ttgaggtcag   2220
catcgggaac tacgggaaca gttcgacat gacctgcctg ccgctggcct ccaccactca   2280
gtacagccgt gcagtctttg acgggtgcca ctactactac ctaccctggg gtaacgtgaa   2340
```

```
acctgtggtg gtgctgtcat cctactggga ggacatcagc catagaatcg agactcagaa    2400
ccagctgctt gggattgctg accggctgga agctggcctg gagcaggtcc acctggccct    2460
gaaggcgcag tgctccacgg aggacgtgga ctcgctggtg gctcagctga cggatgagct    2520
catcgcaggc tgcagccagc ctctgggtga catccatgag acaccctctg ccacccacct    2580
ggaccagtac ctgtaccagc tgcgcaccca tcacctgagc caaatcactg aggctgccct    2640
ggccctgaag ctcggccaca gtgagctccc tgcagtctg  gagcaggcgg aggactggct    2700
cctgcgtctg cgtgccctgg cagaggagcc ccagaacagc ctgccggaca tcgtcatctg    2760
gatgctgcag ggagacaagc gtgtggcata ccagcgggtg cccgcccacc aagtcctctt    2820
ctcccggcgg ggtgccaact actgtggcaa gaattgtggg aagctacaga caatctttct    2880
gaaatatccg atggagaagg tgcctggcgc ccggatgcca gtgcagatac gggtcaagct    2940
gtggtttggg ctctctgtgg atgagaagga gttcaaccag tttgctgagg ggaagctgtc    3000
tgtctttgct gaaacctatg agaacgagac taagttggcc cttgttggga actggggcac    3060
aacgggcctc acctacccca gtttttctga cgtcacgggc aagatcaagc tacccaagga    3120
cagcttccgc ccctcggccg gctggacctg ggctggagat tggttcgtgt gtccggagaa    3180
gactctgctc catgacatgg acgccggtca cctgagcttc gtggaagagg tgtttgagaa    3240
ccagacccgg cttcccggag ccagtggat  ctacatgagt gacaactaca ccgatgtgaa    3300
cggggagaag gtgcttccca aggatgacat tgagtgccca ctgggctgga gtgggaaga    3360 tgaggaatgg tccacagacc tcaaccgggc tgtcgatgag caaggctggg agtatagcat    3420
caccatcccc ccggagcgga agccgaagca ctgggtccct gctgagaaga tgtactacac    3480
acaccgacgg cggcgctggg tgcgcctgcg caggagggat ctcagccaaa tggaagcact    3540
gaaaaggcac aggcaggcgg aggcggaggg cgagggctgg gagtacgcct ctctttttgg    3600
ctggaagttc cacctcgagt accgcaagac agatgccttc cgccgccgcc gctggcgccg    3660
tcgcatggag ccactggaga agacgggggcc tgcagctgtg tttgcccttg ag gggccct    3720 gggcggcgtg atggatgaca agagtgaaga ttccatgtcc gtctccacct tgagcttcgg    3780
tgtgaacaga cccacgattt cctgcatatt cgactatggg aaccgctacc atctacgctg    3840
ctacatgtac caggcccggg acctggctgc gatggacaag gactcttttt ctgatcccta    3900
tgccatcgtc tccttcctgc accagagcca gaagacggtg gtggtgaaga acaccccttaa    3960 ccccacctgg gaccagacgc tcatcttcta cgagatcgag atctttggcg agccggccac    4020
agttgctgag caaccgccca gcattgtggt ggagctgtac gaccatgaca cttatggtgc    4080
agacgagttt atgggtcgct gcatctgtca accgagtctg gaacggatgc cacggctggc    4140
ctggttccca ctgacgaggg gcagccagcc gtcggggga ctgctggcct cttttgagct    4200
catccagaga gagaagccgg ccatccacca tattcctggt tttgaggtgc aggagacatc    4260
aaggatcctg gatgagtctg aggacacaga cctgccctac ccaccacccc agagggaggc    4320
caacatctac atggttcctc agaacatcaa gccagcgctc cagcgtaccg ccatcgagat    4380
cctggcatgg ggcctgcgga acatgaagag ttaccagctg ccaacatct  cctcccccag    4440 cctcgtggta gagtgtgggg ccagacggt  gcagtcctgt gtcatcagga acctccggaa    4500 gaacccaac  tttgacatct gcaccctctt catggaagtg atgctgccca gggaggagct    4560
ctactgcccc cccatcaccg tcaaggtcat cgataaccgc cagtttggcc gccggcctgt    4620
ggtgggccag tgtaccatcc gctccctgga gagcttcctg tgtgaccct  actcggcgga    4680
```

```
gagtccatcc ccacagggtg gcccagacga tgtgagccta ctcagtcctg ggaagacgt    4740
gctcatcgac attgatgaca aggagcccct catccccatc caggaggaag agttcatcga    4800
ttggtggagc aaattctttg cctccatagg ggagagggaa aagtgcggct cctacctgga    4860
gaaggatttt gacaccctga aggtctatga cacacagctg gagaatgtgg aggcctttga    4920
gggcctgtct gacttttgta acaccttcaa gctgtaccgg ggcaagacgc aggaggagac    4980
agaagatcca tctgtgattg gtgaatttaa gggcctcttc aaaatttatc ccctcccaga    5040
agacccagcc atccccatgc ccccaagaca gttccaccag ctggccgccc agggacccca    5100
ggagtgcttg gtccgtatct acattgtccg agcatttggc ctgcagccca aggaccccaa    5160
tggaaagtgt gatccttaca tcaagatctc catagggaag aaatcagtga gtgaccagga    5220
taactacatc ccctgcacgc tggagcccgt atttggaaag atgttcgagc tgacctgcac    5280
tctgcctctg gagaaggacc taaagatcac tctctatgac tatgacctcc tctccaagga    5340
cgaaaagatc ggtgagacgg tcgtcgacct ggagaacagg ctgctgtcca gtttggggc    5400
tcgctgtgga ctcccacaga cctactgtgt ctctggaccg aaccagtggc gggaccagct    5460
ccgcccctcc cagctcctcc acctcttctg ccagcagcat agagtcaagg cacctgtgta    5520
ccggacagac cgtgtaatgt ttcaggataa agaatattcc attgaagaga tagaggctgg    5580
caggatccca aacccacacc tgggcccagt ggaggagcgt ctggctctgc atgtgcttca    5640
gcagcagggc ctggtcccgg agcacgtgga gtcacggccc ctctacagcc ccctgcagcc    5700
agacatcgag caggggaagc tgcagatgtg ggtcgaccta tttccgaagg ccctggggcg    5760
gcctggacct cccttcaaca tcaccccacg gagagccaga aggttttccc tgcgttgtat    5820
tatctggaat accagagatg tgatcctgga tgacctgagc ctcacggggg agaagatgag    5880
cgacatttat gtgaaaggtt ggatgattgg ctttgaagaa cacaagcaaa agacagacgt    5940
gcattatcgt tccctgggag gtgaaggcaa cttcaactgg aggttcattt cccccttcga    6000
ctacctgcca gctgagcaag tctgtaccat tgccaagaag gatgccttct ggaggctgga    6060
caagactgag agcaaaatcc cagcacgagt ggtgttccag atctgggaca atgacaagtt    6120
ctcctttgat gattttctgg gctccctgca gctcgatctc aaccgcatgc caagccagc    6180
caagacagcc aagaagtgct ccttggacca gctggatgat gctttccacc agaatggtt    6240
tgtgtccctt tttgagcaga aaacagtgaa gggctggtgg ccctgtgtag cagaagaggg    6300
tgagaagaaa atactggcgg gcaagctgga aatgaccttg gagattgtag cagagagtga    6360
gcatgaggag cggcctgctg gccagggccg ggatgagccc aacatgaacc ctaagcttga    6420
ggacccaagg cgccccgaca cctccttcct gtggtttacc tccccataca agaccatgaa    6480
gttcatcctg tggcggcgtt ccggtgggc catcatcctc ttcatcatcc tcttcatcct    6540
gctgctgttc ctggccatct tcatctacgc cttcccgaac tatgctgcca tgaagctggt    6600
gaagcccttc agctgaggac tctcctgccc tgtagaaggg gccgtggggt ccctccagc    6660
atgggactgg cctgcctcct ccgcccagct cggcgagctc ctccagacct cctaggcctg    6720
attgtcctgc cagggtgggc agacagacag atggaccggc ccacactccc agagttgcta    6780
acatggagct ctgagatcac cccacttcca tcatttcctt ctcccccaac caacgctt    6840
tttggatcag ctcagacata tttcagtata aaacagttgg aaccacaaaa aaaaaaaaa    6900
aaaaaaaaaa a                                                       6911

<210> SEQ ID NO 13
<211> LENGTH: 18
```

```
<212> TYPE: DNA
<213> ORGANISM: Artificial
<220> FEATURE:
<223> OTHER INFORMATION: Primer

<400> SEQUENCE: 13
ccgacacgcc tacctgag                                                    18

<210> SEQ ID NO 14
<211> LENGTH: 19
<212> TYPE: DNA
<213> ORGANISM: Artificial
<220> FEATURE:
<223> OTHER INFORMATION: Primer

<400> SEQUENCE: 14
ccggcactaa aatcgtcag                                                   19
```